(12) United States Patent
Chung et al.

(10) Patent No.: US 8,884,008 B2
(45) Date of Patent: Nov. 11, 2014

(54) PEPTIDE NUCLEIC ACID DERIVATIVES WITH GOOD CELL PENETRATION AND STRONG AFFINITY FOR NUCLEIC ACID

(71) Applicant: CTI Bio, Seoul (KR)

(72) Inventors: Shin Chung, Yongin-si (KR);
Heui-Yeon Kim, Incheon (KR);
Hyun-Jin Park, Anyang-si (KR);
Mi-Ran Kim, Anseong-si (KR);
Jong-Ook Lee, Seoul (KR)

(73) Assignee: OliPass Corporation, Suwon (KR)

( * ) Notice: Subject to any disclaimer, the term of this patent is extended or adjusted under 35 U.S.C. 154(b) by 0 days.

(21) Appl. No.: 14/109,327

(22) Filed: Dec. 17, 2013

(65) Prior Publication Data
US 2014/0155604 A1    Jun. 5, 2014

Related U.S. Application Data

(62) Division of application No. 12/922,322, filed as application No. PCT/KR2009/001256 on Mar. 13, 2009, now Pat. No. 8,680,253.

(30) Foreign Application Priority Data

Mar. 14, 2008 (KR) .................. 10-2008-0023658
Nov. 11, 2008 (KR) .................. 10-2008-0111459

(51) Int. Cl.
*C07D 239/00* (2006.01)
*C07D 239/70* (2006.01)

(52) U.S. Cl.
USPC .......................... 544/224; 544/242; 544/245

(58) Field of Classification Search
USPC .................................... 544/224, 242, 245
See application file for complete search history.

(56) References Cited

U.S. PATENT DOCUMENTS

| 5,773,571 | A | 6/1998 | Nielsen et al. |
| 6,133,444 | A | 10/2000 | Coull et al. |
| 6,617,422 | B1 | 9/2003 | Nielsen et al. |
| 2004/0265885 | A1 | 12/2004 | Uhlmann et al. |

FOREIGN PATENT DOCUMENTS

| EP | 0586474 | 9/2001 |
| WO | WO92/20702 | 11/1992 |
| WO | WO 2008/061091 | 5/2008 |

OTHER PUBLICATIONS

Bijsterbosch et al., "In vivo fate of phosphorothioate antisense oligodeoxynucleotides: predominant uptake by scavenger receptors on endothelial liver cells", Nucleic Acids Research, 1997, vol. 25, No. 16, 3290-3296.

Braasch et al., "Novel antisense and Peptide Nucleic Acid Strategies for Controlling Gene Expression", Biochemistry, 2002, vol. 41, No. 14, 4503-4510.

Brookes, "Antisense Drug ISIS 301012 Lowers LDL Cholesterol Alone and in Combination with Statins", Medscape.com, accessed on Feb. 19, 2009.

Chan et al., "Antisense Oligonucleotides: From Design to Therapeutic Application", Clinical and Experimental Pharmacology and Physiology, 2006, 33, 533-540.

Debart et al.,"Chemical Modifications to Improve the Cellular Uptake of Oligonucleotides". Current Topics in Medicinal Chemistry, 2007, 7, 727-737.

Doyle et al., "Inhibition of Gene Expression Inside Cells by Peptide Nucleic Acids: Effect of mRNA Sequence, Mismatched Bases, and PNA Length", Biochemistry 2001, 40, 53-64.

Dragulescu-Andrasi et al., "Cell-permeable GPNA with appropriate backbone stereochemistry and spacing binds sequence-specifically to RNA", Chem. Commun. 2005, 14, 244-246.

Dragulescu-Andrasi et al., "A Simple γ-Backbone Modification Preorganizes Peptide Nucleic Acid into a Helical Structure", J. Am. Chem. Soc. 2006, 128, 10258-10267.

Eckstein, "Nucleoside Phosphorothioates", Ann. Rev. Biochem, 1985, 54, 367-402.

Egholm, "PNA hybridizes to complementary oligonucleotides obeying the Watson-Crick hydrogen-bonding rules", Nature, 1993, vol. 365, 566-568.

Fabani et al., "miR-122 targeting with LNA/2'-O-methyl oligonucleotide mixmers, peptide nucleic acids (PNA), and PNA-peptide conjugates", RNA, 2008, 14, 336-346.

Falkiewicz, "Peptide nucleic acids and their structural modifications", Acta Biochimica Polonica, vol. 46, No. 3, 1999, 509-529.

Haaima et al., "Increased DNA binding and sequence discrimination of PNA oligomers containing 2,6-diaminopurine", Nucleic Acid Research, 1997, vol. 25, No. 22, 4639-4643.

Haima et al., "Peptide Nucleic Acids (PNAs) Containing Thymine Monomers Derived from Chiral Amino Acids: Hybridization and Solubility Properties of D-Lysine PNA", Angew. Chem. Int. Ed. Engl. 1996, 35, No. 17, 1939-1942.

Hanvey et al., "Antisense and Antigene Properties of Peptide Nucleic Acids". Science, 1992, vol. 258, 1481-1485.

Harrison et al , "Inhibition of Human Telomerase by PNA-Cationic Peptide Conjugates", Bioorg Med Chem Lett., May 3, 1999, 9(9), 1273-1278.

Hu et al , "Inhibiting Gene Expression with Peptide Nucleic Acid (PNA)-Peptide Conjugates that Target Chromosomal DNA", Biochemistry, Jun. 26, 2007, 46(25), 7581-7589.

Hudson et al., "Nucleobase Modified peptide Nucleic Acid", Nucleosides Nucleotides & Nucleic Acids, 2003, vol. 22, Nos. 5, 8, 1029-1033.

Karkare et al., "Promising nucleic acid analogs and mimics: characteristic features and applications of PNA, LNA, and morpholino", Appl. Microbiol Biotechnol 2006, 71, 575-586.

(Continued)

*Primary Examiner* — Jezia Riley
(74) *Attorney, Agent, or Firm* — Heslin Rothenberg Farley & Mesiti P.C.; Andrew K. Gonsalves, Esq.

(57) ABSTRACT

The present invention provides a novel class of peptide nucleic acid derivatives, which show good cell penetration and strong binding affinity for nucleic acid.

Figure 1:
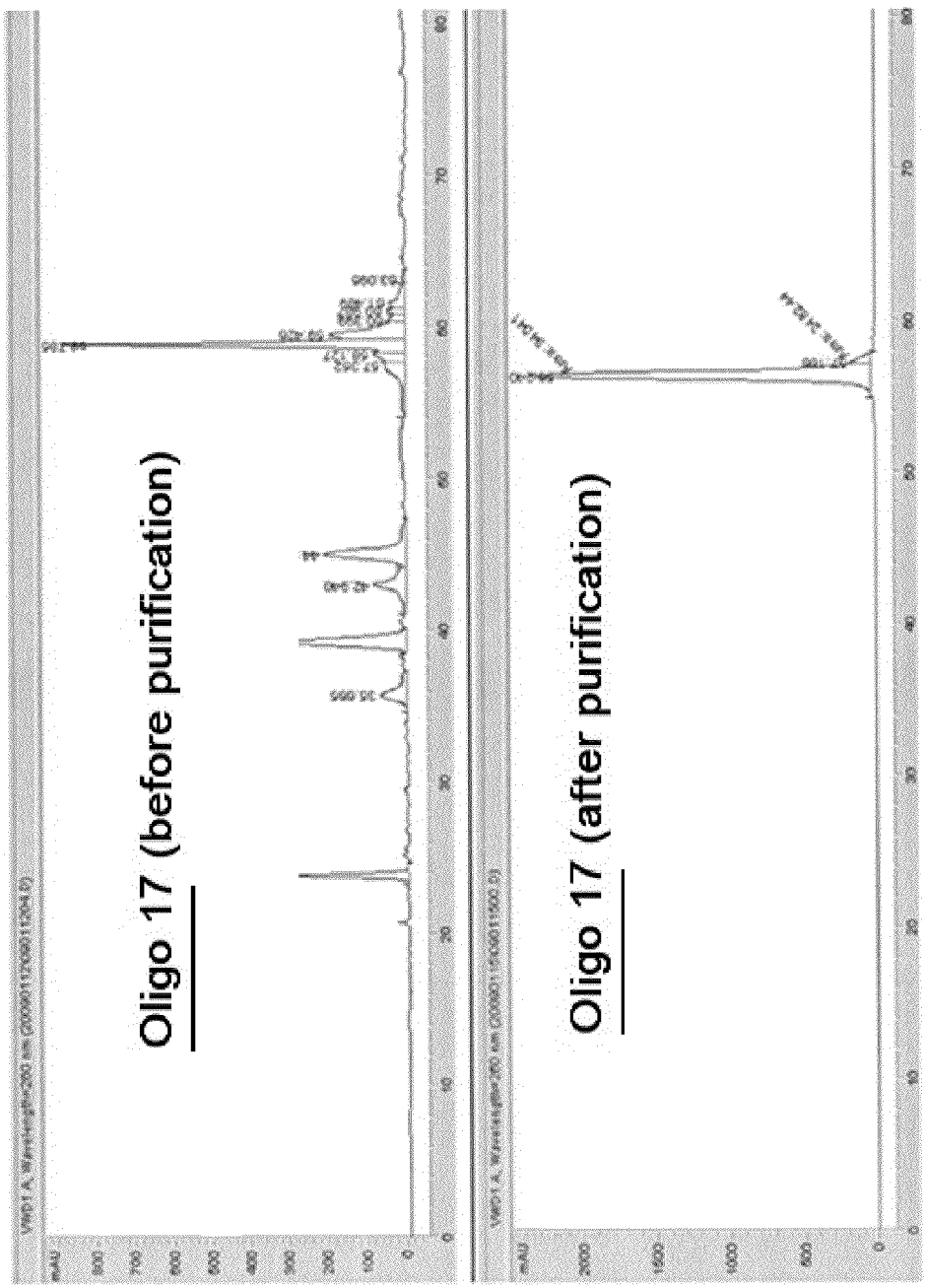

**2 Claims, 11 Drawing Sheets
(6 of 11 Drawing Sheet(s) Filed in Color)**

(56) References Cited

OTHER PUBLICATIONS

Karras et al., "Peptide Nucleic Acids are Potent Modulators of Endogenous Pre-mRNA Splicing of the Murine Interleukin-5 Receptor-α Chain", Biochemistry, 2001, 40, 7853-7859.

Kaur et al., "Thermodynamic, Counterion, and Hydration Effects for the Incorporation of Locked Nucleic Acid Nucleotides into DNA Duplexes", Biochemistry, 2006, 45, 7347-7355.

Kilk et al., "Targeting of antisense PNA oligomers to human galanin receptor type 1 mRNA", Neuropeptides, 38, 2004, 316-324.

Koppelhus, "Cellular delivery of peptide nucleic acid (PNA)", Advanced Drug Delivery Reviews 55, 2003, 267-280.

Lee et al., "Peptide Nucleic Acid Synthesis by Novel Amide Formation", Organic Letters, 2007, vol. 9, No. 17, 3291-3293.

Liu, "Technology Evaluation: ISIS-113715, Isis" Current Opinion in Molecular Therapeutics, 2004, 6(3), 331-336.

Ljungstrom et al., "Cellular Uptake of Adamantyl Conjugated Peptide Nucleic Acids", Bioconjugate Chem., 1999, 10, 965-972.

Maison et al., "Multicomponent Synthesis of Novel Amino Acid-Nucleobase Chimeras: a Versatile Approach to PNA-Monomers", Bioorganic & Medicinal Chemistry 8, 2000, 1343-1360.

Muratovska et al., "Targeting peptide nucleic acid (PNA) oligomers to mitochondria within cells by conjugation to lipophilic cations: implications for mitochondrial DNA replication, expression and disease", Nucleic Acids Research, 2001, vol. 29, No. 9, 1852-1863.

Nielsen et al., "Sequence-Selective Recognition of DNA by Strand Displacement with a Thymine-Substituted Polyamide", Science, 1991, vol. 254, 1497-1500.

Rajeev et al., "High-Affinity Peptide Nucleic Acid Oligomers Containing Tricyclic Cytosine Analogues", Organic Letters, 2002, vol. 4, No. 25, 4395-4398.

Ray et al., "Peptide nucleic acid (PNA): its medical and biotechnical applications and promise for the future", FASEB, 2000, vol. 14, 1041-1060.

Shiraishi et al., "Down-regulation of MDM2 and activation of p53 in human cancer cells by antisense 9-aminoacridine-PNA (peptide nucleic acid) conjugates", Nucleic Acids Research, 2004, vol. 32, No. 16, 4893-4902.

Shiraishi et al., "Subnanomolar antisense activity of phosphonate-peptide nucleic acid (PNA) conjugates delivered by cationic lipids to HeLa cells", Nucleic Acids Research, 2008, vol. 36, No. 13, 4424-4432.

Siwkowski et al., "Identification and functional validation of PNAs that inhibit murine CD40 expression by redirection of splicing", Nucleic Acids Research, 2004, vol. 32, No. 9, 2695-2706.

Stein et al., "Oligodeoxynucleotides as Inhibitors of Gene Expression: A Review", Cancer Research, 1988, 48, 2659-2668.

Turner et al., "Cell-penetrating peptide conjugates of peptide nucleic acids (PNA) as inhibitors of HIV-1 Tat-dependent trans-activation in cells", Nucleic Acids Research, 2005, vol. 33, No. 21, 6837-6849.

Wagner et al., "Synthesis of Amino Acids with unnatural Nucleobases or Chromophores Suitable for Use in Model Electron-Transfer Studies", Eur. J. Org. Chem., 2003, 3673-3679.

Wojciechowski et al., "Flourescence and Hybridization Properties of Peptide Nucleic Acid Containing a Substituted Phenylpyrrolocytosine Designed to Engage Guanine with an Additional H-Bond", J. Am. Chem. Soc., 2008, 130, 12574-12575.

Wu et al., "Synthesis of N-Boc and N-Fmoc dipeptoids with nucleobase residues as peptoid nucleic acid monomers", Tetrahedron, 2001, 57, 3373-3381.

Zhou et al., "Synthesis of cell-permeable peptide nucleic acids and characterization of their hybridization and uptake properties", Science Direct, Bioorganic & Medicinal Chemistry Letters 16, 2006, 4931-4935.

Zhou, et al., "Novel Binding and Efficient Cellular Uptake of Guanidine-Based Peptide Nucleic Acids (GPNA)" J.Am. Chem. Soc., 2003, 125, 6878-6879.

Figure 7:
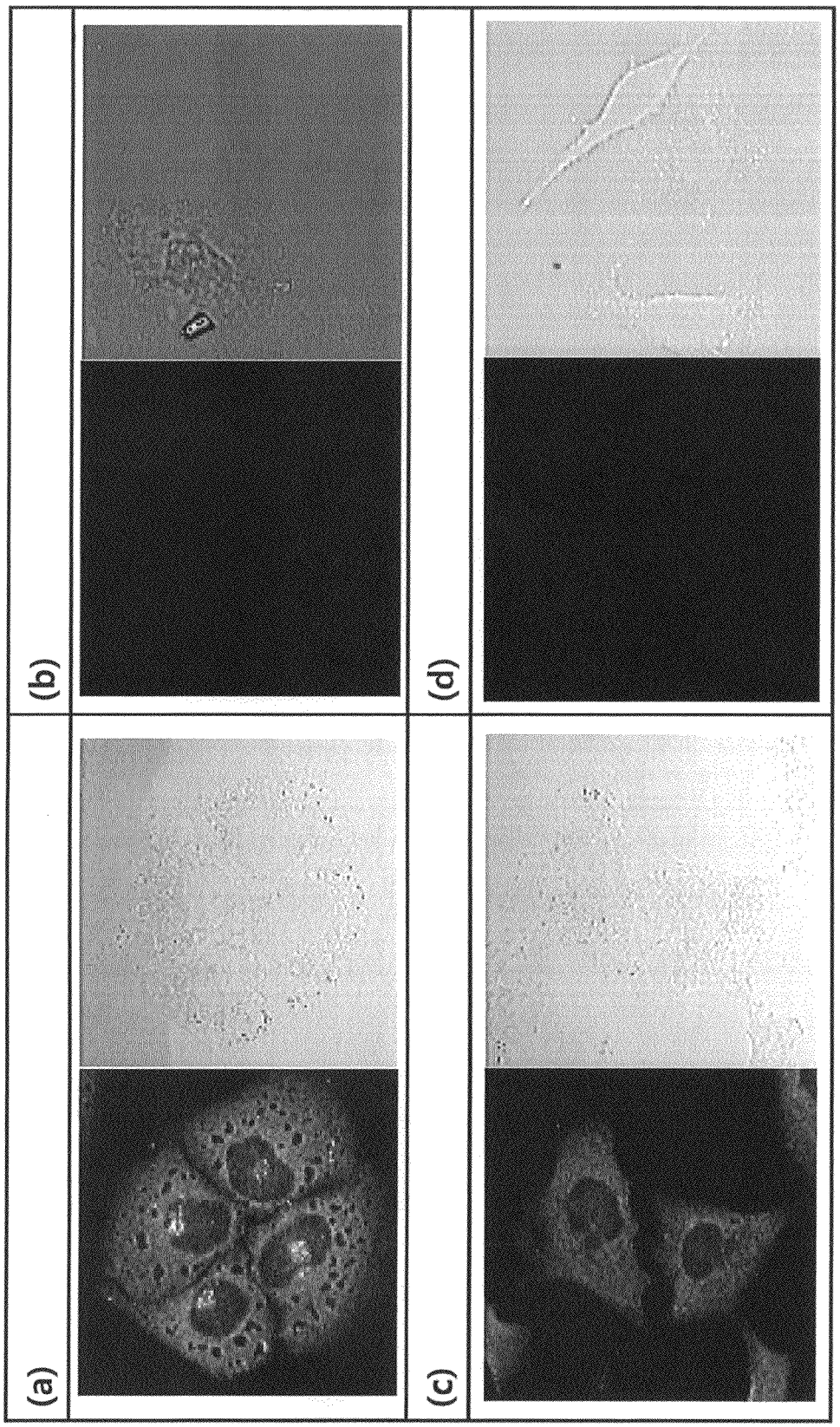

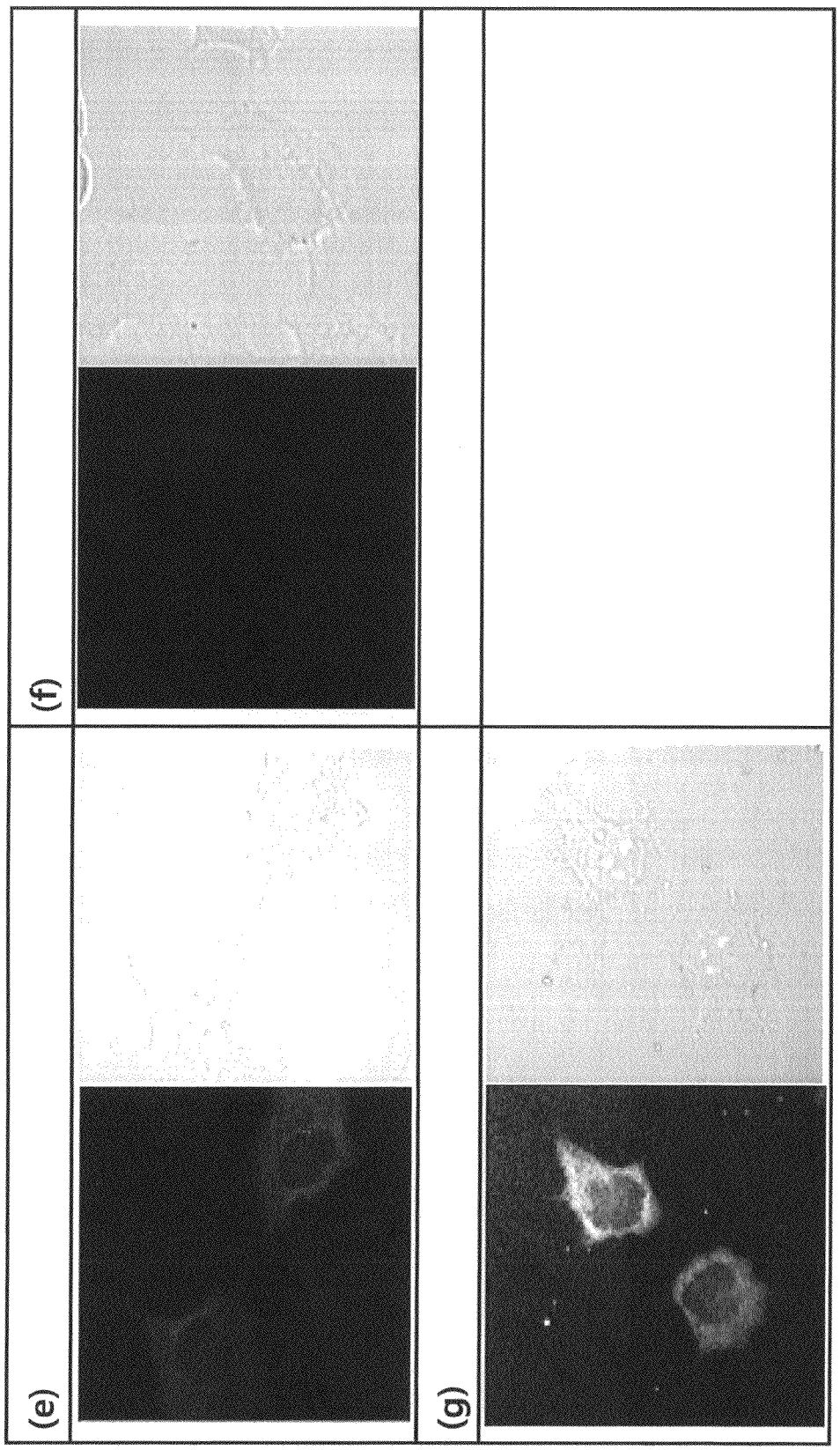
Figure 7 (continued from previous page)

PEPTIDE NUCLEIC ACID DERIVATIVES WITH GOOD CELL PENETRATION AND STRONG AFFINITY FOR NUCLEIC ACID

CROSS REFERENCE TO RELATED APPLICATION

This application is a divisional patent application of allowed application Ser. No. 12/922,322, filed Sep. 13, 2010. Allowed application Ser. No. 12/922,322 is a National Phase filing of International Application No. PCT/KR2009/001256, filed Mar. 13, 2009, which claims priority to Korean Application No. 10-2008-23658, filed Mar. 14, 2008, and Korean Application No. 10-2008-111459, filed Nov. 11, 2008. The entire content of each prior application is hereby incorporated by reference.

REFERENCE TO A SEQUENCE LISTING

This application contains a sequence listing, provided as a paper copy, as required under 37 C.F.R. §1.821(c), and is herein incorporated by reference in its entirety, as required under 37 C.F.R. §1.52(e)(5). A copy of the sequence listing is also provided as required under 37 C.F.R. §1.821(e), as a computer readable form.

FIELD OF INVENTION

The present invention relates to peptide nucleic acid derivatives chemically modified to show good cell penetration and strong affinity for nucleic acid.

BRIEF DESCRIPTIONS OF DRAWINGS

This patent or application file contains at least one drawing executed in color. Copies of this patent or patent application publication with color drawing(s) will be provided by the Office upon request and payment of the necessary fee.

FIG. 1 provides HPLC chromatograms before and after purification of Oligo 17 by reverse phase HPLC.

Figure 2:
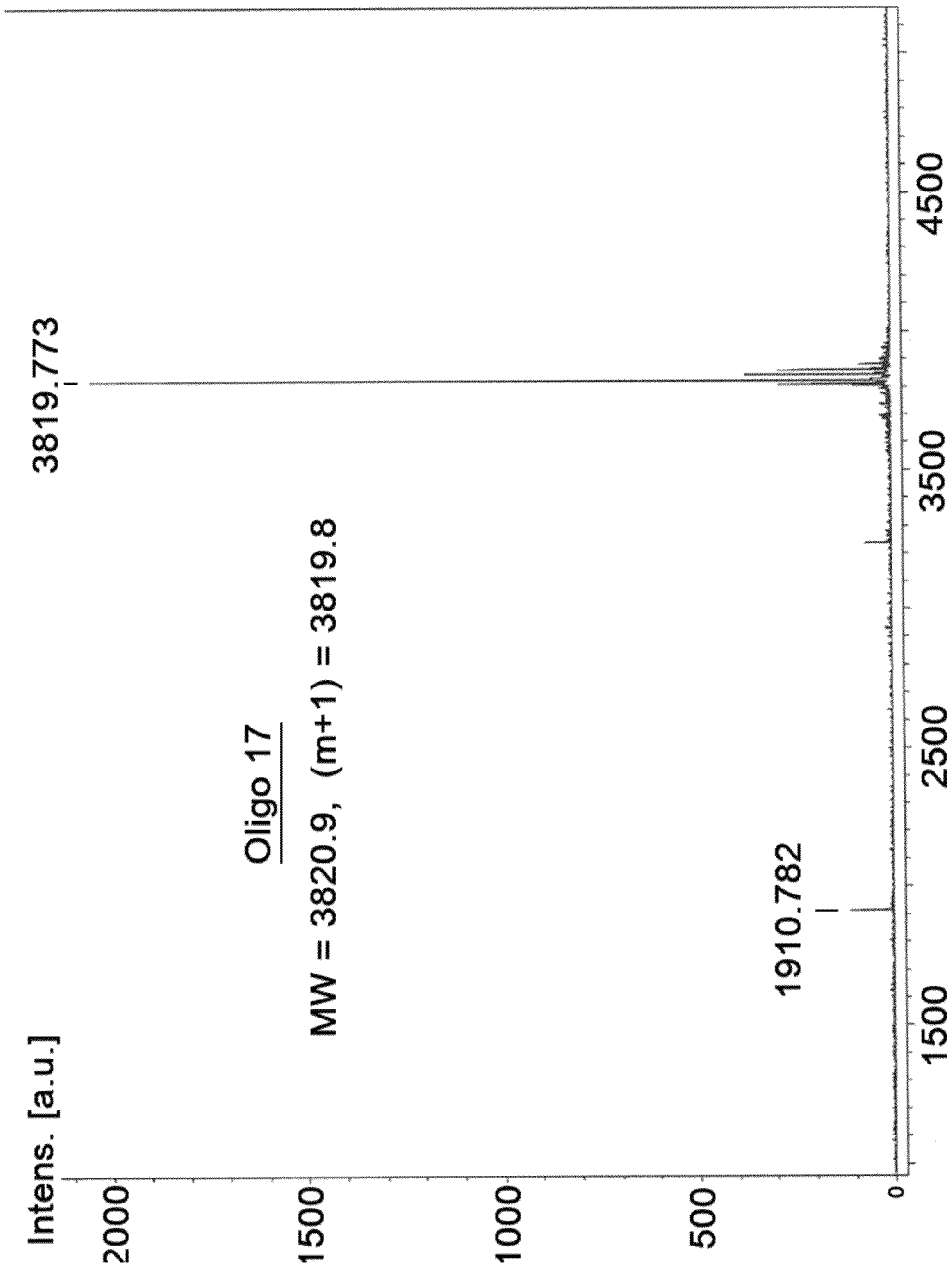

FIG. 2 provides a MALDI-TOF mass spectrum for a purified batch of Oligo 17.

Figure 3:
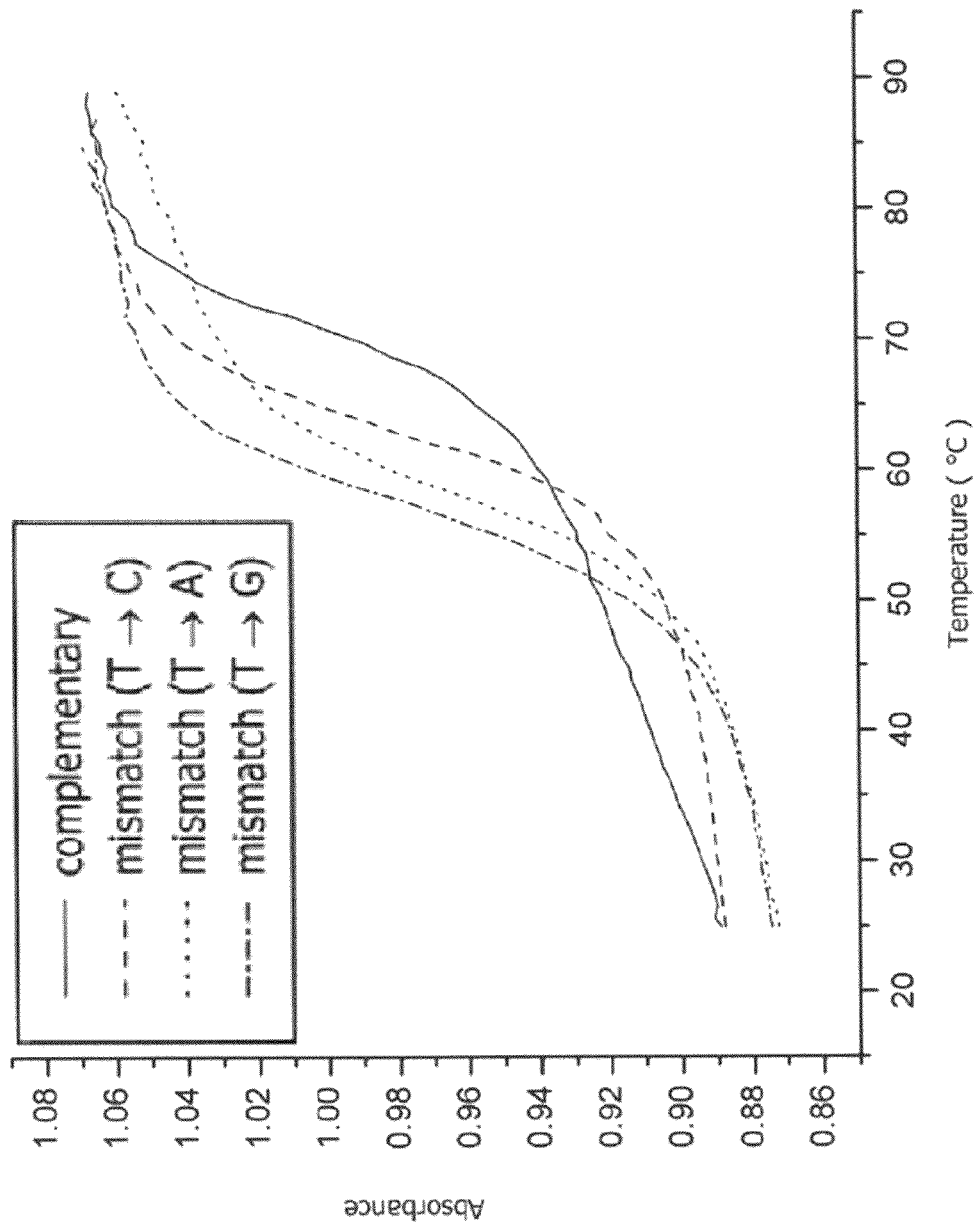

FIG. 3 provides graphs of absorbance changes with temperature for Oligo 17 against complementary or mismatch DNA.

Figure 4:
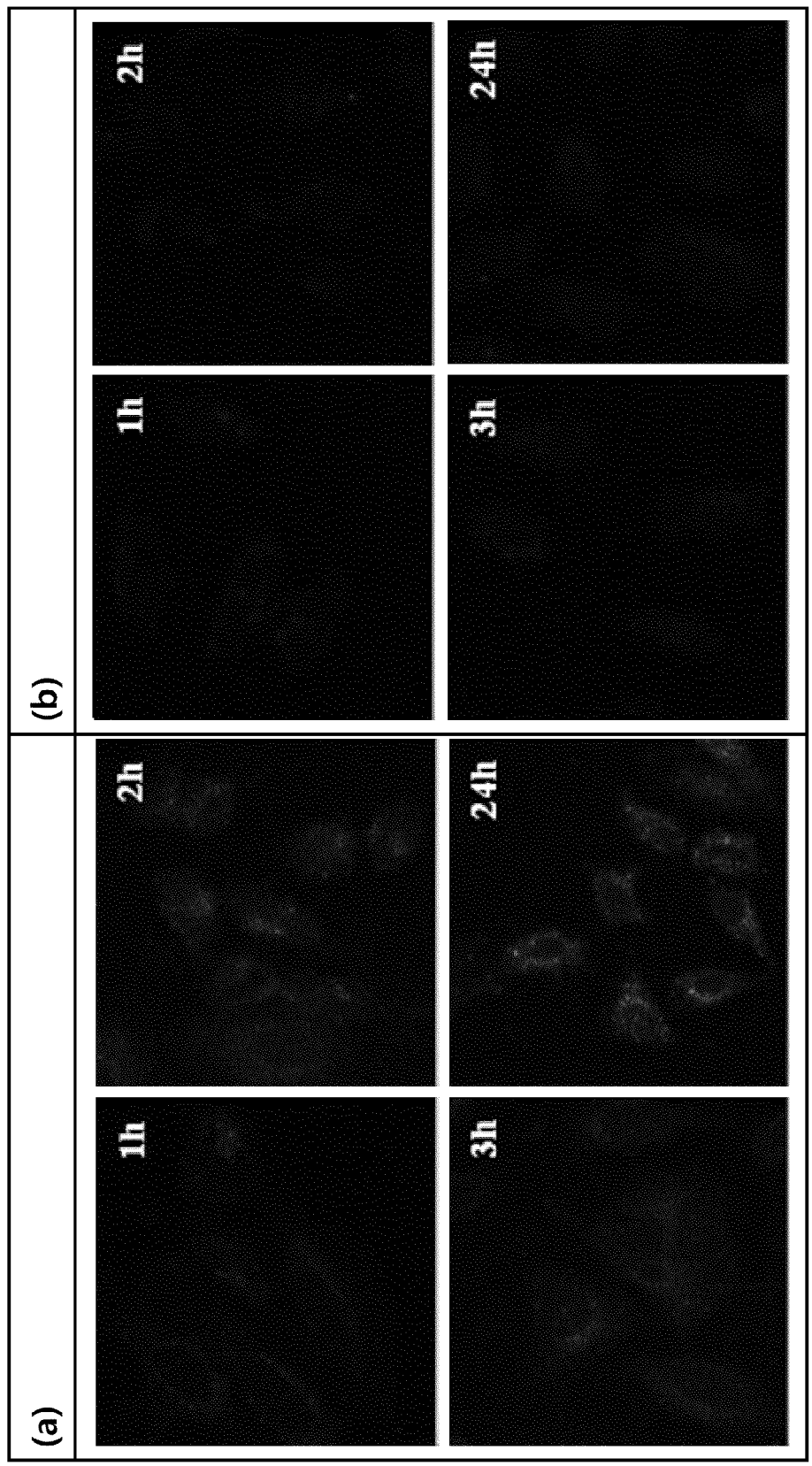

FIGS. 4(a) and 4(b) provide confocal microscopy images (at 63× objective) 1, 2, 3 and 24 h after HeLa cells were treated with Oligo 1 and Oligo 2 at 5 µM, respectively.

Figure 5:
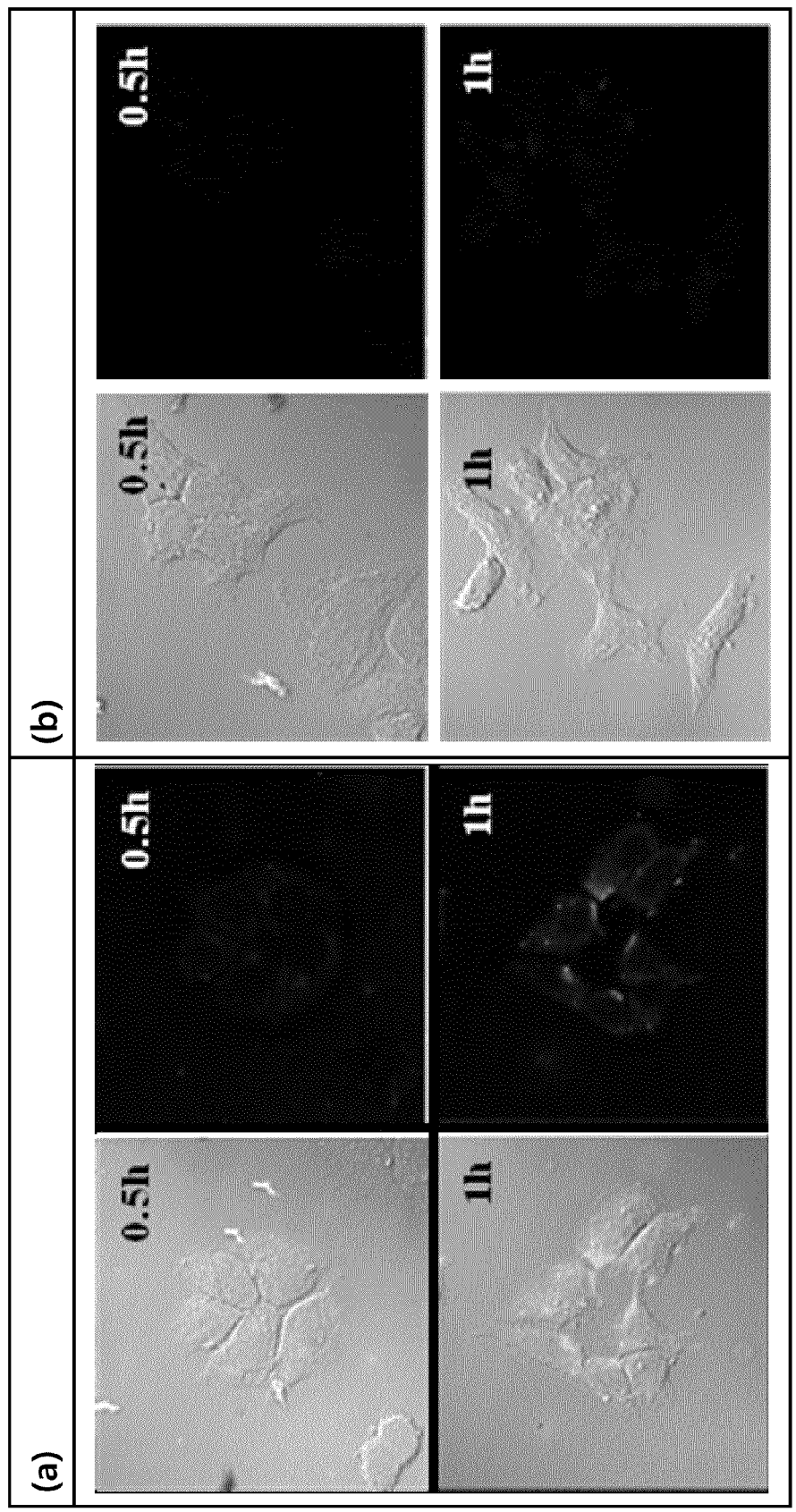

FIGS. 5(a) and 5(b) provide confocal microscopy images (at 63× objective) 0.5 and 1 h after MCF-7 cells were treated with Oligo 6 and Oligo 7 at 2.5 µM, respectively.

Figure 6:
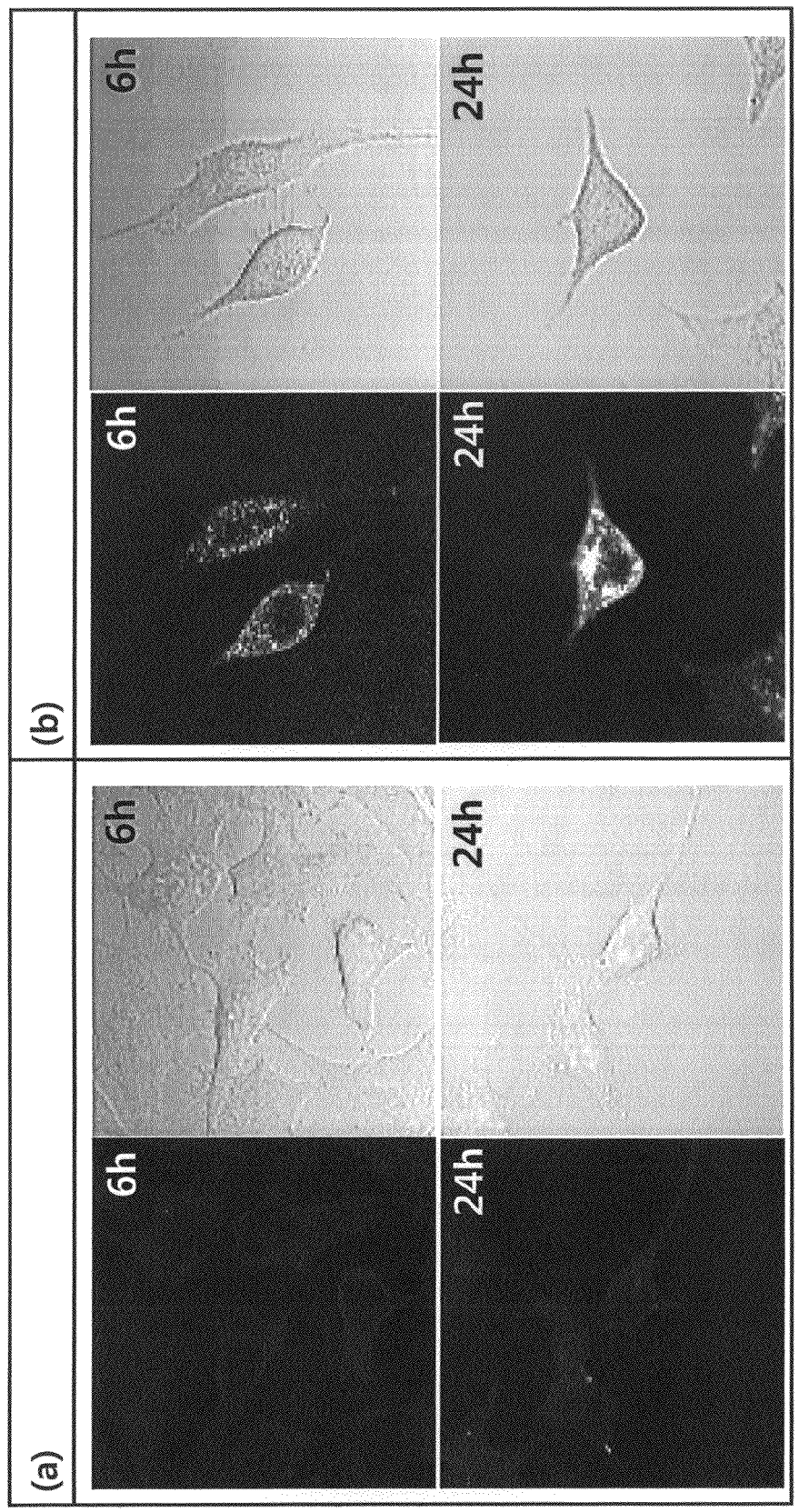

FIGS. 6(a) and 6(b) provide confocal microscopy pictures (at 40× objective) 6 or 24 h after HeLa cells were treated with Oligo 1 and Oligo 6 at 1 µM, respectively.

FIGS. 7(a) and 7(b) provide confocal microscopy pictures (40× objective) 24 h after JAR cells were treated with Oligo 21 and Oligo 28 at 2 µM, respectively.

FIGS. 7(c) and 7(d) provide confocal microscopy pictures (at 40× objective) 24 h after A549 cells were treated with Oligo 21 and Oligo 28 at 2 µM, respectively.

FIGS. 7(e) and 7(f) provide confocal microscopy pictures (at 40× objective) 12 h after HeLa cells were treated with Oligo 21 and Oligo 28 at 2 µM, respectively.

FIG. 7(g) provides confocal microscopy pictures (at 40× objective) 24 h after HeLa cells were treated with Oligo 21 at 2 µM.

Figure 8:
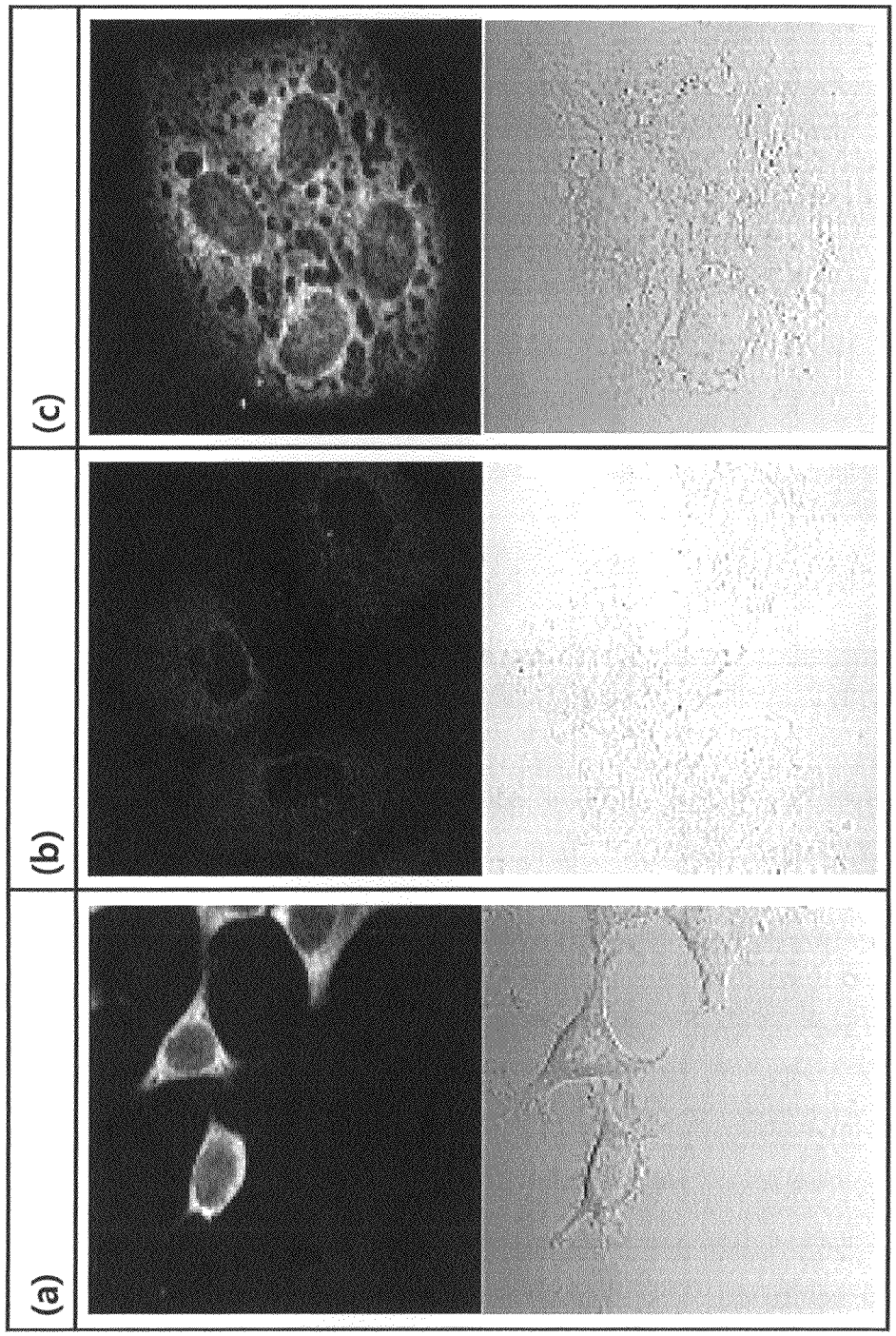

FIGS. 8(a), 8(b) and 8(c) provide confocal microscopy images (40× objective) 24 h after HeLa, A549, and JAR cells were treated with 2 µM Oligo 22, respectively.

Figure 9:
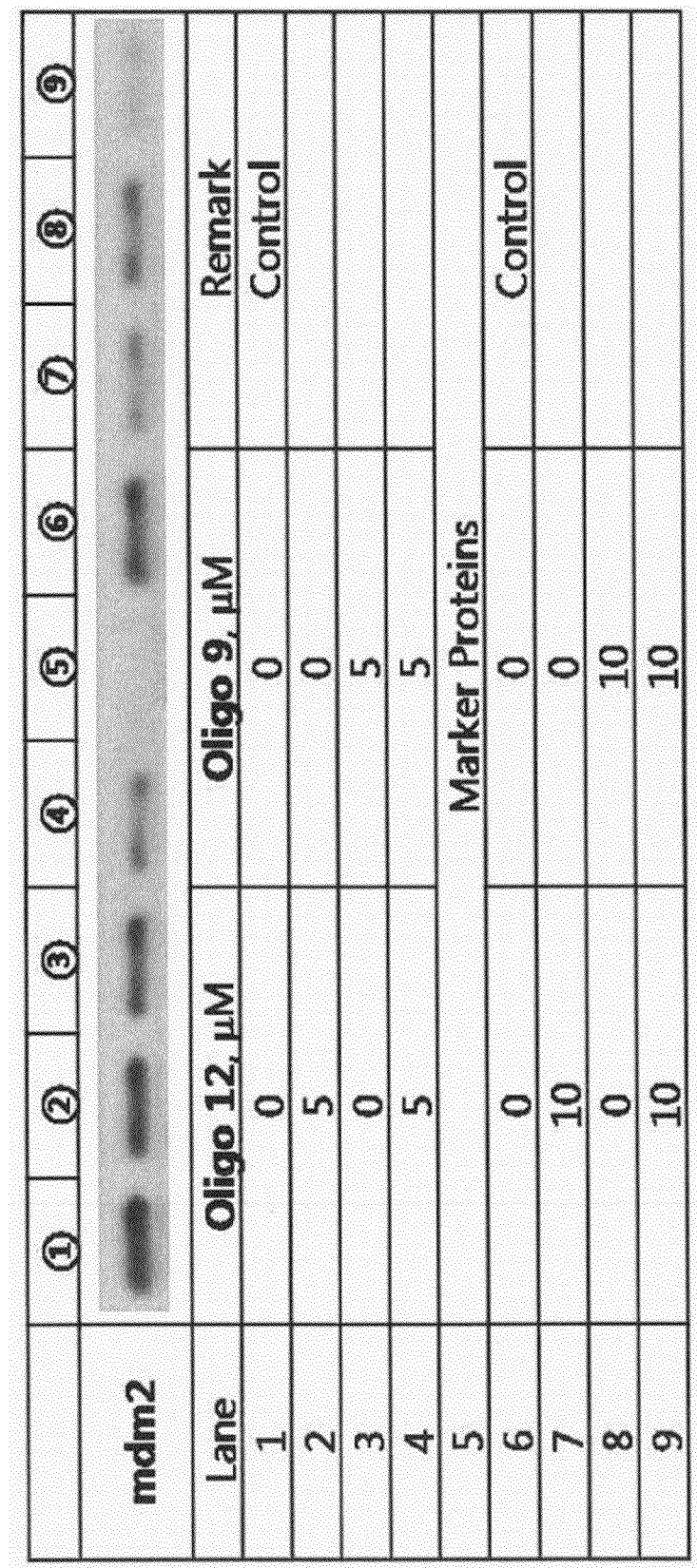

FIG. 9 provides western blotting results for JAR cells treated with 5 µM or 10 µM Oligo 9, 5 µM or 10 µM Oligo 10, cotreatment with the oligomers at 5 µM or 10 µM each, and blank (no oligomer treatment).

Figure 10:
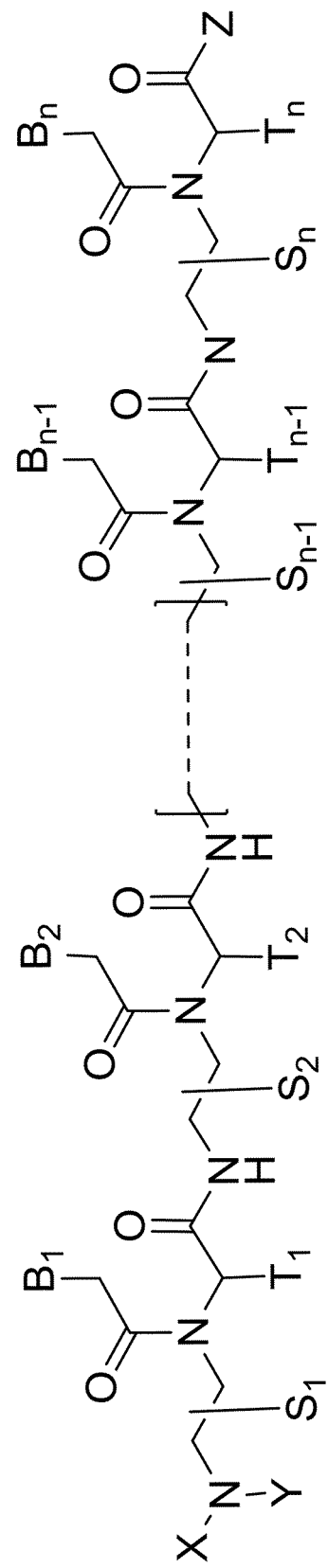

FIG. 10 is the representative structure for the PNA oligomers of this invention.

BACKGROUND OF THE INVENTION

Oligonucleotides have been used for diverse biological purposes including antisense inhibition of gene expression, PCR (polymerase chain reaction), diagnostic analysis by gene chips, and so on. Since oligonucleotides interact in a sequence specific manner with nucleic acids such as DNA and RNA, they are quite useful to predictably modulate biological processes involving DNA or RNA within cell. Unlike small molecule drugs, however, oligonucleotides do not readily penetrate mammalian cell membrane, and therefore hardly affect biological processes within cell unless properly modified or formulated to readily penetrate plasma membrane.

Proteins as Drug Targets:

Proteins mediate diverse cellular functions. It would not be surprising to find that most of currently marketed drugs show therapeutic activity through modulating functions of protein(s). For example, non-steroidal anti-inflammatory drug aspirin inhibits enzymes called cyclooxygenases for its anti-inflammatory activity. Losartan binds to and antagonize the function of a trans-membrane receptor called angiotensin II receptor for its antihypertensive activity. Rosiglitazone selectively activates an intracellular receptor called peroxisome proliferator-activated receptor γ (PPARγ) to elicit its antidiabetic activity. Etanercept is a fusion protein which binds to a cytokine called tumor necrosis factor-α (TNF-α), and neutralizes the biological activity of TNF-α for its anti-rheumatic activity. Herceptin is a monoclonal antibody to treat breast cancer by selectively binding to erbB2 over-expressed in certain types of breast cancer cells.

Antisense Inhibition of Protein Synthesis:

Proteins are encoded by DNA (2-deoxyribose nucleic acid). In response to cellular stimulation, DNA is transcribed to produce pre-mRNA (pre-messenger ribonucleic acid) in the nucleus. The intron portion(s) of pre-mRNA is enzymatically spliced out yielding mRNA (messenger ribonucleic acid), which is then translocated to the cytosolic compartment. In the cytosol, a complex of translational machinery called ribosome binds to mRNA and carries out the protein synthesis as it scans the genetic information encoded along the mRNA. (*Biochemistry* vol 41, 4503-4510, 2002; *Cancer Res.* vol 48, 2659-2668, 1988)

An oligonucleotide binding to mRNA or pre-mRNA in a sequence specific manner is called antisense oligonucleotide (AO). AO may tightly bind to an mRNA and inhibit the protein synthesis by ribosome along the mRNA in the cytosol. AO needs to be present within cell in order to inhibit the synthesis of its target protein. AO may tightly bind to a pre-mRNA in the nucleus and affect the splicing of the pre-mRNA, producing an mRNA of altered sequence and consequently an altered protein.

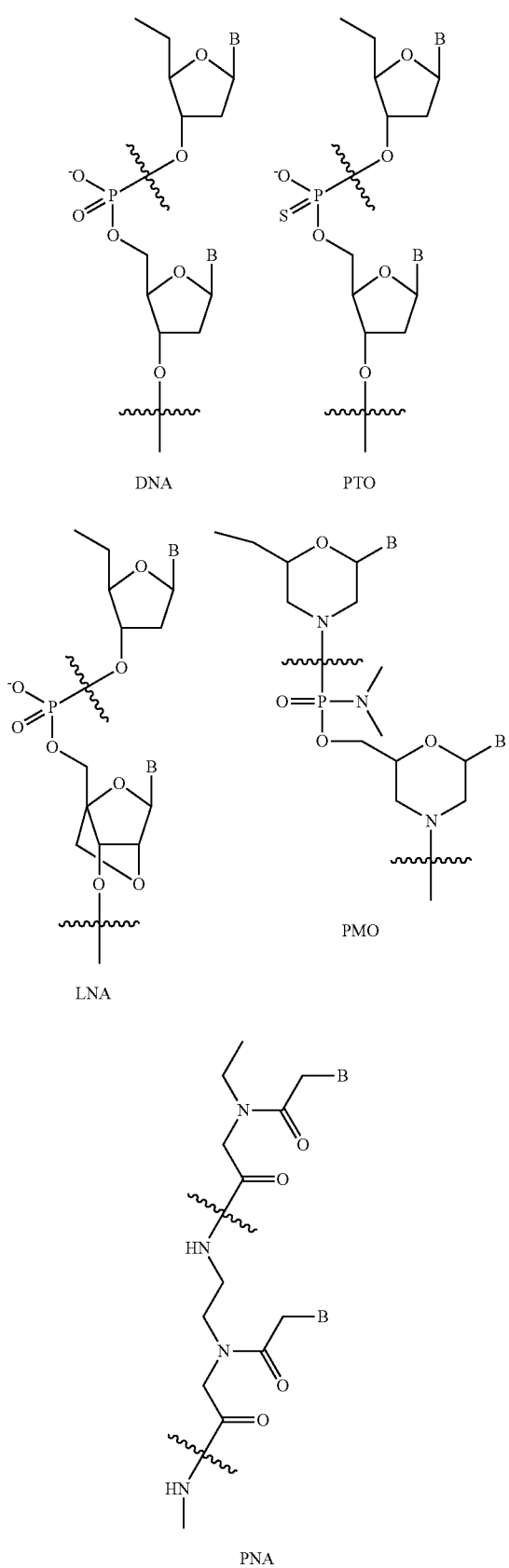

B: Nucleobase

Unnatural Oligonucleotides:

Oligonucleotides of DNA or RNA are susceptible to degradation by endogenous nucleases, limiting their therapeutic utility. To date, many types of unnatural oligonucleotides have been developed and studied intensively. (*Clin. Exp. Pharmacol. Physiol.* vol 33, 533-540, 2006) Some of them show extended metabolic stability compared to DNA and RNA. Provided above are chemical structures for some of representative unnatural oligonucleotides. Such oligonucleotides predictably bind to a complementary nucleic acid as DNA or RNA does.

Phosphorothioate oligonucleotide (PTO) is a DNA analog with one of the backbone phosphate oxygen atoms replaced with sulfur atom per monomer. Such a small structural change made PTO comparatively resistant to degradation by nucleases. (*Ann. Rev. Biochem.* vol 54, 367-402, 1985)

Reflecting the structural similarity of PTO and DNA, they both poorly penetrate cell membrane in most mammalian cell types. For some types of cells abundantly expressing transporter(s) for DNA, however, DNA and PTO show good cell penetration. Systemically administered PTOs are known to readily distribute to the liver and kidney. (*Nucleic Acids Res.* vol 25, 3290-3296, 1997)

In order to facilitate PTO's cell penetration in vitro, lipofection has been popularly practiced. However, lipofection physically alters cell membrane, causes cytotoxicity, and therefore would not be ideal for long term therapeutic use.

Over the past 20 years, antisense PTOs and variants of PTOs have been clinically evaluated to treat cancers, immunological disorders, metabolic diseases, and so on. (*Biochemistry* vol 41, 4503-4510, 2002; *Clin. Exp. Pharmacol. Physiol.* vol 33, 533-540, 2006) Many of such antisense drug candidates have not been successful partly due to PTO's poor cell penetration. In order to overcome the poor cell penetration, PTO needs to be administered at high dose for therapeutic activity. However, PTOs are known to be associated with dose dependent toxicities such as increased coagulation time, complement activation, tubular nephropathy, Kupffer cell activation, and immune stimulation including splenomegaly, lymphoid hyperplasia, mononuclear cell infiltration. (*Clin. Exp. Pharmacol. Physiol.* vol 33, 533-540, 2006)

Many antisense PTOs have been found to show due clinical activity for diseases with a significant contribution from the liver or kidney. ISIS-301012 (mipomersen) is a PTO analog which inhibits the synthesis of apoB-100, a protein involved in LDL cholesterol transport. Mipomersen manifested due clinical activity in a certain population of atherosclerosis patients most likely due to its preferential distribution to the liver. (www.medscape.com/viewarticle/556073: Accessed on Feb. 19, 2009) ISIS-113715 is an antisense PTO analog inhibiting the synthesis protein tyrosine phosphatase 1B (PTP1B), and was found to show therapeutic activity in type II diabetes patients. (*Curr. Opin. Mol. Ther.* vol 6, 331-336, 2004)

In phosphoroamidite morpholino oligonucleotide (PMO), the backbone phosphate and 2-deoxyribose of DNA are replaced with phosphoamidite and morpholine, respectively. (*Appl. Microbiol. Biotechnol.* vol 71, 575-586, 2006) While the DNA backbone is negatively charged, the PMO backbone is not charged. Thus the binding between PMO and mRNA is free of electrostatic repulsion between the backbones, and tends to be stronger than that between DNA and mRNA. Since PMO is structurally very different from DNA, PMO wouldn't be recognized by the hepatic transporter(s) recognizing DNA. However, PMO doesn't readily penetrate cell membrane.

Peptide nucleic acid (PNA) is a polypeptide with N-(2-aminoethyl)glycine as the unit backbone, and was discovered by Nielsen and colleagues. (*Science* vol 254, 1497-1500, 1991) Like DNA and RNA, PNA also selectively binds to complementary nucleic acid [*Nature* (*London*) vol 365, 566-568, 1992] Like PMO, the backbone of PNA is not charged. Thus the binding between PNA and RNA tends to be stronger than that between DNA and RNA. Since PNA is structurally markedly different from DNA, PNA wouldn't be recognized by the hepatic transporter(s) recognizing DNA, and would show a tissue distribution profile very different from that of DNA or PTO. However, PNA also poorly penetrates mammalian cell membrane. (*Adv. Drug Delivery Rev.* vol 55, 267-280, 2003)

In locked nucleic acid (LNA), the backbone ribose ring of RNA is structurally constrained to increase the binding affinity for RNA or DNA. Thus, LNAs may be regarded as high affinity DNA or RNA derivatives. (*Biochemistry* vol 45, 7347-7355, 2006)

Antisense Mechanisms:

Antisense mechanism differs depending on types of AOs. RNAse H recognizes a duplex of mRNA with DNA, RNA, or PTO, and degrades the duplex portion of mRNA. Thus, the antisense activity of PTO is significantly amplified by RNAse H. In the meantime, RNAse H does not recognize a duplex of mRNA with PMO, PNA, or LNA. In other words, PMO, PNA and LNA must rely purely on the steric blocking of mRNA for their antisense activity. (*Biochemistry* vol 41, 4501-4510, 2002)

For oligonucleotides with the same binding affinity for mRNA, PTO should therefore show stronger antisense activity than PMO, PNA, and LNA. For steric block AOs such as PMO, PNA, and LNA, strong affinity for mRNA is desired for antisense activity.

Antisense Activity of PNA:

The binding affinity of PNA for mRNA would increase as the length of PNA increases to a certain point. However, the antisense activity of PNA doesn't seem to always increase to the length of PNA. There were cases that the antisense activity of PNA reached the maximum activity at 12 to 13-mer and decreases thereafter. (*Nucleic acids Res.* vol 32, 4893-4902, 2004) On the other hand, optimum antisense activity was reached with 15 to 18-mer PNAs against a certain mRNA, reflecting that the structural accessibility of the target binding site of the mRNA would be important. (*Biochemistry* vol 40, 53-64, 2001)

In many cases, PNAs have been reported to inhibit protein synthesis by ribosome at micromolar level under good cell penetrating conditions. (*Science* vol 258, 1481-85, 1992; *Biochemistry* vol 40, 7853-7859, 2001; *Nucleic acids Res.* vol 32, 4893-4902, 2004) However, PNAs targeting a highly accessible position of mRNA were found to show antisense activity at sub-micromolar level (*Neuropeptides* vol 38, 316-324, 2004; *Biochemistry* vol 40, 53-64, 2001) or even at sub-nanomolar level (*Nucleic Acids Res.* vol 36, 4424-4432, 2008) under good transfection conditions.

In addition to targeting a highly accessible site in mRNA, strong binding affinity of PNA for mRNA would be very required for good antisense activity. Unlike DNA, PTO, and LNA, the backbone of PNA is not charged. PNA tends to aggregate and become less suitable for binding to mRNA as its size increases. It is desired to improve PNA's binding affinity for mRNA without increasing the length of PNA. Incorporation of PNA monomers with a point charge would be beneficial in preventing PNA from aggregating.

Cell Penetration Strategies for PNA:

PNAs do not readily penetrate cell membrane and tend to show poor antisense activity unless properly transfected. In early years, the antisense activity of PNA was assessed by microinjection (*Science* vol 258, 1481-85, 1992) or electroporation (*Biochemistry* vol 40, 7853-7859, 2001). Microinjection and electroporation are invasive and inappropriate to be applied for therapeutic purposes. In order to improve the cell penetration, various strategies have been developed. (*Adv. Drug Delivery Rev.* vol 55, 267-280, 2003; *Curr. Top. Med. Chem.* vol 7, 727-737, 2007)

PNAs have been effectively delivered into cell by covalent incorporation of cell penetrating peptides (*Neuropeptides* vol 38, 316-324, 2004), lipofection following duplex formation with a complementary DNA (*Biochemistry* vol 40, 53-64, 2001), lipofection of PNAs with a covalently attached 9-aminoacridine (*Nucleic Acids Res.* vol 32, 2695-2706, 2004), lipofection of PNAs with covalently attached phosphonate anions (*Nucleic Acids Res.* vol 36, 4424-4432, 2008), and so on. Also cell penetration was improved by attaching to PNA a lipophilc moiety such as adamantane (*Bioconjugate Chem.* vol 10, 965-972, 1999) or amphiphilic group such as tetraphenyl phosphonium. (*Nucleic Acids Res.* vol 29, 1852-1863, 2001) Nevertheless, such a covalent modification is unlikely to increase the binding affinity for mRNA despite marked improvement in the cell penetration.

PNAs with a Covalently Attached CPP:

Cell penetrating peptides (CPPs) are polypeptides showing good cell penetration, and have multiple positive charges from arginine or lysine residues. To date many CPPs such as transportan, penetratin, NLS (nuclear localization signal), and Tat have been discovered. CPPs are known to efficiently carry a covalently attached cargo into cell. PNAs with a covalently attached CPP also showed good cell penetration.

Although some PNAs with a covalently attached CPP showed antisense $IC_{50}$s around 100 nM (*Neuropeptides* vol 38, 316-324, 2004), micromolar antisense $IC_{50}$s are rather prevalent for such PNAs.

PNAs with a covalently linked CPP are composed of two portions, the hydrophobic PNA domain and the positively charged CPP domain. Such a PNA tends to aggregate and be trapped in endosomes within cell, and would not be available for the antisense inhibition of protein synthesis. (*Curr. Top. Med. Chem.* vol 7, 727-737, 2007; *Nucleic Acids Res.* vol 33, 6837-6849, 2005) Furthermore, such a covalently attached CPP hardly increases the binding affinity of PNA for mRNA.

PNAs with a Chiral Backbone:

There have been attempts to introduce a chiral substituent on the PNA backbone of 2-aminoethyl-glycine (Aeg). For example, the aqueous solubility of PNA was significantly improved by incorporating PNA monomer(s) with a backbone of 2-aminoethyl-lysine in place of Aeg. (*Angew. Chem. Int. Ed. Engl.* vol 35, 1939-1941, 1996)

By introducing the backbone of L-(2-amino-2-methyl) ethyl-glycine in place of Aeg, the binding affinity of PNA for DNA and RNA was significantly improved. A 10-mer PNA with all of the backbone of L-(2-amino-2-methyl)ethyl-glycine in place of 2-aminoethyl-glycine showed an increase of 19° C. and 10° C. in $T_m$ against complementary DNA and RNA, respectively. Such an increase doesn't seem to be proportional to the number of substitution with L-(2-amino-2-methyl)ethyl-glycine, though. (*J. Am. Chem. Soc.* vol 128, 10258-10267, 2006)

GPNA:

The cell penetration of PNA was reported to be markedly improved by incorporating PNA monomers with a backbone of 2-aminoethyl-arginine in place of Aeg. (*J. Am. Chem. Soc.* vol 125, 6878-6879, 2003) Such PNAs have been termed 'GPNA' since they have guanidinium moiety on the backbone.

GPNAs with the backbone of 2-aminoethyl-D-arginine were reported to have stronger affinity for DNA and RNA than the corresponding GPNAs with that of 2-aminoethyl-L-arginine. (*Chem. Commun.* 244-246, 2005) For a 10-mer GPNA with 5 GPNA monomers with the backbone of 2-aminoethyl-D-arginine there was an increase of 7° C. in $T_m$ (melting temperature) against complementary DNA compared to the corresponding unmodified PNA. (*Bioorg. Med. Chem. Lett.* vol 16, 4931-4935, 2006)

A 16-mer antisense GPNA against human EGFR-TK was reported to show antitumor activity upon ip (intra peritoneal) administration in athymic nude mice, although the in vitro antisense activity was not documented for the antisense GPNA in the prior art. (WO 2008/061091)

PNAs with Modified Nucleobase:

Like cases with DNA, nucleobase modifications have been pursued to improve PNA's affinity for nucleic acids.

PNAs with adenine replaced with 2,6-diaminopurine were evaluated for their affinity for complementary DNA or RNA. Substitution with 2,6-diaminopurine was found to elicit an increase of 2.5~6° C. in $T_m$ per replacement. (*Nucleic Acids Res.* vol 25, 4639-4643, 1997)

Cytosine and Modified Cytosines

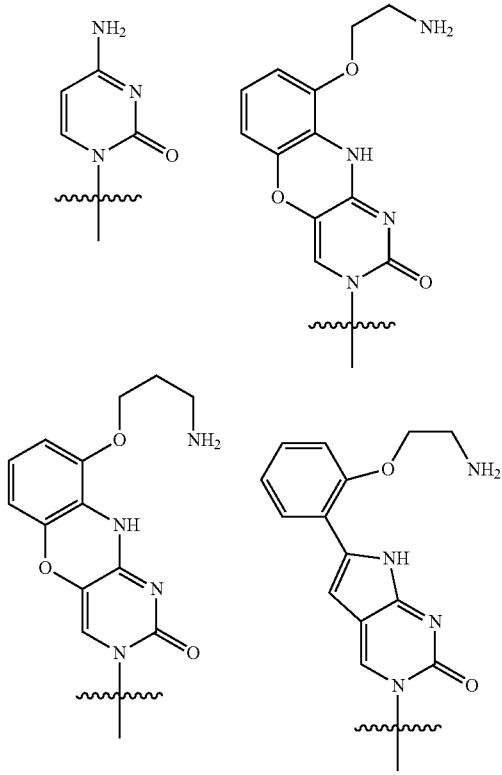

PNAs with cytosine replaced with 9-(2-aminoethoxy)phenoxazine were evaluated for their affinity for complementary DNA or RNA. A single substitution with 9-(2-aminoethoxy) phenoxazine elicited an increase of 10.7~23.7° C. in $T_m$, although such an increase was markedly dependent on the nucleotide sequence. Nucleobase 9-(2-aminopropoxy)phenoxazine also induced a large increase in $T_m$. Due to a huge increase in $T_m$, PNA monomer with either 9-(2-aminoethoxy)-phenoxazine or 9-(2-aminopropoxy)phenoxazine as a cytosine replacement has been termed 'G-clamp'. (*Org. Lett.* vol 4, 4395-4398, 2002) However, cell penetration data was not reported for PNAs with G-clamp(s).

PNAs with cytosine replaced with either 6-{2-(2-aminoethoxy)phenyl}-pyrrolocytosine or 6-{2,6-di(2-aminoethoxy)phenyl}pyrrolocytosine were evaluated for their affinity for complementary DNA or RNA. A single substitution with either 6-{2-(2-aminoethoxy)phenyl}pyrrolocytosine or 6-{2,6-di(2-aminoethoxy)-phenyl}pyrrolocytosine increased $T_m$ by 3~11.5° C. (*J. Am. Chem. Soc.* vol 130, 12574-12575, 2008) However, such PNAs were not evaluated for cell penetration.

Other Use of PNAs:

By tightly binding to a microRNA, PNA can inhibit the regulatory function of the microRNA, leading to an increase in the expression level of the protein(s) directly regulated by the microRNA. (*RNA* vol 14, 336-346, 2008) By tightly binding to a ribonucleoprotein such as telomerase, PNA can modulate the cellular function of the ribonucleoprotein. (*Bioorg. Med. Chem. Lett.* vol 9, 1273-78, 1999) By tightly binding to a certain portion of a gene in the nucleus, PNA can modulate the transcription level of the gene. (*Biochemistry* vol 46, 7581-89, 2007)

Since PNA tightly binds to DNA and RNA, and sensitively discriminates a single base pair mismatch, PNA would be suitable for high fidelity detection of single nucleotide polymorphism (SNP). Since PNA binds tightly to DNA and RNA with high sequence specificity, PNA may find various other therapeutic and diagnostic applications involving DNA or RNA. (*FASEB* vol 14, 1041-1060, 2000)

SUMMARY OF INVENTION

The present invention provides a novel class of PNA oligomers represented by Formula I, or a pharmaceutically acceptable salt thereof:

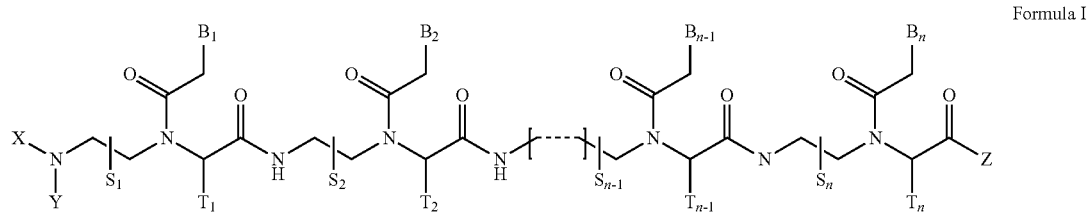

Formula I wherein, n is an integer equal to or larger than 5;

$S_1, S_2, \ldots, S_{n-1}, S_n, T_1, T_2, \ldots, T_{n-1}$, and $T_n$ independently represent hydrido, deuterido, substituted or non-substituted alkyl, or substituted or non-substituted aryl radical;

X and Y independently represent hydrido, deuterido, hydroxy, substituted or non-substituted alkyloxy, substituted or non-substituted aryloxy, substituted or non-substituted amino, substituted or non-substituted alkyl, substituted or non-substituted acyl, substituted or non-substituted sulfonyl, or substituted or non-substituted aryl radical;

Z represents hydrido, deuterido, hydroxy, substituted or non-substituted alkyloxy, substituted or non-substituted aryloxy, substituted or non-substituted amino, substituted or non-substituted alkyl, or substituted or non-substituted aryl radical;

$B_1, B_2, \ldots, B_{n-1}$, and $B_n$ are independently selected from natural nucleobases including adenine, thymine, guanine, cytosine and uracil, and unnatural nucleobases; and, at least one of $B_1, B_2, \ldots, B_{n-1}$, and $B_n$ independently represents an unnatural nucleobase with a substituted or non-substituted amino radical covalently linked to the moiety responsible for its due nucleobase pairing properties.

A PNA oligomer of Formula I shows improved binding affinity for nucleic acid and cell penetration compared to its corresponding 'unmodified' PNA oligomer. PNA oligomers of this invention are useful to sequence specifically inhibit or modulate cellular and physiological functions mediated by nucleic acids or physiologically active molecules having a nucleic acid domain such as ribonucleoproteins. Also PNA oligomers of this invention are useful for diagnostic purposes due to their sequence specific binding capability for nucleic acids.

DESCRIPTION OF INVENTION

The present invention provides a novel class of PNA oligomers represented by Formula I, or a pharmaceutically acceptable salt thereof:

at least one of $B_1, B_2, \ldots, B_{n-1}$, and $B_n$ independently represents an unnatural nucleobase with a substituted or non-substituted amino radical covalently linked to the moiety responsible for its due nucleobase pairing properties.

A PNA oligomer of this invention shows improved cell penetration and binding to nucleic acid compared to its corresponding 'unmodified' PNA oligomer. In this invention, 'unmodified' PNA oligomer refers to a PNA oligomer of Formula I, wherein $S_1, S_2, \ldots, S_{n-1}, S_n, T_1, T_2, \ldots, T_{n-1}$, and $T_n$ are hydrido radical; and $B_1, B_2, \ldots, B_{n-1}$, and $B_n$ are independently selected from natural nucleobases comprising adenine, thymine, guanine, and cytosine.

A PNA oligomer of this invention readily penetrates mammalian cell membrane, and can affect or alter cellular functions by sequence specifically binding to a nucleic acid or a nucleoprotein within cell.

A PNA oligomer of Formula I can potently inhibit ribosomal protein synthesis by tightly binding to mRNA. A PNA oligomer of the present invention can tightly bind to a pre-mRNA and alter the splicing of the pre-mRNA to mRNA. Further, a PNA oligomer of the present invention can bind tightly to a microRNA, and inhibit mRNA degradation induced by the microRNA.

A PNA oligomer of Formula I can predictably bind to the nucleic acid domain of a ribonucleoprotein, for example telomerase, and modulate its physiological function(s). A PNA oligomer of the present invention can bind to a gene and modulate the transcription of the gene. A PNA oligomer of Formula I can bind to a viral gene or its transcript, and inhibit the proliferation of the virus. A PNA oligomer of this invention can affect cellular functions other than those described above by sequence specifically binding to a nucleic acid or a nucleoprotein within mammalian cell. In addition, a PNA oligomer of the present invention can tightly bind to a bacterial mRNA, nucleic acid, or gene, and inhibit bacterial proliferation or alter bacterial biosynthesis profiles.

A PNA oligomer of this invention is highly sensitive to a base mismatch in binding to its complementary DNA counterpart, and would be appropriate for detecting single nucle-

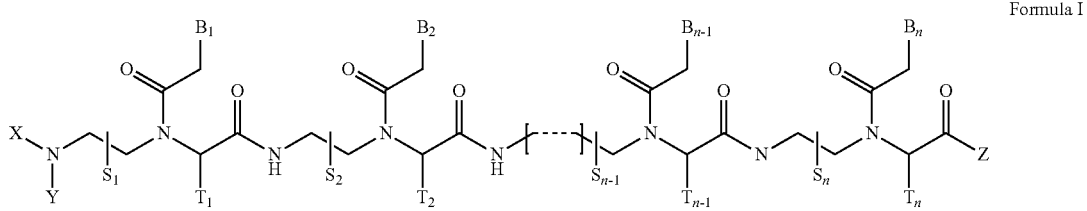

Formula I wherein, n is an integer equal to or larger than 5;

$S_1, S_2, \ldots, S_{n-1}, S_n, T_1, T_2, \ldots, T_{n-1}$, and $T_n$ independently represent hydrido, deuterido, substituted or non-substituted alkyl, or substituted or non-substituted aryl radical;

X and Y independently represent hydrido, deuterido, hydroxy, substituted or non-substituted alkyloxy, substituted or non-substituted aryloxy, substituted or non-substituted amino, substituted or non-substituted alkyl, substituted or non-substituted acyl, substituted or non-substituted sulfonyl, or substituted or non-substituted aryl radical;

Z represents hydrido, deuterido, hydroxy, substituted or non-substituted alkyloxy, substituted or non-substituted aryloxy, substituted or non-substituted amino, substituted or non-substituted alkyl, or substituted or non-substituted aryl radical;

$B_1, B_2, \ldots, B_{n-1}$, and $B_n$ are independently selected from natural nucleobases including adenine, thymine, guanine, cytosine and uracil, and unnatural nucleobases; and, otide polymorphism (SNP) with high fidelity. PNA oligomers of the present invention bind tightly to their complementary DNAs with high sequence specificity, and may be useful for gene profiling. A PNA oligomer of Formula I may be useful to probe or locate a nucleic acid bearing molecule such as telomere within cell if properly tagged with a chromophore, for example, fluorophore. PNA oligomers of this invention may be useful for a variety of diagnostic or analytical purposes other than those detailed above.

A PNA oligomer of the present invention possesses good aqueous solubility compared to the corresponding 'unmodified' PNA oligomer, and can be used as dissolved in water, saline, or a buffer solution. A PNA oligomer of Formula I can be formulated with a cationic lipid such as lipofectamine. A PNA oligomer of this invention may be duplexed with a complementary DNA and the resulting duplex can be formulated with a cationic lipid.

A PNA oligomer of this invention may be formulated in a variety of dosage forms including but not limited to injectable formulation, nasal spray, tablet, granules, hard capsule, soft capsule, liposomal formulation, oral suspension, transdermal formulation, and so on.

A PNA oligomer of the present invention can be administered to a subject at therapeutically effective doses, which would vary depending on indication, administration route, dosing schedule, situations of subject, and so on.

A PNA oligomer of the present invention can be administered to a subject by a variety of routes including but not limited to intravenous injection, subcutaneous injection, intraperitoneal injection, nasal inhalation, oral administration, transdermal application, and so on.

A PNA oligomer of Formula I can be administered to a subject in combination with a pharmaceutically acceptable adjuvant including but not limited to citric acid, hydrochloric acid, tartaric acid, stearic acid, polyethyleneglycol, polypropyleneglycol, ethanol, sodium bicarbonate, distilled water, hyaluronic acid, cationic lipid such as lipofectamine, starch, gelatin, talc, ascorbic acid, olive oil, palm oil, methylcelluose, titanium oxide, sodium carboxymethylcellulose, sweetener, preservative, and so on.

A PNA oligomer of the present invention, depending on the presence of basic or acidic functional group(s) therein, may be used as neutralized with an equivalent amount of a pharmaceutically acceptable acid or base including but not limited to sodium hydroxide, potassium hydroxide, hydrochloric acid, methanesulfonic acid, citric acid, and so on.

Preferred PNA oligomers encompass PNA oligomers of Formula I, or a pharmaceutically acceptable salt thereof:
wherein,
n is an integer equal to or larger than 5 but smaller than or equal to 30;
$S_1, S_2, \ldots, S_{n-1}, S_n, T_1, T_2, \ldots, T_{n-1}$, and $T_n$ are hydrido radical;
X and Y are independently selected from hydrido, substituted or non-substituted alkyl, substituted or non-substituted acyl, substituted or non-substituted sulfonyl, and substituted or non-substituted aryl radical;
Z represents hydrido, hydroxy, substituted or nonsubstituted alkyloxy, substituted or non-substituted amino, substituted or non-substituted alkyl, or substituted or non-substituted aryl radical;
$B_1, B_2, \ldots, B_{n-1}$, and $B_n$ are independently selected from natural nucleobases including adenine, thymine, guanine, cytosine and uracil, and unnatural nucleobases; and,
at least one of $B_1, B_2, \ldots, B_{n-1}$, and $B_n$ is independently selected from unnatural nucleobases represented by Formula II, Formula III, or Formula IV:

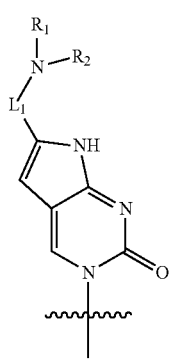

Formula II

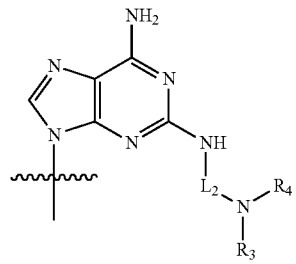

Formula III

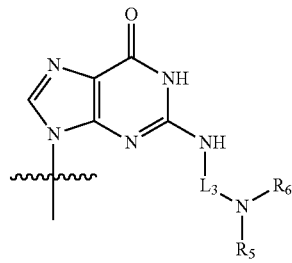

Formula IV wherein,
$R_1, R_2, R_3, R_4, R_5$ and $R_6$ are independently selected from substituted or non-substituted alkyl, hydrido, hydroxy, and substituted or non-substituted alkyloxy radical; and,
$L_1, L_2$ and $L_3$ are a covalent linker represented by Formula V connecting a basic amino group to the moiety responsible for nucleobase pairing properties:

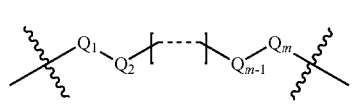

Formula V wherein,
$Q_1$ and $Q_m$ are substituted or non-substituted methylene (—CH$_2$—) radical, and $Q_m$ is directly linked to the basic amino group;
$Q_2, Q_3, \ldots$, and $Q_{m-1}$ are independently selected from substituted or non-substituted methylene, oxygen (—O—), sulfur (—S—), and substituted or non-substituted amino radical [—N(H)—, or —N(substituent)-]; and, m is an integer equal to or larger than 2 but smaller than or equal to 15.

PNA oligomers of particular interest comprise PNA oligomers of Formula I, or a pharmaceutically acceptable salt thereof:
wherein,
n is an integer equal to or larger than 8 but smaller than or equal to 25;
$S_1, S_2, \ldots, S_{n-1}, S_n, T_1, T_2, \ldots, T_{n-1}$, and $T_n$ are hydrido radical;
X and Y are independently selected from hydrido, substituted or non-substituted alkyl, and substituted or non-substituted acyl radical;
Z represents hydroxy, or substituted or non-substituted amino radical;
$B_1, B_2, \ldots, B_{n-1}$, and $B_n$ are independently selected from natural nucleobases including adenine, thymine, guanine, cytosine and uracil, and unnatural nucleobases;
at least two of $B_1, B_2, \ldots, B_{n-1}$, and $B_n$ are independently selected from unnatural nucleobases represented by Formula II, Formula III, or Formula IV;

$R_1$, $R_2$, $R_3$, $R_4$, $R_5$ and $R_6$ are independently selected from substituted or non-substituted alkyl, and hydrido radical;

$Q_1$ and $Q_m$ are substituted or non-substituted methylene radical, and $Q_m$ is directly linked to the basic amino group;

$Q_2$, $Q_3$, ..., and $Q_{m-1}$ are independently selected from substituted or non-substituted methylene, oxygen, and amino radical; and, m is an integer equal to or larger than 2 but smaller than or equal to 12.

PNA oligomers of high interest comprise PNA oligomers of Formula I, or a pharmaceutically acceptable salt thereof:
wherein,
n is an integer equal to or larger than 10 but smaller than or equal to 25;

$S_1$, $S_2$, ..., $S_{n-1}$, $S_n$, $T_1$, $T_2$, ..., $T_{n-1}$, and $T_n$ are hydrido radical;

X and Y are independently selected from hydrido, and substituted or non-substituted acyl radical;

Z represents hydroxy, alkyloxy, or substituted or non-substituted amino radical; and, $B_1$, $B_2$, ..., $B_{n-1}$, and $B_n$ are independently selected from natural nucleobases including adenine, thymine, guanine, cytosine and uracil, and unnatural nucleobases;

at least three of $B_1$, $B_2$, ..., $B_{n-1}$, and $B_n$ are independently selected from unnatural nucleobases represented by Formula II, Formula III, or Formula IV;

$R_1$, $R_2$, $R_3$, $R_4$, $R_5$ and $R_6$ are independently selected from substituted or non-substituted alkyl, and hydrido radical;

$Q_1$ and $Q_m$ are methylene radical, and $Q_m$ is directly linked to the basic amino group;

$Q_2$, $Q_3$, ..., and $Q_{m-1}$ are independently selected from methylene, oxygen, and amino radical; and, m is an integer equal to or larger than 2 but smaller than or equal to 10.

PNA oligomers of higher interest encompass PNA oligomers of Formula I, or a pharmaceutically acceptable salt thereof:
wherein,
n is an integer equal to or larger than 10 but smaller than or equal to 20;

$S_1$, $S_2$, ..., $S_{n-1}$, $S_n$, $T_1$, $T_2$, ..., $T_{n-1}$, and $T_n$ are hydrido radical;

X and Y are independently selected from hydrido, and substituted or non-substituted acyl radical;

Z represents hydroxy, or substituted or non-substituted amino radical;

$B_1$, $B_2$, ..., $B_{n-1}$, and $B_n$ is independently selected from natural nucleobases including adenine, thymine, guanine, cytosine and uracil, and unnatural nucleobases;

at least three of $B_1$, $B_2$, ..., $B_{n-1}$, and $B_n$ are independently selected from unnatural nucleobases represented by Formula II, Formula III, or Formula IV;

$R_1$, $R_3$, and $R_5$ are hydrido radical, and $R_2$, $R_4$, and $R_6$ independently represent hydrido, or substituted or non-substituted amidinyl radical;

$Q_1$ and $Q_m$ are methylene radical, and $Q_m$ is directly linked to the basic amino group;

$Q_2$, $Q_3$, ..., and $Q_{m-1}$ are independently selected from methylene, oxygen, and amino radical; and, m is an integer equal to or larger than 2 but smaller than or equal to 10.

PNA oligomers of highest interest comprise PNA oligomers of Formula I, or a pharmaceutically acceptable salt thereof:
wherein,
n is an integer equal to or larger than 10 but smaller than or equal to 20;

$S_1$, $S_2$, ..., $S_{n-1}$, $S_n$, $T_1$, $T_2$, ..., $T_{n-1}$, and $T_n$ are hydrido radical;

X and Y are independently selected from hydrido, and substituted or non-substituted acyl radical;

Z represents hydroxy, or substituted or non-substituted amino radical;

$B_1$, $B_2$, ..., $B_{n-1}$, and $B_n$ are independently selected from adenine, thymine, guanine, cytosine, and unnatural nucleobases;

at least three of $B_1$, $B_2$, ..., $B_{n-1}$, and $B_n$ are independently selected from unnatural nucleobases represented by Formula II, Formula III, or Formula IV;

$R_1$, $R_3$, and $R_5$ are hydrido radical, and $R_2$, $R_4$, and $R_6$ independently represents hydrido or amidinyl radical;

$Q_1$ and $Q_m$ are methylene radical, and $Q_m$ is directly linked to the basic amino group;

$Q_2$, $Q_3$, ..., and $Q_{m-1}$ are independently selected from methylene, and oxygen radical; and, m is an integer equal to or larger than 2 but smaller than or equal to 8.

Specific PNA oligomers of strong interest comprise PNA oligomers of Formula I, or a pharmaceutically acceptable salt thereof:
wherein,
n is an integer equal to or larger than 8 but smaller than or equal to 20;

$S_1$, $S_2$, ..., $S_{n-1}$, $S_n$, $T_1$, $T_2$, ..., $T_{n-1}$, and $T_n$ are hydrido radical;

X is hydrido radical;

Y represents hydrido, or substituted or non-substituted acyl radical;

Z represents hydroxy, or substituted or non-substituted amino radical;

$B_1$, $B_2$, ..., $B_{n-1}$, and $B_n$ are independently selected from adenine, thymine, guanine, cytosine, and unnatural nucleobases;

at least three of $B_1$, $B_2$, ..., $B_{n-1}$, and $B_n$ are independently selected from unnatural nucleobases represented by Formula II, Formula III, or Formula IV;

$R_1$, $R_3$, and $R_5$ are hydrido radical, and $R_2$, $R_4$, and $R_6$ independently represent hydrido or amidinyl radical;

$L_1$ represents —(CH$_2$)$_2$—O—(CH$_2$)$_2$—, —CH$_2$—O—(CH$_2$)$_2$—, or —CH$_2$—O—(CH$_2$)$_3$— with the right end is directly linked to the basic amino group; and, $L_2$ and $L_3$ are independently selected from —(CH$_2$)$_2$—O—(CH$_2$)$_2$—, —(CH$_2$)$_3$—O—(CH$_2$)$_2$—, —(CH$_2$)$_2$—O—(CH$_2$)$_3$—, —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, and —(CH$_2$)$_8$— with the right end is directly linked to the basic amino group.

The above used terms and abbreviations for the PNA oligomers of this invention are illustrated in the table below.

| Term/Abbreviation | Illustration or definition |
|---|---|
| oligomer | oligonucleotide |
| hydrido | single hydrogen atom (—H) |
| deuterido | single deuterium atom (—D) |
| alkyl | linear or branched alkyl radical |
| aryl | aromatic group such as phenyl, pyridyl, furyl, naphthyl, etc |
| methylene | —(CH$_2$)— |
| acyl | '—C(O)—' substituted with hydrido, alkyl, or aryl radical |
| sulfonyl | '—S(O)$_2$—' substituted with alkyl, or aryl radical |
| alkyloxy | 'R—O—' where R is substituted or non-substituted alkyl radical |
| oxygen | '—O—' |
| sulfur | '—S—' |

| Term/Abbreviation | Illustration or definition |
|---|---|
| amidinyl | ![amidinyl structure] |
| cytosine (C) | ![cytosine structure] |
| thymine (T) | ![thymine structure] |
| uracil (U) | ![uracil structure] |
| adenine (A) | ![adenine structure] |
| guanine (G) | ![guanine structure] |

General Synthetic Procedures

For characterization of molecules of this invention NMR spectra were recorded on a Varian Mercury 300 MHz, Bruker Avance 400 MHz, or Varian Inova 500 MHz NMR spectrometer. Either a Bruker Daltonics Ultraflex MALDI-TOF or an Agilent LC/MS Ion Trap System was employed for determination of molecular weight. PNA oligomers were analyzed and purified by $C_{18}$-reverse phase HPLC either on a Hewlett Packard 1050 HPLC or a Shimazu LC-6AD HPLC. Unless noted otherwise, silica gel was used for chromatographic separation of small molecules prepared in this invention. Melting point is reported as uncorrected.

Unnatural nucleobase derivatives used for the synthesis of PNA monomers of this invention were prepared according to one of the methods (Methods A, B, and C) provided below or with minor modification(s) thereof, unless detailed otherwise in actual synthetic examples.

Method A:

6-alkyl-pyrollocytosine derivatives were synthesized as properly protected according to Scheme 1 or with minor variation(s) thereof. Such 6-alkyl-pyrollocytosine derivatives were used to synthesize PNA monomers containing a nucleobase represented by Formula II as a cytosine equivalent.

First compound a was deprotonated with NaH and then alkylated with ethylbromoacetate to obtain compound b. Compound b was subjected to a palladium catalyzed coupling with a terminal acetylene derivative, which was in situ annulated to product c according to the literature. (*Nucleosides Nucleotides & Nucleic Acids* vol 22, 1029-1033, 2003)

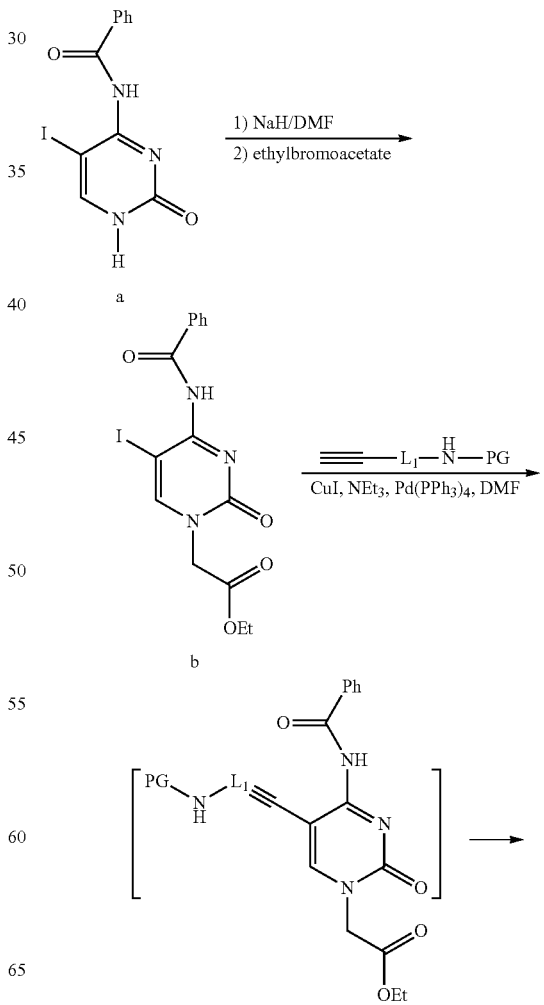

Scheme 1

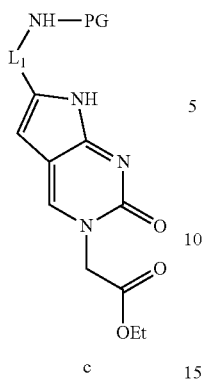

PG: Protecting Group

Method B:

2,6-diaminopurine derivatives were synthesized as properly protected according to Scheme 2 or with minor variation(s) thereof. Such 2,6-diamino-purine derivatives were used to synthesize PNA monomers containing a nucleobase represented by Formula III as an adenine equivalent.

First 2-haloadenine was reacted with a diamine at high temperature to obtain compound d, which was then reacted with Boc₂O to give compound e. Compound e was deprotonated with NaH, and alkylated with ethylbromoacetate to obtain compound f. The aromatic amino group of compound f was protected with either Cbz or Boc group to yield compound g.

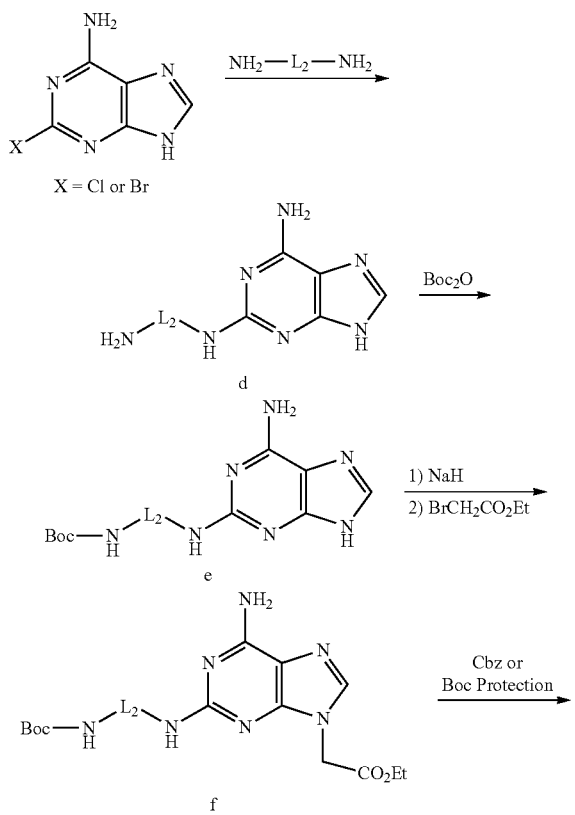

Scheme 2

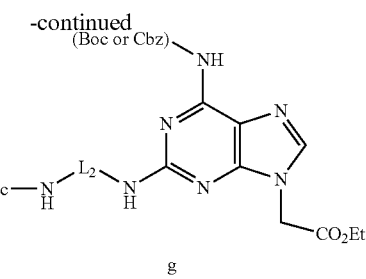

Method C:

N-alkylated guanine derivatives were synthesized as properly protected according to Scheme 3 or with minor variations thereof. Such guanine derivatives were used to synthesize PNA monomers containing a nucleobase represented by Formula IV as a guanine equivalent.

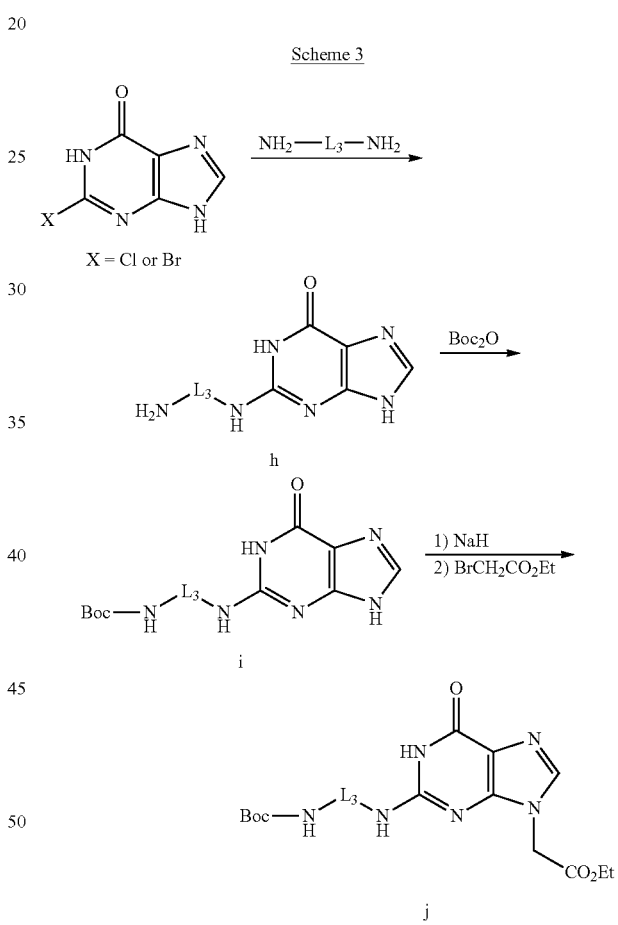

Scheme 3

First 2-halohypoxanthine was reacted with a diamine at high temperature to obtain compound h, which was then reacted with Boc₂O to give compound i. Compound i was deprotonated with NaH, and alkylated with ethylbromoacetate to obtain compound j.

Two types of PNA monomers were synthesized according to either Method D or Method E to prepare PNA oligomers of Formula I. PNA oligomers were prepared by Panagene, Inc. (www.panagene.com, Daejon, South Korea) using PNA monomers of type o of Scheme 4 upon request of CTI Bio. Alternatively, PNA monomers of type q of Scheme 5 were used in-house for the synthesis of PNA oligomers according to the method described in the prior art or with minor modification(s) thereof. (U.S. Pat. No. 6,133,444)

Method D:

PNA monomers with a modified nucleobase were prepared according to Scheme 4 or with minor variation(s) thereof as properly protected for the PNA oligomer synthesis method described in the literature. (*Org. Lett.* vol 9, 3291-3293, 2006) In Scheme 4, compound k may correspond to compound c of Scheme 1, compound g of Scheme 2, or compound j of Scheme 3, however, may not be necessarily limited to one of those ester compounds.

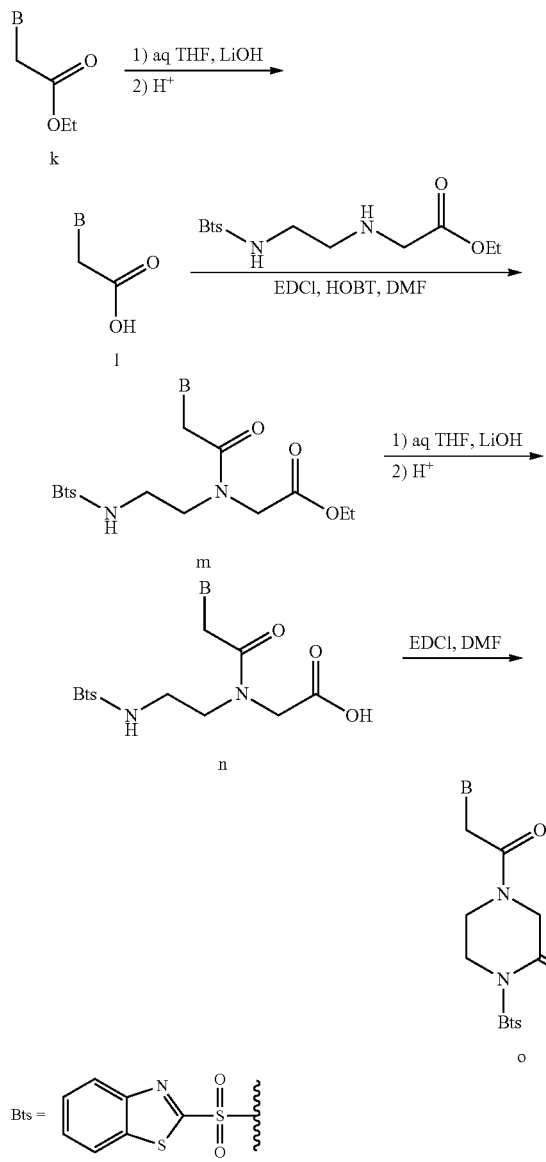

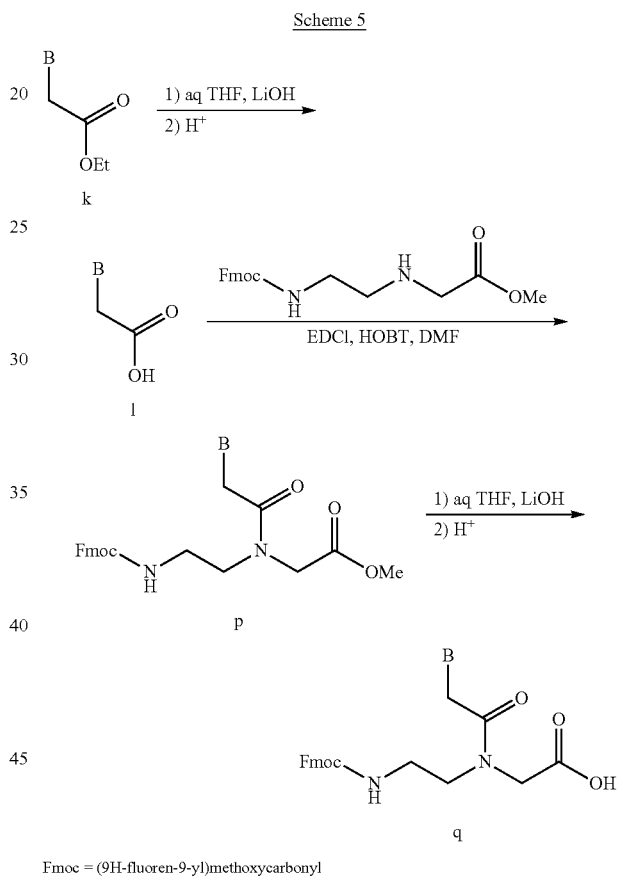

First ester k was subjected to alkaline hydrolysis to afford acid l, which was then coupled with ethyl N-[2-{N-(2-benzothiazolinyl)sulfonylamino}ethyl]-glycinate to obtain compound m. Compound m was mildly hydrolyzed with LiOH to give acid n, which was cyclized by an EDCI coupling reaction to obtain modified PNA monomer o. The chemical structure for PNA monomer o was assumed as in Scheme 4 throughout this invention, given that such assigned PNA monomers have successfully yielded PNA oligomers in the literature. (*Org. Lett.* vol 9, 3291-3293, 2006)

Method E:

Alternatively, PNA monomers with a modified nucleobase were prepared according to Scheme 5 or with minor variation(s) thereof as properly protected for the PNA oligomer synthesis method provided in the prior art. (U.S. Pat. No. 6,133,444) In Scheme 5, compound k may correspond to compound c of Scheme 1, compound g of Scheme 2, or compound j of Scheme 3, however, may not be necessarily limited to one of those ester compounds.

First acid l was coupled with ethyl N-[2-{N-(9H-fluoren-9-yl)amino}ethyl]-glycinate to obtain compound p by an EDCI coupling reaction. Then compound p was mildly hydrolyzed with LiOH to obtain PNA monomer q with a modified nucleobase.

The following examples contain detailed descriptions of the preparation methods for compounds of this invention. The detailed descriptions of these examples are presented for illustrative purposes only and should not be interpreted as a restriction to the present invention. Most of these detailed descriptions fall within the scope, and serve to exemplify the above described GENERAL SYNTHETIC PROCEDURES which form a part of the invention. The abbreviations used in the following examples are defined in the following table.

| Category | Denotation |
|---|---|
| ¹H NMR | Proton nuclear magnetic resonance. In presenting NMR data, widely accepted abbreviations were used as follows: s for singlet, d for doublet, t for triplet, q for quartet, m for multiplet, br for broad, J for coupling constant, CDCl$_3$ for deuterated chloroform, DMSO$_{d6}$ for hexa-deuterated DMSO, and so on. |
| MS | Mass spectroscopy. In presenting MS data, popularly accepted abbreviations were used as follows: MALDI-TOF for matrix assisted laser desorption ionization time of flight, ESI for electrospray ionization, MW for molecular weight, (m + 1) for MH$^+$ ion peak, (m + 23) for MNa$^+$ ion peak, etc. |
| Solvents | Widely accepted abbreviations were used for solvents as follows: THF for tetrahydrofuran, MC for methylene chloride, DMF for dimethylformamide, EtOH for ethanol, MeOH for methanol, DMSO for dimethylsulfoxide, EA for ethyl acetate, and so on. |
| Reagents | Popularly accepted abbreviations were used for reagents as follows: NaH for sodium hydride, HCl for hydrochloric acid, EDCI for 1-ethyl-3-(3-dimethylaminopropyl)carbodiimide hydrochloride, HOBT for 1-hydroxy-benzotriazole, Boc for t-butyloxycarbonyl, Boc$_2$O for Boc anhydride or di-t-butyl-dicarbonate, Cbz for benzyloxycarbonyl, Fmoc for (9H-fluoren-9-yl)-methoxycarbonyl, Bts for (benzo[d]thiazole-2-sulfonyl), Bts-Cl for (benzo-[d]thiazole-2-sulfonyl)chloride, TFA for trifluoroacetic acid, TEA for triethyl-amine, DIEA for N,N-diisopropylethylamine, LiOH for lithium hydroxide, Aeg for N-(2-aminoethyl)glycine, Fmoc-Aeg-OH for N-[2-{(9H-fluoren-9-yl)-methoxycarbonyl}amino-ethyl]glycine, Fmoc-Aeg-OMe for methyl N-[2-(Fmoc-amino)ethyl]-glycinate, Fmoc-Aeg-OtBu for t-butyl N-[2-(Fmoc-amino)ethyl]-glycinate, Fmoc-Aeg-OSu for N-succinyl N-[2-(Fmoc-amino)-ethyl]-glycinate, HBTU for O-(benzotriazol-1-yl)-1,1,3,3-tetramethyluranium hexafluorophosphate, DCC for 1,3-dicyclo-hexylcarbodiimide, and so on. |
| Others | Widely accepted abbreviations were used for terminologies as follows: mp for melting point, °C. for degree in Celcius, h for hour, min for minute, g for gram, mg for milligram, kg for kilogram, l for liter, ml for milliliter, M for mole/l, compd for compound, aq for aqueous, RT for room temperature, and so on. |

Example 1

Preparation of 3-{(t-butoxycarbonyl)amino}-1-propanol (1)

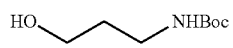

To 14 g of 3-amino-1-propanol dissolved in 150 ml THF and 150 ml water, was added drop-wise over 30 min 40.7 g of Boc$_2$O dissolved in 100 ml THF. After the reaction mixture was stirred for 24 h, the THF was removed under reduced pressure. The resulting aq layer was extracted with 200 ml EA, and the organic layer was washed with 0.5M aq citric acid and with distilled water, and then dried over anhydrous magnesium sulfate. Magnesium sulfate was filtered off, and the resulting filtrate was concentrated in vacuo to give 25 g of compd 1 as a colorless liquid. ¹H NMR (400 MHz; CDCl$_3$): δ4.84 (br s, 1H), 3.66 (t, J=5.6 Hz, 2H), 3.28 (q, J=6.0 Hz, 2H), 3.05 (br s, 1H), 1.66 (m, 2H), 1.45 (s, 9H).

Example 2

Preparation of ethyl {(N-benzoyl)-5-iodocytosine-1-yl}acetate (2)

To a stirred solution of 8.3 g of N-benzoyl-5-iodocytosine dissolved in 60 ml DMF, was added at 0° C. 1.06 g of 55% NaH in mineral oil, and the solution was stirred at RT for 2 h. After 2.7 ml ethyl bromoacetate was added to the reaction mixture, the reaction solution was stirred for another 24 h at RT, which was followed by removal of the solvent under reduced pressure. The resulting residue was dissolved and the insoluble material was filtered off. The filtrate was washed two times with saturated aq ammonium chloride, dried over anhydrous magnesium sulfate, and concentrated in vacuo. The resulting residue was purified by column chromatography (1:1 hexane/EA) to yield 6.5 g of compd 2 (compd b in Scheme 1) as a yellow solid. mp 154-5° C. ¹H NMR (400 MHz; CDCl$_3$) δ 13.31 (br s, 1H), 8.37 (d, J=7.2 Hz, 2H), 7.69 (s, 1H), 7.55 (t, J=7.4 Hz, 1H), 7.46 (t, J=7.6 Hz, 2H), 4.49 (s, 2H), 4.27 (q, J=7.2 Hz, 2H), 1.32 (t, J=7.2 Hz, 3H).

Example 3

Preparation of 3-{3-(t-butoxycarbonylamino)propyloxy}-1-propyne (3)

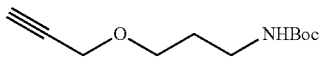

To 6.5 g of 55% NaH in mineral oil dispersed in 150 ml THF at 0° C., was added dropwise over 15 min 25 g of compd 1, and the mixture was stirred for 1 h. After 17.5 ml propargyl bromide (80% toluene solution) was added drop-wise over 30 min, the reaction mixture was stirred at RT for 20 h. The reaction was quenched by slowly adding 250 ml water and THF was removed under reduced pressure. Then the resulting aq mixture was extracted with 250 ml EA, which was washed 3 times with 250 ml water. The organic layer was dried over anhydrous magnesium sulfate, and magnesium sulfate was filtered off. The resulting filtrate was concentrated in vacuo and subjected to column chromatography (5:1 Hexane/EA) to afford 22.7 g of compd 3 as a yellow liquid. ¹H NMR (400

MHz; DMSO$_{d6}$) δ 6.78 (t, J=5.2 Hz, 1H), 4.09 (d, J=2.4 Hz, 2H), 3.43-3.39 (m, 3H), 2.95 (q, J=6.4 Hz, 2H), 1.60 (m, 2H), 1.37 (s, 9H).

Example 4

Preparation of 4-{2-(t-butoxycarbonylamino)ethoxy}-1-butyne (4)

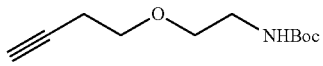

To 3.8 g of 4-(2-azidoethoxy)-1-butyne dissolved in 17 ml THF, were added 7.2 g of triphenylphosphine and 0.7 ml water, and the reaction mixture was stirred for 8 h, which was followed by removal of the solvent under reduced pressure. Then the resulting residue was dissolved in 20 ml EA and extracted twice with 10 ml 1M aq HCl. Aq sodium carbonate was added to the aq layer to adjust pH to 9~10. 5.96 g of Boc$_2$O dissolved in 15 ml THF was added to the solution, and the reaction mixture was stirred for 12 h. After THF was removed in vacuo, the resulting solution was extracted with EA. The organic layer was washed with 0.5M aq citric acid, and dried over anhydrous magnesium sulfate. The organic layer was concentrated and purified by column chromatography (9:1 Hexane/EA) to afford 3.4 g of compd 4 as a yellow oil. $^1$H NMR (400 MHz; CDCl$_3$) δ4.95 (s, 1H), 3.58 (t, J=6.8 Hz, 2H), 3.53 (t, J=5.0 Hz, 2H), 3.32 (m, 2H), 2.46 (m, 2H), 2.00 (t, J=2.8 Hz, 1H), 1.45 (s, 9H).

Example 5

Preparation of 3-{2-(t-butoxycarbonylamino)ethoxy}-1-propyne (5)

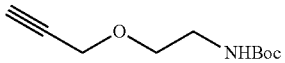

20 g of 2-{(t-butoxycarbonyl)amino}-1-ethanol was reacted and purified by similarly following the procedure described in Example 3 to afford 23.7 g of compd 5 as a pale yellow oil. $^1$H NMR (400 MHz; DMSO$_{d6}$) δ 6.81 (t, 1H), 4.11 (d, J=2.4 Hz, 2H), 3.41 (m, 3H), 3.07 (q, J=6.0 Hz, 2H), 1.38 (s, 9H).

Example 6

Preparation of 3-[N-{3-(t-butoxycarbonylamino)propyl}-N-(t-butoxy-carbonyl)amino]-1-propyne (6)

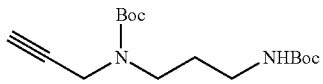 [SMILES: C#CCN(CCCNC(=O)OC(C)(C)C)C(=O)OC(C)(C)C]

To a stirred solution of N-[3-(t-butoxycarbonylamino)propyl]-N-(2-propynyl)amine dissolved in 83 ml THF and 95 ml water, was added drop-wise 42 g of Boc$_2$O at RT. The reaction solution was stirred for 1.5 h, and concentrated in vacuo. The resulting aq layer was extracted with EA. The EA layer was washed in series with 0.5M aq citric acid and brine, dried over anhydrous magnesium sulfate, concentrated under reduced pressure, and purified by column chromatography (1:1 Hexane/EA) to give 19 g of compd 6 as a yellow oil. $^1$H NMR (400 MHz; CDCl$_3$) δ 5.26 (br s, 0.6H), 4.74 (br s, 0.4H), 4.07 (br s, 1H), 3.98 (br s, 1H), 3.40 (t, J=6.4 Hz, 2H), 3.13 (m, 2H), 2.21 (t, 1H), 1.73 (m, 2H), 1.49 (s, 9H), 1.45 (s, 9H).

Example 7

Preparation of 3-[2-{2,3-bis(benzyloxycarbonyl)guanidino}-ethoxy]-1-propyne (7)

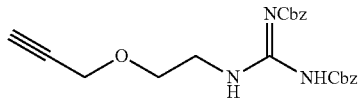

To a stirred solution of 10.9 g of compd 5 dissolved in 110 ml MC, was added 110 ml TFA at 0° C. drop-wise over 2 h, and the reaction mixture was stirred for another 3 h. The reaction solution was concentrated under reduced pressure and the resulting residue was dissolved in 40 ml MC at 0° C., to which was added 12.3 ml TEA and then 8.8 g of 1,3-bis(benzyloxycarbonyl)-2-(methylthio)pseudourea at RT. The reaction solution was stirred for 4 h and washed twice with water. The organic layer was dried over anhydrous magnesium sulfate, concentrated in vacuo, and subjected to column chromatography (5:1 hexane/EA) to afford 9.8 g of compd 7 as a white solid. $^1$H NMR (400 MHz; DMSO$_{d6}$) δ 11.72 (s, 1H), 8.58 (s, 1H), 7.40-7.35 (m, 10H), 5.18 (s, 2H), 5.12 (s, 2H), 4.18 (d, 2H), 3.67-3.66 (m, 4H), 2.43 (t, 1H).

Example 8

Preparation of 2-{(t-butoxycarbonyl)amino}-1-(2-propynyl-1-oxy)}-(R)-propane (8)

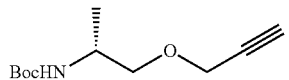

10.8 g of t-butyl-(R)-1-hydroxy-(propan-2-yl)carbamate was reacted and purified by similarly following the procedure described in Example 3 to afford 10.1 g of compd 8 as a yellow oil. $^1$H NMR (500 MHz; DMSO$_{d6}$) δ 6.63 (d, 1H), 4.11 (d, 2H), 3.60 (m, 1H), 3.37-3.33 (m, 2H), 3.26-3.23 (m, 1H), 1.38 (s, 9H), 1.05 (d, 3H).

Example 9

Preparation of N-[2-{2-(t-butoxycarbonyl)aminoethoxy}ethyl]-N-[2-{(3-butynyl)-1-oxy}ethyl]-N-(t-butoxycarbonyl)amine (9)

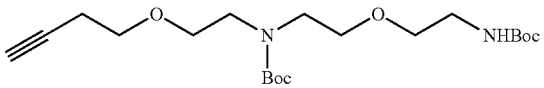 [SMILES: C#CCCOCCN(CCOCCNC(=O)OC(C)(C)C)C(=O)OC(C)(C)C]

To a stirred solution of 5 g of 2-{(3-butynyl)-1-oxy}ethyl methanesulfonate and 5.32 g of 2-[2-{2-(t-butoxycarbonyl)amino}ethyl-1-oxy]ethylamine in 60 ml acetonitrile, was added drop-wise 3.6 g of potassium carbonate dissolved in water at 0° C. The reaction solution was allowed to slowly warm to RT and stirred for another 24 h, and then concentrated under reduced pressure. The resulting residue was dissolved in MC and washed with water. The organic layer was concentrated and dissolved in 80 ml THF and 80 ml water, to which was added 8.4 g of Boc₂O dissolved in 50 ml THF. The reaction mixture was stirred at RT for 16 h, which was followed by removal of THF in vacuo and extraction with EA. The organic layer was washed in series with 0.5M aq citric acid, water, and brine. The organic layer was dried over anhydrous sodium sulfate, concentrated, and purified by column chromatography (hexane→1:4 EA/hexane) to obtain 2.45 g of compd 9 as a pale yellow oil. ¹H NMR (400 MHz; CDCl₃) δ 5.08 (br s, 0.5H), 4.93 (br s, 0.5H), 3.61-3.46 (m, 12H), 3.31 (m, 2H), 2.48 (m, 2H), 1.99 (t, 1H), 1.48 (s, 9H), 1.46 (s, 9H).

Example 10

Preparation of ethyl 2-[6-{3-(t-butoxycarbonylamino)propyl-1-oxy}-methyl-2-oxo-2H-pyrrolo[2,3-d]pyrimidin-3(7H)-yl]acetate (10)

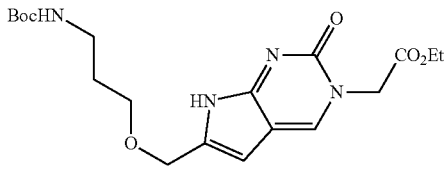 [SMILES: CCOC(=O)Cn1cc2cc(COCCCNC(=O)OC(C)(C)C)[nH]c2nc1=O]

To a stirred solution of 6.5 g of compd 2 dissolved in 120 ml DMF, were added in series 580 mg of CuI, 4.2 ml TEA, 9.74 g of compd 3, and 1.76 g of Pd(PPh₃)₄. Then the reaction mixture was stirred for 24 h at 50° C. with light shielded, and concentrated under reduced pressure. The resulting residue was dissolved in 250 ml EtOH and stirred at reflux for 18 h. Then the solution was concentrated in vacuo and subjected to chromatographic separation (95:5 EA/EtOH) to obtain 2.3 g of compd 10 as a dark red foam/solid. ¹H NMR (400 MHz; DMSO_{d6}) δ 11.30 (br s, 1H), 8.37 (s, 1H), 6.78 (m, 1H), 6.19 (s, 1H), 4.70 (s, 2H), 4.37 (s, 2H), 4.14 (q, J=7.2 Hz, 2H), 3.42 (t, J=6.4 Hz, 2H), 2.98 (m, 2H), 1.63 (m, 2H), 1.36 (s, 9H), 1.20 (t, J=7.2 Hz, 3H).

Example 11

Preparation of 2-[6-{3-(t-butoxycarbonylamino)propyl-1-oxy}methyl-2-oxo-2H-pyrrolo-[2,3-d]pyrimidin-3(7H)-yl]acetic acid (11)

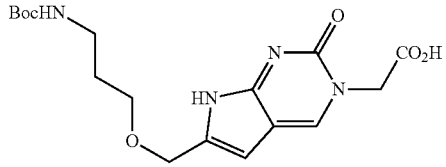 [SMILES: CC(C)(C)OC(=O)NCCCOCc1cc2cn(CC(=O)O)c(=O)nc2[nH]1]

To 3.3 g of compd 10, were added 15 ml THF, 30 ml water, and then 760 mg LiOH, and the mixture was stirred at RT for 20 min. After THF was removed under reduced pressure, the resulting aq solution was washed with diethyl ether. The aq layer was acidified to pH 3 with 1M aq HCl and extracted with EA. The organic layer was dried over anhydrous sodium sulfate and concentrated in vacuo to yield 2.46 g of compd 11 as a white solid. ¹H NMR (400 MHz; DMSO_{d6}) δ 11.05 (s, 1H), 8.16 (s, 1H), 6.79 (t, 1H), 6.12 (s, 1H), 4.35 (s, 2H), 4.23 (s, 2H), 3.41 (t, 2H), 2.97 (q, J=6.4 Hz, 2H), 1.64 (m, 2H), 1.36 (s, 9H).

Example 12

Preparation of ethyl N-[2-{(benzo[d]thiazole-2-sulfonyl)amino}-ethyl]-N-[2-[6-{3-(t-butoxycarbonylamino)propyl-1-oxy}methyl-2-oxo-2H-pyrrolo-[2,3-d]pyrimidin-3(7H)-yl]acetyl]glycinate (12)

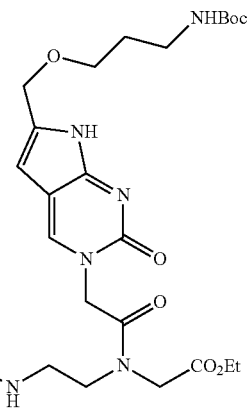

To 4.0 g of compd 11 and 3.6 g of ethyl N-[2-{(benzo[d]thiazole-2-sulfonyl)amino}ethyl]glycinate dissolved in 30 ml DMF, were added at RT 2.42 g of EDCI and 1.70 g of HOBt. The reaction mixture was stirred for 8 h. After the solvent was removed in vacuo, the resulting residue was dissolved in MC, and washed with 1M aq HCl and then with water. The MC layer was concentrated under reduced pressure and purified by column chromatography (95:5 MC/MeOH) to obtain 4.6 g of compd 12 as a yellow foam/solid. ¹H NMR (400 MHz; DMSO_{d6}) δ 11.09 (br s, 1H), 8.74 (s, 0.6H), 8.58 (s, 0.4H), 8.27 (m, 1H), 8.20-8.14 (m, 2H), 7.66 (m, 2H), 6.56 (br s, 1H), 6.16 (m, 1H), 4.91 (s, 1.2H), 4.73 (s, 0.8H), 4.38 (s, 2.6H), 4.17 (m, 0.9H), 4.07 (m, 2.5H), 3.67 (m, 1.1H), 3.49-3.44 (m, 4H), 3.26 (m, 0.9H), 3.01 (m, 2H), 1.66 (m, 2H), 1.38 (s, 9H), 1.24 (t, J=7.0 Hz, 1.2H), 1.17 (t, J=7.0 Hz, 1.8H).

Example 13

Preparation of N-[2-{(benzo[d]thiazole-2-sulfonyl)amino}ethyl]-N-[2-[6-{3-(t-butoxycarbonylamino)propyl-1-oxy}methyl-2-oxo-2H-pyrrolo-[2,3-d]-pyrimidin-3(7H)-yl]acetyl]glycine (13)

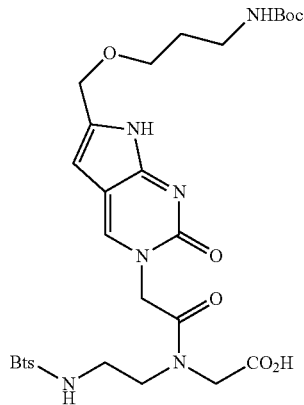

4.5 g of compd 12 and 670 mg of LiOH were dispersed in 20 ml THF and 20 ml water, and stirred at RT for 20 min. THF was removed in vacuo, and the resulting aq solution was washed with diethyl ether. The aq layer was acidified to pH 3 with 1M aq HCl, and extracted with EA. The EA layer was dried over anhydrous sodium sulfate and concentrated under reduced pressure to afford 4.4 g of compd 13 as a dark yellow solid. $^1$H NMR (400 MHz; DMSO$_{d6}$) δ 11.32 (br s, 1H), 8.36 (m, 1H), 8.28 (m, 1.6H), 8.22 (s, 0.4H), 7.73 (m, 2H), 6.78 (m, 1H), 6.20 (s, 1H), 4.94 (s, 1.2H), 4.84 (s, 0.8H), 4.52 (s, 0.8H), 4.37 (s, 2H), 4.30 (s, 1.2H), 4.26 (m, 1.2H), 4.07 (m, 2H), 3.87 (m, 0.8H), 3.43 (m, 2H), 2.99 (m, 2H), 1.63 (m, 2H), 1.37 (s, 9H).

Example 14

Preparation of 1-{(benzo[d]thiazole-2-sulfonyl)}-2-oxo-4-[6-{3-(t-butoxycarbonylamino)propyl-1-oxy}methyl-2-oxo-2H-pyrrolo[2,3-d]pyrimidin-3(7H)-yl]acetyl]piperazine (14)

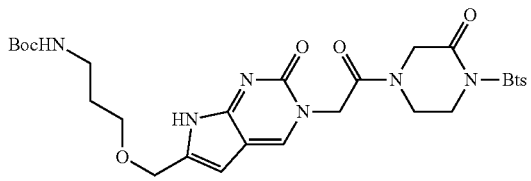

4.4 g of compd 13 and 1.49 g of EDCI in 50 ml DMF were stirred at RT for 16 h. After the reaction mixture was concentrated in vacuo, the resulting residue was dissolved in 50 ml MC. The MC solution was washed in series with 1M aq HCl and water, concentrated in vacuo, and then purified by column chromatography (acetone) to obtain 1.5 g of compd 14 as a brown foam/solid. $^1$H NMR (400 MHz; DMSO$_{d6}$) δ 11.25 (br s, 1H), 8.36 (m, 1H), 8.29 (m, 1H), 8.25 (s, 0.6H), 8.19 (0.4H), 7.72 (m, 2H), 6.78 (t, J=5.2 Hz, 1H), 6.18 (s, 1H), 4.92 (s, 1.2H), 4.82 (s, 0.8H), 4.51 (s, 0.8H), 4.37 (s, 2H), 4.29 (s, 1.2H), 4.23 (m, 1.2H), 4.06 (m, 2H), 3.87 (m, 0.8H), 3.41 (t, J=6.4 Hz, 2H), 2.98 (q, J=6.8 Hz, 2H), 1.62 (m, 2H), 1.36 (s, 9H). MS/ESI (m+23/MNa$^+$)=682.2 (observed), MW=659.8 ($C_{28}H_{33}N_7O_8S_2$)

Starting from acetylene derivatives 4~9, pyrollocytosine derivatives 15~20 were prepared by similarly following the procedure described in Example 10

Spectral and physical data for compds 15~20 are provided in the table below.

Examples 15~20

Analytical data for pyrollocytosine derivatives 15~20.

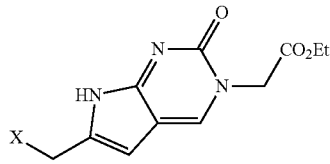

| Compd | Starting Material | X | Spectral & Physical Data |
|---|---|---|---|
| 15 | 4 | BocHN~O~ | $^1$H NMR (400 MHz; DMSO$_{d6}$) δ 11.12 (s, 1H), 8.27 (s, 1H), 6.79 (t, J = 5.4 Hz, 1H), 6.00 (s, 1H), 4.68 (s, 2H), 4.14 (q, J = 7.2 Hz, 2H), 3.65 (t, J = 6.6, 2H), 3.39 (t, J = 6.2 Hz, 2H), 3.08 (m, 2H), 2.78 (t, J = 6.6 Hz, 2H), 1.37 (s, 9H), 1.20 (t, J = 7.2 Hz, 3H). Pale green foam/solid. |
| 16 | 5 | BocHN~O~ | $^1$H NMR (400 MHz; DMSO$_{d6}$) δ 11.35 (s, 1H), 8.39 (s, 1H), 6.87 (t, J = 5.2 Hz, 1H), 6.21 (s, 1H), 4.70 (s, 2H), 4.41 (s, 2H), 4.15 (q, J = 7.2 Hz, 2H), 3.43 (m, 2H), 3.12 (m, 2H), 1.38 (s, 9H), 1.21 (t, J = 7.2 Hz, 3H). Pale yellow foam/solid. |
| 17 | 6 | NHBoc, BocN | $^1$H NMR (400 MHz; DMSO$_{d6}$) δ 11.20 (br s, 0.6H), 8.86 (br s, 0.4H), 8.57 (s, 0.2H), 8.35 (s, 0.8H), 6.83-6.76 (m, 1H), 6.00 (s, 0.8H), 5.76 (s, 0.2H), 4.75 (s, 0.3H), 4.70 (s, 1.7H), 4.55 (s, 0.3H), 4.30 (s, 1.7H), 4.14 (q, J = 7.2 Hz, 2H), 3.18 (m, 2H), 2.90-2.88 (m, 2H), 1.58 (m, 2H), 1.40-1.36 (m, 18H), 1.20 (t, 3H). Brown foam/solid. |

-continued

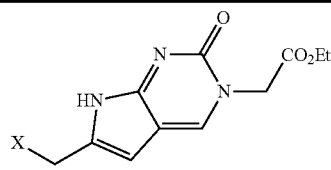

| Compd | Starting Material | X | Spectral & Physical Data |
|---|---|---|---|
| 18 | 7 | CbzN≈(NHCbz)-HN-CH₂CH₂-O-〜 | ¹H NMR (400 MHz; DMSO$_{d6}$) δ 11.57 (s, 1H), 11.33 (s, 1H), 8.50 (m, 1H), 8.37 (s, 1H), 7.44-7.31 (m, 10H), 6.22 (s, 1H), 5.22 (s, 2H), 5.03 (s, 2H), 4.70 (s, 2H), 4.44 (s, 2H), 4.14 (q, 2H), 3.57-3.53 (m, 4H), 1.21 (t, 3H). Pale brown solid. |
| 19 | 8 | BocHN-CH(CH₃)-CH₂-O-〜 | ¹H NMR (500 MHz; DMSO$_{d6}$) δ 11.32 (s, 1H), 8.38 (s, 1H), 6.71 (d, 1H), 6.20 (s, 1H), 4.70 (s, 2H), 4.41 (m, 2H), 4.14 (q, 2H), 3.65 (m, 1H), 3.37-3.34 (m, 1H), 3.26-3.22 (m, 1H), 1.37 (s, 9H), 1.20 (t, 3H), 1.02 (d, 3H). Pale brown solid. |
| 20 | 9 | BocHN-CH₂CH₂-O-CH₂CH₂-N(Boc)-CH₂CH₂-O-〜 | ¹H NMR (500 MHz; DMSO$_{d6}$) δ 11.13 (s, 1H), 8.25 (s, 1H), 6.73 (s, 1H), 5.99 (s, 1H), 4.68 (s, 2H), 4.12 (q, 2H), 3.67 (t, 2H), 3.48~3.27 (m, 10H), 3.04 (q, 2H), 2.78 (t, 2H), 1.38 (s, 9H), 1.36 (s, 1H), 1.19 (t, 3H). Brown solid. |

Starting from pyrollocytosine derivatives 15, 16, 17, and 20, modified cytosine PNA monomers 21~24 were prepared by similarly following the procedures described in Examples 11~14. Spectral and physical data for compds 21~24 are provided in the table below.

Examples 21~24

Analytical data for cytosine PNA monomers 21~24.

| Compd | Starting Material | X | Spectral & Physical Data |
|---|---|---|---|
| 21 | 15 | BocHN–CH2CH2–O–CH2–C(*)– | $^1$H NMR (400 MHz; DMSO$_{d6}$) δ 11.06 (s, 1H), 8.36 (m, 1H), 8.28 (m, 1H), 8.14 (s, 0.6H), 8.08 (2, 0.4H), 7.72 (m, 2H), 6.78 (t, 1H), 5.98 (s, 1H), 4.91 (s, 1.2H), 4.80 (s, 0.8H), 4.51 (s, 0.8H), 4.29 (s, 1.2H), 4.24 (m, 1.2H), 4.06 (m, 2H), 3.86 (m, 0.8H), 3.64 (t, J = 6.4 Hz, 2H), 3.38 (t, J = 6.0 Hz, 2H), 3.07 (m, 2H), 2.78 (m, 2H), 1.37 (s, 9H). MS/ESI (m + 1) = 660.2 (observed), MW = 659.8 (C$_{28}$H$_{33}$N$_7$O$_8$S$_2$). Brown foam/solid. |
| 22 | 16 | BocHN–CH2CH2–O–CH2(*) | $^1$H NMR (400 MHz; DMSO$_{d6}$) δ 11.31 (s, 1H), 8.36 (m, 1H), 8.30-8.27 (m, 1.6H), 8.22 (s, 0.4H), 7.73 (m, 2H), 6.87 (t, J = 5.6 Hz, 1H), 6.20 (m, 1H), 4.94 (s, 1.2H), 4.83 (s, 0.8H), 4.52 (s, 0.7H), 4.41 (s, 2.1H), 4.30 (s, 1.1 H), 4.25 (m, 1.2H), 4.06 (m, 2H), 3.87 (m, 0.8H), 3.42 (t, 2H), 3.12 (m, 2H), 1.38 (s, 9H). MS/ESI (m + 1) = 646.2 (observed), MW = 645.7 (C$_{27}$H$_{31}$N$_7$O$_8$S$_2$). Red foam/solid. |
| 23 | 17 | NHBoc / BocN branched | $^1$H NMR (400 MHz; DMSO$_{d6}$) δ 11.16 (br s, 1H), 8.36 (m, 1H), 8.28 (m, 1H), 8.21 (s, 0.6H), 8.15 (s, 0.4H), 7.73 (m, 2H), 6.77 (br s, 1H), 6.00 (br s, 1H), 4.92 (s, 1.2H), 4.82 (s, 0.8H), 4.52 (s, 0.9H), 4.30 (s, 3.1H), 4.25 (m, 1.2H), 4.07 (m, 2H), 3.87 (m, 0.8H), 3.19 (m, 2H), 2.89 (m, 2H), 1.59 (m, 2H), 1.41-1.36 (m, 18H); MS/ESI (m + 23/MNa$^+$) = 781.3 (observed), MW = 758.9 (C$_{33}$H$_{42}$N$_8$O$_9$S$_2$). Red foam/solid. |
| 24 | 20 | BocHN–CH2CH2–O–... NBoc branched | $^1$H-NMR (500 MHz; DMSO$_{d6}$) δ 11.10 (m, 1H), 8.35 (m, 1H), 8.28 (m, 1H), 8.14 (s, 0.6H), 8.08 (s, 0.4H), 7.72 (m, 2H), 6.76 (m, 1H), 5.97-5.96 (s, 1H), 4.90 (s, 1.2H), 4.80 (s, 0.8H), 4.51 (s, 0.8H), 4.29 (s, 1.2H), 4.25 (t, 1.2H), 4.08-4.04 (m, 2H), 3.86 (m, 0.8H), 3.66 (m, 2H), 3.47 (m, 2H), 3.41 (m, 2H), 3.32-3.30 (m, 4H), 3.27 (m, 2H), 3.04 (m, 2H), 2.77 (m, 2H), 1.37 (s, 9H), 1.35 (s, 9H). MS/ESI (m + 23/MNa$^+$) = 869.3 (observed), MW = 847.0 (C$_{37}$H$_{50}$N$_8$O$_{11}$S$_2$). Yellow solid. |

Example 25

Preparation of 2-{3-(t-butoxycarbonylamino)propyl}amino-adenine (25)

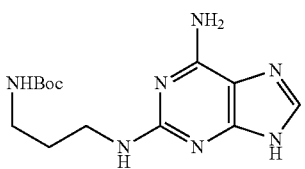 [SMILES: CC(C)(C)OC(=O)NCCCNc1nc(N)c2nc[nH]c2n1]

6.8 g of 2-chloroadenine dissolved in 68 ml 1,3-diaminopropane and 68 ml monomethoxyethanol was stirred at reflux for 24 h, and the reaction mixture was concentrated in vacuo. The resulting residue was dissolved in 100 ml THF and 100 ml water, to which was slowly added 60 g of $Boc_2O$ dissolved in 70 ml THF. The reaction mixture was stirred at RT for 6 h, and then the organic solvent was removed under reduced pressure. The resulting aq layer was extracted twice with 100 ml EA. The organic layer was washed with 0.5M aq citric acid and with brine, and dried over anhydrous magnesium sulfate. The organic layer was concentrated under reduced pressure and subjected to chromatographic separation (1:10 MeOH/MC) to obtain 4.07 g of a compd protected with two Boc groups. This compound was dissolved in 100 ml MeOH, to which was added slowly 45 ml saturated aq sodium carbonate. The reaction solution was stirred at 50° C. for 1 h, and then concentrated in vacuo. The resulting residue was dissolved in 50 ml MeOH and the insoluble material was filtered off. Then the filtrate was concentrated to afford 3.16 g of compd 25 as a white solid. $^1$H NMR (400 MHz; $DMSO_{d6}$) δ 12.11 (br s, 1H), 7.63 (s, 1H), 6.78 (t, 1H), 6.55 (s, 2H), 6.07 (t, 1H), 3.20 (q, 2H), 2.96 (q, 2H), 1.60 (m, 2H), 1.37 (s, 9H).

Starting from 2-chloroadenine and a proper diamine, 2,6-diaminopurine derivatives 26~30 were prepared by similarly following the procedure described in Example 25. Spectral and physical data for compounds 26~30 are provided in the table below.

Examples 26~30

Analytical data for 2,6-diaminopurine derivatives 26

| Compd | Starting Diamine | $L_2$ | Spectral & Physical Data |
|---|---|---|---|
| 26 | H₂N–(CH₂)₂–NH₂ (branched drawing) | —$(CH_2)_2$— | $^1$H NMR (400 MHz; $DMSO_{d6}$) δ 12.20 (br s, 1H), 7.66 (s, 1H), 6.84 (t, 1H), 6.62 (s, 2H), 6.10 (t, 1H), 3.25 (q, 2H), 3.08 (q, 2H), 1.36 (s, 9H). Pale yellow solid. |
| 27 | NH₂–(CH₂)₄–NH₂ | —$(CH_2)_4$— | $^1$H NMR (500 MHz; $DMSO_{d6}$) δ 12.07 (br s, 1H), 7.63 (s, 1H), 6.75 (s, 1H), 6.50 (s, 2H), 6.02 (s, 1H), 3.18 (q, 2H), 2.91 (q, 2H), 1.48-1.36 (m, 13H). Yellowish green solid. |
| 28 | NH₂–(CH₂)₅–NH₂ | —$(CH_2)_5$— | $^1$H NMR (400 MHz; $DMSO_{d6}$) δ 12.14 (br s, 1H), 7.65 (s, 1H), 6.77 (t, 1H), 6.55 (s, 2H), 6.01 (s, 1H), 3.17 (m, 2H), 2.89 (q, 2H), 1.48 (m, 2H), 1.41-1.36 (m, 11H), 1.26 (m, 2H). Pale yellow solid. |
| 29 | NH₂–(CH₂)₇–NH₂ | —$(CH_2)_7$— | $^1$H NMR (500 MHz; $DMSO_{d6}$) δ 12.11 (br s, 1H), 7.64 (s, 1H), 6.78 (t, J = 5.6 Hz, 1H), 6.56 (s, 2H), 6.04 (t, J = 5.5 Hz, 1H), 3.17 (td, J = 6.3, 6.3 Hz, 2H), 2.88 (td, J = 6.7, 6.7 Hz, 2H), 1.49-1.47 (m, 2H), 1.36-1.31 (m, 11H), 1.29-1.22 (m, 6H). Yellowish green solid. |

-continued

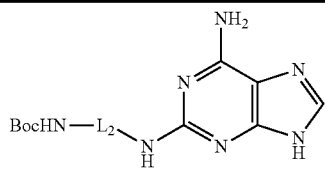

| Compd | Starting Diamine | L2 | Spectral & Physical Data |
|---|---|---|---|
| 30 | H2N-CH2CH2-O-CH2CH2-NH2 | -CH2CH2-O-CH2CH2- | $^1$H NMR (500 MHz; DMSO$_{d6}$) δ 12.15 (s, 1H), 7.64 (s, 1H), 6.84 (t, 1H), 6.56 (s, 2H), 6.05 (t, 1H), 3.48 (t, 2H), 3.39-3.34 (m, 4H), 3.07 (q, 2H), 1.37 (s, 9H). Yellow foam. |

Example 31

Preparation of 2-[2-{2-(t-butoxycarbonylamino)-2-methyl}ethyl]-amino-1H-purin-6(9H)-one (31)

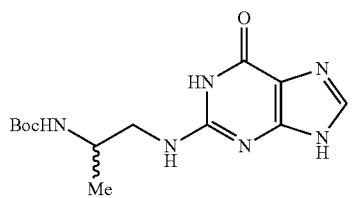 [SMILES: CC(CNc1nc2[nH]cnc2c(=O)[nH]1)NC(=O)OC(C)(C)C]

11 g of 2-chlorohypoxanthine and 4.96 ml 1,2-diaminopropane (racemic) were dispersed in 33 ml monomethoxyethanol, and stirred for 24 h at 130° C. The solvent was removed in vacuo, and the resulting residue was dissolved in 97 ml THF and 97 ml water, to which was slowly added 22.8 g of Boc$_2$O dissolved in 64 ml THF. The reaction mixture was stirred at RT for 6 h, and EA was added to the solution. The resulting precipitate was collected by filtration to obtain compd 31 as a grey solid. $^1$H NMR (500 MHz; DMSO$_{d6}$) 612.42 (s, 1H), 10.44 (br s, 1H), 7.61 (s, 1H), 6.76 (d, 1H), 6.27 (m, 1H), 3.67 (m, 1H), 3.32 (m, 1H), 3.14 (m, 1H), 1.36 (s, 9H), 1.02 (d, 3H).

Example 32

Preparation of ethyl 2-[6-amino-2-{3-(t-butoxycarbonylamino)-propyl}amino-9H-purin-9-yl]acetate (32)

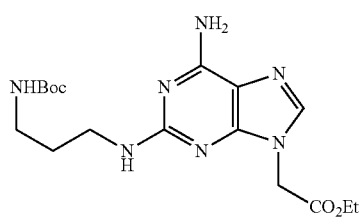 [SMILES: CCOC(=O)Cn1cnc2c(N)nc(NCCCNC(=O)OC(C)(C)C)nc21]

To a stirred solution of 3.16 g of compd 25 dissolved in 100 ml DMF, was added 480 mg of 55% NaH in mineral oil. The reaction solution was stirred for 2 h, after which was slowly added 1.98 ml ethyl bromoacetate. 2 h later, the reaction mixture was concentrated in vacuo, and purified by column chromatography (1:10 EtOH/EA) to give 2.92 g of diaminopurine analog 32 as a pale yellow solid. $^1$H NMR (400 MHz; DMSO$_{d6}$) δ 7.67 (s, 1H), 6.80 (t, 1H), 6.71 (s, 2H), 6.28 (t, 1H), 4.85 (s, 2H), 4.15 (q, 2H), 3.20 (q, 2H), 2.94 (q, 2H), 1.57 (m, 2H), 1.37 (s, 9H), 1.21 (t, 3H).

Example 33

Preparation of ethyl 2-[6-(benzyloxycarbonypamino-2-{3-(t-butoxy-carbonylamino)propyl}amino-9H-purin-9-yl]acetate (33)

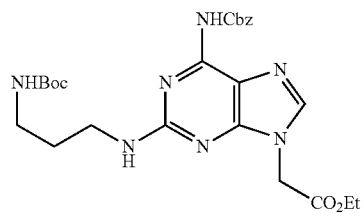 [SMILES: CCOC(=O)Cn1cnc2c(NC(=O)OCc3ccccc3)nc(NCCCNC(=O)OC(C)(C)C)nc21]

To a stirred solution of 4.68 g of compd 32 dissolved in 100 ml DMF, was added at RT 13.2 g of N-(benzyloxycarbonyl)-N'-methyl-imidazolium triflate. 12 h later the reaction mixture was concentrated under reduced pressure, and subjected to column chromatography (5% MeOH in MC) to yield 5.4 g of compd 33 as a white solid. $^1$H NMR (400 MHz; DMSO$_{d6}$) δ 10.19 (s, 1H), 7.92 (s, 1H), 7.45-7.33 (m, 5H), 6.88 (t, 1H), 6.77 (t, 1H), 5.18 (s, 2H), 4.94 (s, 2H), 4.16 (q, 2H), 3.25 (q, 2H), 2.95 (q, 2H), 1.60 (m, 2H), 1.36 (s, 9H), 1.21 (t, 3H).

Example 34

Preparation of ethyl N-[2-{2-(benzo[d]thiazole)sulfonyl}aminoethyl]-N-[2-[6-(benzyloxycarbonyl)amino-2-{3-(t-butoxycarbonylamino)-propyl}amino-9H-purin-9-yl]acetyl]glycinate (34)

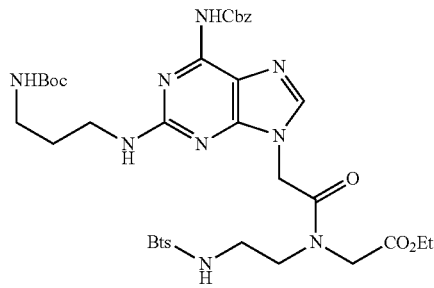

5.4 g of compd 33 and 950 mg of LiOH were dissolved in 40 ml THF and 40 ml water, and stirred at RT for 1 h. THF was removed in vacuo, and the resulting aq solution was acidified to pH 3 with 1M aq HCl, and then extracted with EA. The organic layer was dried over anhydrous sodium sulfate and concentrated under reduced pressure. The resulting residue and 2.92 g of ethyl 2-N-[2-{(benzo[d]thiazole-2-sulfonyl)amino}ethyl]glycinate were dissolved in 240 ml DMF, to which were added at RT 1.95 g of EDCI and 1.38 g of HOBt. The reaction mixture was stirred for 20 h, concentrated under reduced pressure, and dissolved in MC. The MC solution was washed with 1M aq HCl, concentrated in vacuo, and then purified by column chromatography (5% MeOH/MC) to obtain 2.7 g of compd 34 as a pale yellow foam. $^1$H NMR (400 MHz; DMSO$_{d6}$) δ 10.18 (m, 1H), 8.97 (br s, 0.6H), 8.80 (br s, 0.4H), 8.28 (d, 1H), 8.18 (m, 1H), 7.80 (s, 0.6H), 7.76 (s, 0.4H), 7.66 (m, 2H), 7.46-7.32 (m, 5H), 6.77 (m, 2H), 5.18 (s, 2H), 5.10 (s, 1.2H), 4.89 (s, 0.8H), 4.45 (s, 0.8H), 4.17 (q, 0.8H), 4.07-4.00 (m, 2.4H), 3.68 (m, 1.2H), 3.47 (m, 1.2H), 3.41 (m, 0.9H), 3.22 (m, 2.7H), 2.94 (m, 2H), 1.59 (m, 2H), 1.36 (s, 9H), 1.31-1.12 (m, 3H).

Example 35

Preparation of 1-(benzo[d]thiazole-2-sulfonyl)-2-oxo-4-[[6-(benzyl-oxycarbonyl)amino-2-{3-(t-butoxycarbonylamino)propylamino}-9H-purin-9-yl]-acetyl]piperazine (35)

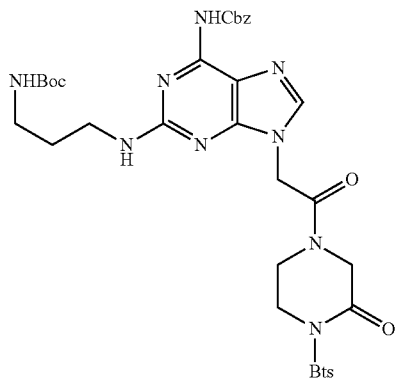

2.7 g of compd 34 and 340 mg of LiOH were dispersed in 15 ml THF and 20 ml water, and stirred for 30 min at RT. THF was removed under reduced pressure. Then the resulting aq layer was acidified to pH 3 with 1M aq HCl, and extracted with EA. The EA layer was dried over anhydrous sodium sulfate and concentrated in vacuo to obtain 2.48 g of a crude product. The crude product and 716 mg of EDCI dissolved in 70 ml DMF were stirred at RT for 20 h. The solvent was removed under reduced pressure, and the resulting residue was dissolved in MC and washed with 1M aq HCl and then with water. The organic layer was concentrated in vacuo and purified by column chromatography (acetone) to obtain 1.4 g of compd 35 as a white foam. $^1$H NMR (400 MHz; DMSO$_{d6}$) δ 10.16 (s, 1H), 8.35 (m, 1H), 8.26 (m, 1H), 7.81 (s, 0.6H), 7.77 (s, 0.4H), 7.72 (m, 2H), 7.45-7.31 (m, 5H), 6.78 (m, 2H), 5.18 (s, 2H), 5.12 (s, 1.2H), 5.01 (s, 0.8H), 4.55 (s, 0.8H), 4.29-4.27 (m, 2.4H), 4.09 (m, 2H), 3.88 (m, 0.8H), 3.26 (m, 2H), 2.95 (m, 2H), 1.61 (m, 2H), 1.36 (s, 9H); MS/ESI (m+1)=779.2 (observed), MW=778.9 ($C_{34}H_{38}N_{10}O_8S_2$).

Starting from 2,6-diaminopurine derivatives 26~30, modified adenine PNA monomers 36~40 were prepared by similarly following the procedures described in Examples 32~35. Spectral and physical data for compds 36~40 are provided in the table below.

Examples 36~40

Analytical Data for Adenine PNA Monomers 36~40

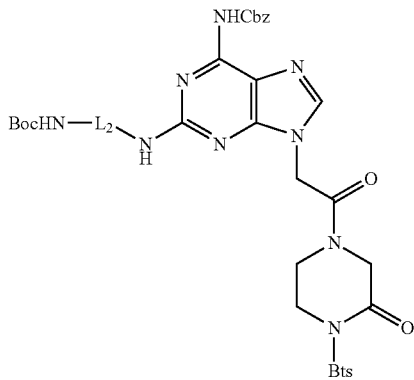

| Compd | Starting Material | L$_2$ | Spectral & Physical Data |
|---|---|---|---|
| 36 | 26 | —(CH$_2$)$_2$— | $^1$H NMR (400 MHz; DMSO$_{d6}$) δ 10.17 (s, 1H), 8.36 (m, 1H), 8.26 (m, 1H), 7.82 (s, 0.6H), 7.78 (s, 0.4H), 7.72 (m, 2H), 7.45-7.31 (m, 5H), 6.79 (2H), 5.18 (s, 2H), 5.12 (s, 1.2H), 5.01 (s, 0.8H), 4.55 (s, 0.8H), 4.29-4.25 (m, 2.4H), 4.09 (m, 2H), 3.87 (m, 0.8H), 3.29 (m, 2H), 3.11 (m, 2H), 1.33 (d, 9H). MS/ESI (m + 1) = 765.2 (observed), MW = 764.8 ($C_{33}H_{36}N_{10}O_8S_2$). White foam. |

-continued

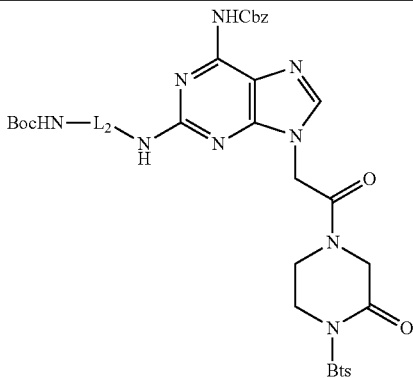

| Compd | Starting Material | L₂ | Spectral & Physical Data |
|---|---|---|---|
| 37 | 27 | —(CH₂)₄— | $^1$H NMR (400 MHz; DMSO$_{d6}$) δ 10.10 (s, 1H), 8.36 (m, 1H), 8.26 (m, 1H), 7.80 (s, 0.6H), 7.76-7.71 (m, 2.4H), 7.46-7.31 (m, 5H), 6.81-6.73 (m, 2H), 5.18 (s, 2H), 5.12 (s, 1.2H), 5.01 (s, 0.8H), 4.55 (s, 0.8H), 4.30-4.25 (m, 2.4H), 4.09 (m, 2H), 3.88 (m, 0.8H), 3.26 (m, 2H), 2.90 (m, 2H), 1.50-1.36 (m, 13H); MS/ESI (m + 1) = 793.3 (observed), MW = 792.9 (C₃₅H₄₀N₁₀O₈S₂). Yellowish red foam/solid. |
| 38 | 28 | —(CH₂)₂— | $^1$H NMR (400 MHz; DMSO$_{d6}$) δ 10.09 (s, 1H), 8.35 (m, 1H), 8.26 (m, 1H), 7.80 (s, 0.6H), 7.76 (s, 0.4H), 7.74-7.72 (m, 2.0H), 7.46-7.31 (m, 5H), 6.79-6.72 (m, 2H), 5.18 (s, 2H), 5.12 (s, 1.2H), 5.01 (s, 0.8H), 4.56 (s, 0.8H), 4.30-4.27 (m, 2.4H), 4.09 (m, 2H), 3.88 (m, 0.8H), 3.25 (m, 2H), 2.89 (m, 2H), 1.49 (m, 2H), 1.36 (m, 11H), 1.25 (m, 2H); MS/ESI (m + 1) = 807.3 (observed), MW = 806.9 (C₃₆H₄₂N₁₀O₈S₂). Yellow foam/solid. |
| 39 | 29 | —(CH₂)₇— | $^1$H NMR (500 MHz; DMSO$_{d6}$) δ 10.11 (d, J = 3.1 Hz, 1H), 8.37-8.34 (m, 1H), 8.28-8.24 (m, 1H), 7.80 (s, 0.6H), 7.76 (s, 0.4 Hz), 7.75-7.70 (m, 2H), 7.75-7.31 (m, 5H), 6.82-6.74 (m, 2H), 5.18 (s, 2H), 5.12 (s, 1.2H), 5.01 (s, 0.8H), 4.58 (s, 0.8H), 4.29 (m, 1.2H), 4.27 (q, J = 4.9 Hz, 1H), 4.06-4.03 (m, 2H), 3.88 (t, J = 5.2 Hz, 1H), 3.26-3.20 (m, 2H), 2.88-2.85 (m, 2H), 1.51-1.45 (m, 2H), 1.39-1.32 (m, 11H), 1.28-1.15 (m, 6H). MS/ESI (m + 1) = 834.8 (observed), MW = 835.0 (C₃₈H₄₆N₁₀O₈S₂). Reddish yellow foam/solid. |
| 40 | 30 | ![structure with ether linker] | $^1$H NMR (400 MHz; DMSO$_{d6}$) δ 10.14 (s, 1H), 8.35 (m, 1H), 8.26 (m, 1H), 7.82 (s, 0.6H), 7.78 (s, 0.4H), 7.73 (m, 2H), 7.46-7.31 (m, 5H), 6.81-6.74 (m, 2H), 5.18 (s, 2H), 5.13 (s, 1.2H), 5.02 (s, 0.8H), 4.55 (s, 0.8H), 4.30-4.26 (m, 2.4H), 4.09 (m, 2H), 3.88 (m, 0.8H), 3.50 (m, 2H), 3.43-3.38 (m, 4H), 3.07 (m, 2H), 1.36 (s, 9H); MS/ESI (m + 1) = 809.3 (observed), MW = 808.9 (C₃₅H₄₀N₁₀O₉S₂). Pale yellow foam. |

Example 41

Preparation of ethyl 2-[2-[2-{2-(t-butoxycarbonylamino)-2-methyl}ethyl]amino-6-oxo-6,9-dihydro-1H-purin-2-yl]acetate (41)

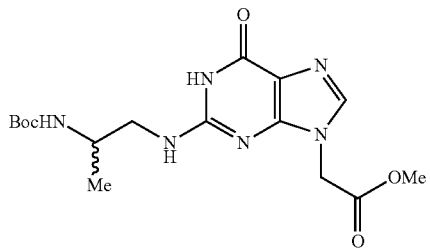 [SMILES: COC(=O)Cn1cnc2c(=O)[nH]c(NCC(C)NC(=O)OC(C)(C)C)nc21]

To a stirred solution of 4.69 g of compd 31 in 47 ml DMF, was added 790 mg of 55% NaH in mineral oil and the reaction solution was stirred for 2 h. After 1.85 ml ethyl bromoacetate was slowly added, the reaction solution was stirred for another 2 h. The reaction mixture was concentrated in vacuo and purified by column chromatography (5:95 MeOH/MC) to obtain 5.04 g of compd 41 as a pale yellow solid. $^1$H NMR (500 MHz; DMSO$_{d6}$) δ 10.55 (s, 1H), 7.67 (s, 1H), 6.74 (d, 1H), 6.40 (m, 1H), 4.87 (s, 2H), 4.17 (q, 2H), 3.65 (m, 1H), 3.28 (m, 1H), 3.16 (m, 1H), 1.36 (s, 9H), 1.21 (t, 3H), 1.01 (d, 3H).

Example 42

Preparation of 2-{2-(t-butoxycarbonylamino)ethoxy}ethylamine (42)

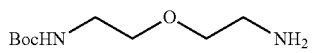

To 146 g of [2-{2-(t-butoxycarbonylamino)ethoxy}ethyl] methane sulfonate was dissolved in 500 ml DMF, was added 134 g of sodium azide. The reaction mixture was stirred at 70° C. for 20 h, and then concentrated under reduced pressure. The resulting residue was dissolved in 1,200 ml water and extracted with EA. The organic layer was dried over anhydrous sodium sulfate and concentrated in vacuo. The resulting residue was dissolved in 2,000 ml THF, to which was added 162 g of triphenylphosphine. The reaction mixture was stirred at RT for 2 h, after which was added 200 ml water. The reaction mixture was stirred at RT for 18 h and concentrated to 500 ml under reduced pressure. Then the resulting precipitate was filtered off. The filtrate was further concentrated under reduced pressure to remove THF, and washed with MC. The aq layer was concentrated to obtain 86.2 g of compd 42 as a liquid. $^1$H NMR (400 MHz; CDCl$_3$) δ 4.96 (br s, 1H), 3.54-3.48 (m, 4H), 3.34 (q, 2H), 2.88 (t, 2H), 1.48-1.46 (m, 11H).

Example 43

Preparation of 2-[2-[2-{2-(t-butoxycarbonylamino)-ethoxy}ethyl]amino-1H-purin-6(9H)-one (43)

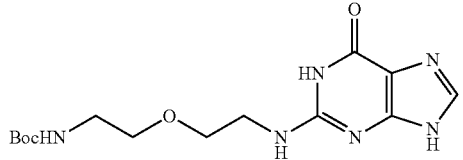 [SMILES: CC(C)(C)OC(=O)NCCOCCNc1nc2[nH]cnc2c(=O)[nH]1]

6.3 g of compd 42 and 2.0 g of 2-bromohypoxanthine were dispersed in 55 ml monomethoxyethanol and 17.5 ml water. The reaction mixture was stirred at reflux for 16 h, and the solvent was removed under reduced pressure. Then the concentrate was stirred in 20 ml MC and 10 ml water for 30 min, and the resulting precipitate was collected by filtration to obtain 2.1 g of compd 43 as a pale yellow solid. $^1$H NMR (500 MHz; DMSO$_{d6}$) δ 12.43 (br s, 1H), 10.45 (br s, 1H), 7.89 (s, 0.2H), 7.61 (s, 0.8H), 6.77 (m, 1H), 6.34 (s, 0.8H), 6.12 (s, 0.2H), 3.52 (t, 2H), 3.41 (m, 4H), 3.09 (q, 2H), 1.36 (s, 9H).

Example 44

Preparation of 2-[2-[3-(t-butoxycarbonylamino)propyloxy}-ethyl]]-amino-1H-purin-6(9H)-one (44)

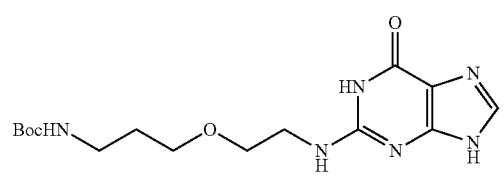 [SMILES: CC(C)(C)OC(=O)NCCCOCCNc1nc2[nH]cnc2c(=O)[nH]1]

2-{3-(t-butoxycarbonylamino)propyloxy}ethylamine and 2-bromohypoxanthine were reacted by similarly following the procedure described in Example 43 to yield compound 44 as a white solid. $^1$H NMR (500 MHz; DMSO$_{d6}$) δ 12.43 (br s, 1H), 10.45 (br s 1H), 7.61 (m, 1H), 6.80 (t, 1H), 6.30 (s, 0.7H), 6.08 (s, 0.3H), 3.49 (t, 2H), 3.41 (t, 4H), 2.99 (q, 2H), 1.61 (m, 2H), 1.37 (s, 9H).

Example 45

Preparation of 2-{3-(t-butoxycarbonylamino)propyl}amino-1H-purin-6(9H)-one (45)

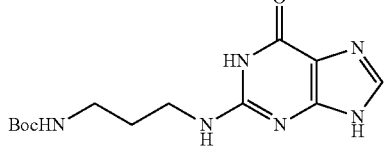

A mixture of 10 g of chlorohypoxanthine and 19.6 ml 1,3-diaminopropane dispersed in 40 ml monomethoxyethanol was stirred at 130° C. for 10 h. Then the solvent was removed under reduced pressure and the resulting residue was dissolved in 150 ml THF and 150 ml water, to which was added slowly 19.2 g of Boc$_2$O dissolved in 100 ml THF. The mixture was stirred at RT for 6 h. After EA was added, the resulting precipitate was collected by filtration to obtain 6.31 g of compd 45 as a dark green solid. $^1$H NMR (400 MHz; DMSO$_{d6}$) δ 11.13 (br s, 1H), 7.64 (s, 1H), 6.87 (s, 1H), 6.31 (s, 1H), 3.23 (q, 2H), 2.98 (m, 2H), 1.62 (m, 2H), 1.38 (s, 9H).

Guanine derivatives 46~47 were prepared using a proper diamine by similarly following the procedure described in Example 45. Spectral and physical data for compds 46~47 are provided in the table below.

Examples 46~47

Analytical Data for Guanine Derivatives 46~47

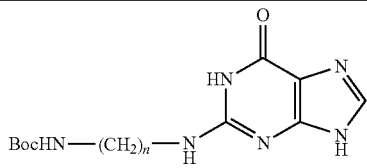

| Compd | Diamine used | n | Spectral & Physical Data |
|---|---|---|---|
| 46 | Ethylene diamine | 2 | $^1$H NMR (500 MHz; DMSO$_{d6}$) δ 12.43 (br s, 1H), 10.61 (br, 1H), 7.62 (s, 1H), 6.93 (t, 1H), 6.32 (s, 1H), 3.29 (q, 2H), 3.10 (q, 2H), 1.37 (s, 9H). Grey solid. |
| 47 | Pentylene diamine | 5 | $^1$H NMR (500 MHz; DMSO$_{d6}$) δ 12.44 (s, 1H), 10.35 (s, 1H), 7.60 (s, 1H), 6.80 (m, 1H), 6.29 (m, 1H), 3.21 (m, 2H), 2.90 (m, 2H), 1.49 (m, 2H), 1.39-1.35 (m, 11H), 1.27-1.23 (m, 2H). Pale brown solid. |

Compds 43~46 were transformed into compds 48~51 by similarly following the procedure described in Example 32. Spectral and physical data for compounds 48~51 are provided in the table below.

Examples 48~51

Analytical Data for Guanine Derivatives 48~51

| Compd | Starting Material | L$_3$ | Spectral & Physical Data |
|---|---|---|---|
| 48 | 43 | (CH₂CH₂OCH₂CH₂) | $^1$H NMR (500 MHz; DMSO$_{d6}$) δ 10.67 (s, 1H), 7.69 (s, 1H), 6.78 (m, 1H), 6.15 (t, 1H), 4.87 (s, 2H), 4.15 (q, 2H), 3.51 (m, 2H), 3.41 (m, 4H), 3.10 (m, 2H), 1.37 (s, 9H), 1.20 (t, 3H). White foam/solid. |
| 49 | 44 | (CH₂CH₂CH₂OCH₂CH₂CH₂) | $^1$H NMR (500 MHz; DMSO$_{d6}$) δ 10.57 (s, 1H), 7.69 (s, 1H), 6.79 (m, 1H), 6.44 (m, 1H), 4.87 (s, 2H), 4.16 (q, 2H), 3.48 (t, 2H), 3.40 (m, 4H), 2.99 (q, 2H), 1.61 (m, 2H), 1.37 (s, 9H), 1.21 (t, 3H). Yellow foam/solid. |

-continued

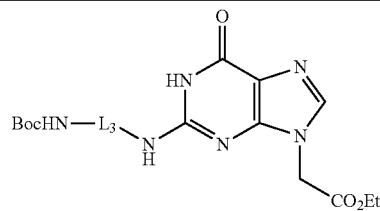

| Compd | Starting Material | L₃ | Spectral & Physical Data |
|---|---|---|---|
| 50 | 45 | (zigzag chain) | ¹H NMR (500 MHz; DMSO$_{d6}$) δ 10.64 (s, 1H), 7.68 (s, 1H), 6.91 (t, 1H), 6.47 (s, 1H), 4.88 (s, 2H), 4.16 (q, 2H), 3.28 (q, 2H), 3.08 (q, 2H), 1.36 (s, 9H), 1.21 (t, 3H). Dark red solid. |
| 51 | 46 | (branched chain) | ¹H NMR (400 MHz; DMSO$_{d6}$) δ 10.44 (br s, 1H), 7.66 (s, 1H), 6.77 (m, 1H), 6.41 (m, 1H), 4.86 (s, 2H), 4.16 (q, 2H), 3.21 (q, 2H), 2.89 (q, 2H), 1.48 (m, 2H), 1.41-1.36 (m, 11H), 1.28-1.19 (m, 5H). Dark grey solid. |

Starting from guanine derivatives 48, 49 and 51, modified guanine PNA monomers 52~54 were prepared by similarly following the procedures described in Examples 34~35. Spectral and physical data for compds 52~54 are provided in the table below.

Examples 52~54

Analytical Data for Guanine PNA Monomers 52~54

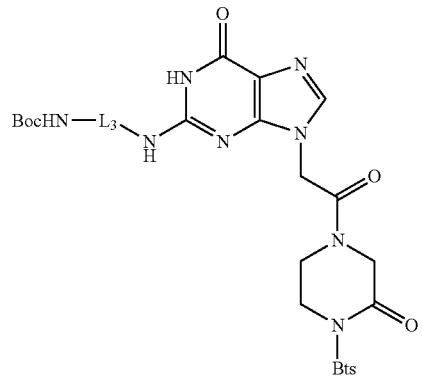

| Compd | Starting Material | L₃ | Spectral & Physical Data |
|---|---|---|---|
| 52 | 48 | (chain with O) | ¹H NMR (400 MHz; DMSO$_{d6}$) δ 10.61 (m, 1H), 8.36 (m, 1H), 8.25 (m, 1H), 7.76-7.65 (m, 3H), 6.78 (t, 1H), 6.54 (m, 1H), 5.07 (s, 1.2H), 4.96 (s, 0.8H), 4.54 (s, 0.8H), 4.30 (s, 1.2H), 4.25 (m, 1.2H), 4.07 (m, 2H), 3.88 (m, 0.8H), 3.49 (m, 2.4H), 3.40 (m, 3.6H), 3.09 (m, 2H), 1.36 (s, 9H); MS/ESI (m + 1) = 676.1 (observed), MW = 675.8 (C$_{27}$H$_{33}$N$_9$O$_8$S$_2$). Dark brown foam/solid. |

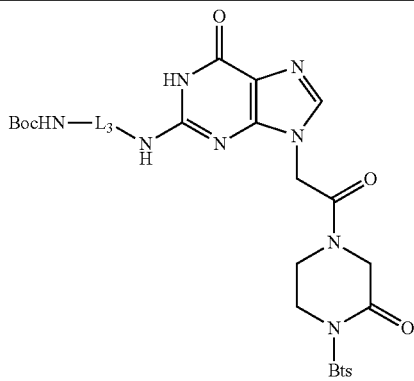

| Compd | Starting Material | L₃ | Spectral & Physical Data |
|---|---|---|---|
| 53 | 49 | | $^1$H NMR (400 MHz; DMSO$_{d6}$) δ 10.69 (s, 1H), 8.36 (m, 1H), 8.25 (m, 1H), 7.73 (m, 2H), 7.64-7.60 (m, 1H), 6.80 (t, 1H), 6.65 (br s, 1H), 5.05 (s, 1.2H), 4.94 (s, 0.8H), 4.54 (s, 0.8H), 4.29 (s, 1.2H), 4.24 (m, 1.2H), 4.07 (m, 2H), 3.87 (m, 0.8H), 3.46~3.39 (m, 6H), 2.97 (m, 2H), 1.60 (m, 2H), 1.36 (s, 9H); MS/ESI (m + 1) = 689.8 (observed), MW = 689.8 ($C_{28}H_{35}N_9O_8S_2$). Yellow foam/solid. |
| 54 | 51 | | $^1$H NMR (400 MHz; DMSO$_{d6}$) δ 10.42-10.40 (m, 1H), 8.37-8.32 (m, 1H), 8.28-8.25 (m, 1H), 7.73-7.70 (m, 2H), 7.58-7.54 (m, 1H), 6.76 (t, 1H), 6.39-6.38 (m, 1H), 5.03 (s, 1.2H), 4.92 (s, 0.8H), 4.54 (s, 0.8H), 4.29 (s, 1.2H), 4.25 (m, 1.2H), 4.08-4.07 (m, 2H), 3.87 (m, 0.8H), 3.18 (m, 2H), 2.89 (m, 2H), 1.47 (m, 2H), 1.40-1.30 (m, 11H), 1.24 (m, 2H). MS/ESI (m + 23/MNa⁺) = 696.2 (observed), MW = 673.8 ($C_{28}H_{35}N_9O_7S_2$). Red foam/solid. |

Example 55

Preparation of ethyl 2-[6-amino-2-{2-(t-butoxycarbonyl-amino)ethyl}-amino-9H-purin-9-yl]acetate (55)

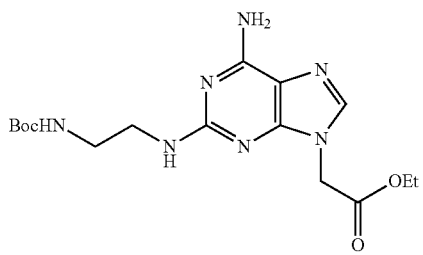 [SMILES: CCOC(=O)Cn1cnc2c(N)nc(NCCNC(=O)OC(C)(C)C)nc21]

Compd 55 was prepared from compd 26 by similarly following the procedure for Example 32. Pale yellow solid. $^1$H NMR (400 MHz; DMSO$_{d6}$) δ 7.70 (s, 1H), 6.84 (t, 1H), 6.79 (s, 2H), 6.30 (t, 1H), 4.87 (s, 2H), 4.16 (q, 2H), 3.25 (q, 2H), 3.08 (q, 2H), 1.37 (s, 9H), 1.22 (t, 3H).

Example 56

Preparation of ethyl 2-[6-amino-2-[2-{2,3-bis(benzyloxy-carbonyl)guanidino}ethyl]amino-9H-purin-9-yl]acetate (56)

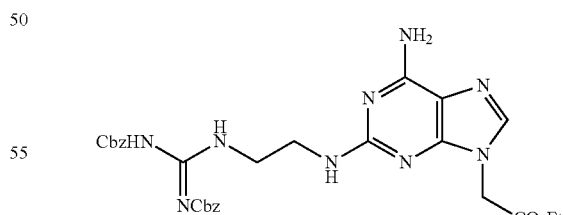

To 4.42 g of compd 55 dissolved in 22 ml MC, was slowly added 22 ml TFA at 0° C., and the solution was stirred for 2.5 h. The reaction solution was concentrated under reduced pressure, to which was added 100 ml diethyl ether. The resulting precipitate was collected by filtration to obtain 5.79 g of a pale brown solid intermediate product. 3.9 g of the intermediate was dissolved in 39 ml MC, to which was added slowly 6.9 ml TEA at 0° C. The solution was stirred for 15 min at RT, to which was added 2.48 g of 1,3-bis(benzyloxycarbonyl)-2-(methylthio)pseudourea. Then the reaction mixture was stirred for another 24 h, and washed with 0.5M aq HCl. The organic layer was dried over anhydrous magnesium sulfate and concentrated under reduced pressure to yield 4.58 g of compd 56 as a pale yellow solid. $^1$H NMR (500 MHz; DMSO$_{d6}$) δ 11.59 (s, 1H), 8.56 (t, 1H), 7.69 (s, 1H), 7.39-7.29 (m, 10H), 6.75 (s, 2H), 6.53 (s, 1H), 5.15 (s, 2H), 5.02 (s, 2H), 4.86 (s, 2H), 4.13 (q, 2H), 3.50 (q, 2H), 3.37 (m, 2H), 1.19 (t, 3H).

Example 57

Preparation of ethyl 2-[6-(benzyloxycarbonylamino)-2-[2-{2,3-bis-(benzyloxycarbonyl)guanidino}ethyl]amino-9H-purin-9-yl]acetate (57)

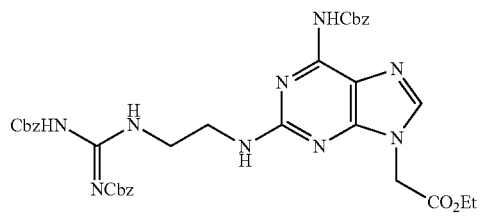

4.54 g of compd 56 and 8.22 g of N-(benzyloxycarbonyl)-N'-methyl-imidazolium triflate were dissolved in 90 ml DMF, and stirred for 29 h at RT. The solvent was removed under reduced pressure, and the resulting residue was purified by column chromatography (1:3 hexane/EA) to afford 3.06 g of compd 57 as a white foam/solid. $^1$H NMR (500 MHz; DMSO$_{d6}$) δ 11.60 (s, 1H), 10.25 (s, 1H), 8.57 (t, 1H), 7.95 (s, 1H), 7.45-7.29 (m, 15H), 7.14 (t, 1H), 5.18 (s, 2H), 5.14 (s, 2H), 5.02 (s, 2H), 4.95 (s, 2H), 4.15 (q, 2H), 3.54 (q, 2H), 3.42 (q, 2H), 1.19 (t, 3H).

Example 58

Preparation of ethyl 2-[6-amino-2-{4-(t-butoxycarbonyl-amino)butyl}-amino-9H-purin-9-yl]acetate (58)

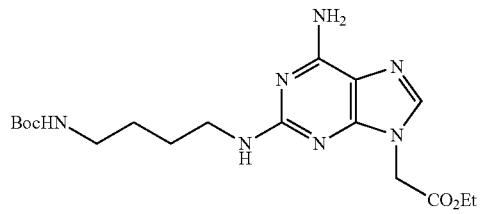 [SMILES: CCOC(=O)Cn1cnc2c(N)nc(NCCCCNC(=O)OC(C)(C)C)nc21]

Compd 58 was prepared from compd 27 as a reddish yellow foam/solid by similarly following the procedure described in Example 32. $^1$H NMR (500 MHz; DMSO$_{d6}$) δ 7.67 (s, 1H), 6.79 (t, 1H), 6.69 (s, 2H), 6.30 (m, 1H), 4.85 (s, 2H), 4.15 (q, 2H), 3.22-3.17 (m, 2H), 2.93-2.89 (m, 2H), 1.45 (m, 2H), 1.40-1.36 (m, 11H), 1.21 (t, 3H).

Example 59

Preparation of ethyl 2-[6-(benzyloxycarbonylamino)-2-[4-{2,3-bis-(benzyloxycarbonyl)guanidino}butyl]amino-9H-purin-9-yl]acetate (59)

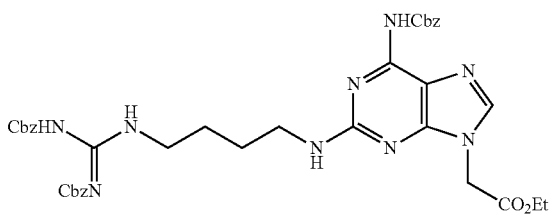

Compd 59 was prepared from compd 58 as a pale yellow foam/solid by similarly following the procedures described in Examples 56~57. $^1$H NMR (500 MHz; DMSO$_{d6}$) δ 11.49 (s, 1H), 10.12 (s, 1H), 8.28 (t, 1H), 7.91 (s, 1H), 7.45-7.31 (m, 5H), 6.95 (t, 1H), 5.17 (s, 2H), 4.93 (s, 2H), 4.16 (q, 2H), 3.28 (m, 4H), 1.51 (m, 4H), 1.46 (s, 9H), 1.38 (s, 9H), 1.21 (t, 3H).

Example 60

Preparation of ethyl 2-[6-amino-2-{5-(t-butoxycarbonylamino)-pentyl}amino-9H-purin-9-yl]acetate (60)

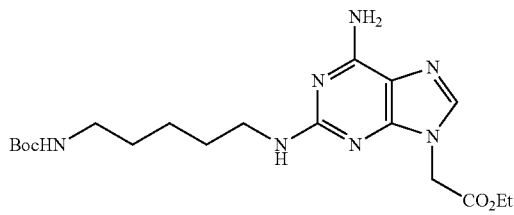 [SMILES: CCOC(=O)Cn1cnc2c(N)nc(NCCCCCNC(=O)OC(C)(C)C)nc21]

Compd 60 was prepared from compd 28 as a reddish yellow foam/solid by similarly following the procedure described in Example 32. $^1$H NMR (500 MHz; DMSO$_{d6}$) δ 7.67 (s, 1H), 6.78 (t, 1H), 6.69 (s, 2H), 6.28 (m, 1H), 4.85 (s, 2H), 4.15 (q, 2H), 3.18 (q, 2H), 2.89 (q, 2H), 1.47 (m, 2H), 1.40-1.34 (m, 1H), 1.25 (m, 2H), 1.21 (t, 3H).

Example 61

Preparation of ethyl 2-[6-{di-(t-butoxycarbonyl)}amino-2-[5-{(t-butoxycarbonyl)amino}pentyl]amino-9H-purin-9-yl]acetate (61)

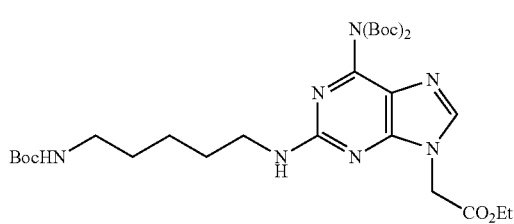

To 6.98 g of compd 60 dissolved in 100 ml THF, were added 7.95 g of Boc$_2$O and 186 mg of 4-(N,N-dimethylamino)pyridine, and the solution was stirred for 10 min. Then the solution was mixed with 4.62 ml TEA, stirred for 30 min, slowly heated to 50° C., and then stirred for another 24 h at the temperature. The reaction solution was concentrated in vacuo, and the resulting residue was dissolved in 170 ml EA and washed in series with 0.5M aq HCl and water. The organic layer was dried over anhydrous sodium sulfate, concentrated, and subjected to chromatographic separation (1:1 hexane/MC→MC) to obtain compd 61 as a yellow foam/solid. $^1$H NMR (500 MHz; DMSO$_{d6}$) δ 8.05 (s, 1H), 7.23 (t, 1H), 6.77 (t, 1H), 5.00 (s, 2H), 4.19 (q, 2H), 3.25 (q, 2H), 2.91 (q, 2H), 1.53 (m, 2H), 1.40-1.39 (m, 29H), 1.28 (m, 2H), 1.22 (t, 3H).

Example 62

Preparation of ethyl 2-[2-[2-{2,3-bis-(benzyloxycarbonyl)-guanidino}ethyl]amino-6-oxo-6,9-dihydro-1H-purin-2-yl]acetate (62)

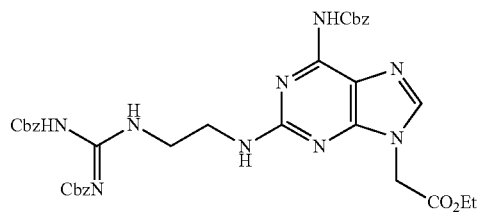

Compd 50 was converted to compd 62 as a white solid by similarly following the procedure described in Example 57. $^1$H NMR (500 MHz; DMSO$_{d6}$) δ 11.59 (s, 1H), 10.68 (s, 1H), 8.50 (t, 1H), 7.68 (s, 1H), 7.42-7.29 (m, 10H), 6.58 (m, 1H), 5.13 (s, 2H), 5.02 (s, 2H), 4.86 (s, 2H), 4.12 (q, 2H), 3.50 (m, 2H), 3.46 (m, 2H), 1.18 (t, 3H).

Example 63

Preparation of 2-[6-(benzyloxycarbonylamino)-2-[2-{2,3-bis-(benzyloxycarbonyl)guanidino}ethyl]amino-9H-purin-9-yl]acetic acid (63)

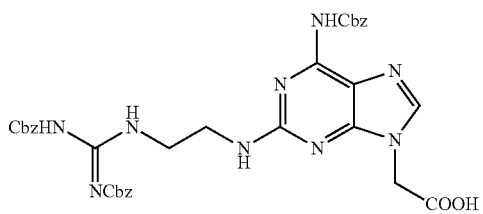

To 2.57 g of compd 57 dissolved in 7.1 ml THF and 7.1 ml water, was added 340 mg of LiOH at 0° C., and the solution was stirred at RT for 40 min. The reaction solution was acidified to pH 5~6 with 1N aq HCl at 0° C., and the resulting solid was collected by filtration to yield 2.33 g of compd 63 as a white solid. $^1$H NMR (500 MHz; DMSO$_{d6}$) δ 11.59 (s, 1H), 10.21 (s, 1H), 8.57 (t, 1H), 7.93 (s, 1H), 7.45-7.28 (m, 15H), 7.12 (t, 1H), 5.17 (s, 2H), 5.13 (s, 2H), 5.02 (s, 2H), 4.83 (s, 2H), 3.53 (q, 2H), 3.42 (q, 2H).

Example 64

Preparation of t-butyl N-[2-{(9H-fluoren-9-yl)methoxycarbonylamino}ethyl)]-N-[2-{6-(benzyloxycarbonylamino)-2-[2-{2,3-bis-(benzyloxy-carbonyl)-guanidino}ethyl]amino-9H-purin-9-yl}acetyl] glycinate (64)

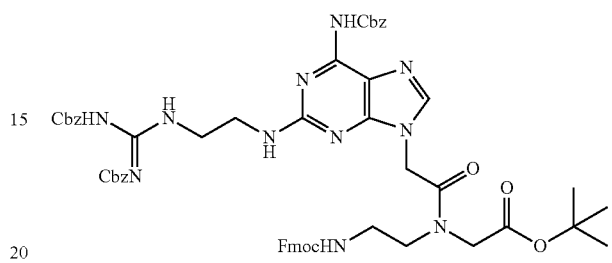

To 1.6 g of compd 63 dissolved in 30 ml DMF, were added at 0° C. 660 mg of EDCI and 910 mg of Fmoc-Aeg-OtBu. The reaction solution was stirred for 2 h at RT and then concentrated under reduced pressure. The resulting residue was dissolved in 50 ml MC and washed with 0.5M aq HCl, and the organic layer was dried over anhydrous sodium sulfate. Then the organic layer was concentrated and subjected to chromatographic separation (65:1 MC/MeOH) to obtain 500 mg of compd 64 as a white solid. $^1$H NMR (500 MHz; DMSO$_{d6}$) δ 11.59 (s, 0.4H), 11.58 (s, 0.6H), 10.21 (s, 1H), 8.55 (m, 1H), 7.47-7.28 (m, 20H), 7.06 (br, 1H), 5.17-4.89 (m, 8H), 4.34-4.28 (m, 2.8H), 4.20 (m, 1H), 3.95 (s, 1.2H), 3.52 (m, 3.4H), 3.43 (m, 2.2H), 3.34 (m, 1.7H), 3.12 (m, 0.7H), 1.43 (s, 3H), 1.34 (s, 6H).

Example 65

Preparation of N-[2-{(9H-fluoren-9-yl)methoxycarbonylamino}-ethyl)]-N-[2-{6-(benzyloxycarbonylamino)-2-[2-{2,3-bis(benzyloxycarbonyl)-guanidino}ethyl]amino-9H-purin-9-yl}acetyl] glycine (65)

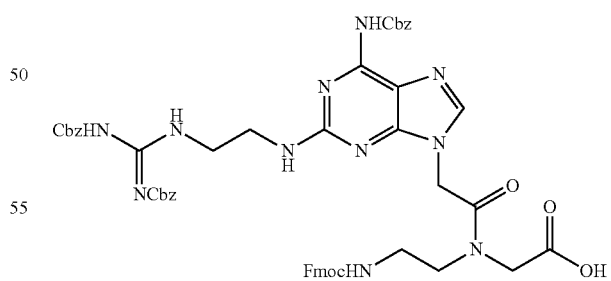

To 460 mg of compd 64 dissolved in 3.6 ml MC, was slowly added 3.6 ml TFA at 0° C. The reaction solution was stirred at RT for 3.5 h, and then 50 ml diethyl ether was added. The resulting precipitate was collected by filtration to yield 430 mg of compd 65 as a white solid. $^1$H NMR (400 MHz; DMSO$_{d6}$) δ 11.57 (s, 1H), 10.77 (br s, 1H), 8.66 (s, 1H), 8.54 (s, 1H), 7.87 (m, 2H), 7.63 (m, 2H), 7.50-7.28 (m, 21H), 5.26-4.96 (m, 8H), 4.34-4.18 (m, 4H), 4.03 (s, 1H), 3.52-3.36

(m, 7H), 3.13 (m, 1H). MS/ESI (m+1)=1019.4 (observed), MW=1018.0 ($C_{53}H_{51}N_{11}O_{11}$).

Example 66

Preparation of N-[2-{(9H-fluoren-9-yl)methoxycarbonylamino}-ethyl)]-N-[2-{6-(benzyloxycarbonylamino)-2-[4-{2,3-bis(benzyloxycarbonyl)-guanidino}-butyl]amino-9H-purin-9-yl}acetyl]glycine (66)

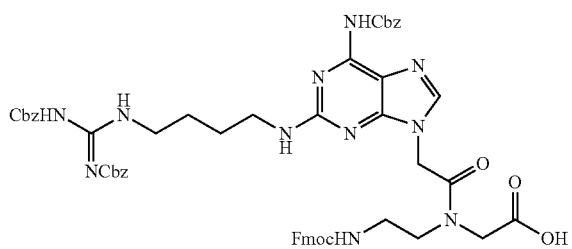

Compd 59 was converted to compd 66 as a white foam/solid by similarly following the procedures described in Examples 63~65. $^1$H NMR (500 MHz; DMSO$_{d6}$) δ 12.84 (br s, 1H), 11.50 (s, 1H), 10.14-10.13 (m, 1H), 8.28 (m, 1H), 7.88 (m, 2H), 7.80-7.77 (m, 1H), 7.68-7.66 (m, 2H), 7.49 (t, 1H), 7.45-7.29 (m, 9H), 6.90 (m, 1H), 5.17 (s, 2H), 5.07 (s, 1.2H), 4.89 (s, 0.8H), 4.35-4.18 (m, 3H), 4.00 (s, 1H), 3.52 (m, 1H), 3.35-3.25 (m, 6H), 3.12 (m, 1H), 1.49 (m, 4H), 1.44 (d, 9H), 1.37 (d, 9H). MS/ESI (m+1)=978.4 (observed), MW=978.1 ($C_{49}H_{59}N_{11}O_{11}$).

Example 67

Preparation of N-[2-{(9H-fluoren-9-yl)methoxycarbonylamino}-ethyl)]-N-[2-[6-[2-{2,3-bis(benzyloxycarbonyl)guanidino}ethoxy]methyl-2-oxo-2H-pyrrolo[2,3-d]pyrimidin-3(7H)-yl]acetyl]glycine (67)

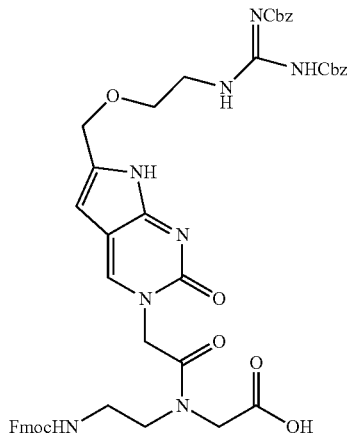

Compd 18 was converted to compd 67 as a pale yellow solid by similarly following the procedures described in Examples 63~65. $^1$H NMR (500 MHz; DMSO$_{d6}$) δ 11.99 (br s, 1H), 11.57 (br, 1H), 8.56 (m, 1H), 8.48-8.45 (m, 1H), 7.89-7.87 (m, 2H), 7.70-7.65 (m, 2H), 7.49-7.26 (m, 15H), 6.36-6.33 (m, 1H), 5.20 (s, 2H), 5.03-5.01 (m, 3.3H), 4.83 (s, 0.7H), 4.49-4.17 (m, 5.7H), 4.01 (m, 1.3H), 3.57-3.11 (m, 8H); MS/ESI (m+1)=899.7 (observed), MW=898.9 ($C_{47}H_{46}N_8O_{11}$).

Example 68

Preparation of N-[2-{(9H-fluoren-9-yl)methoxycarbonylamino}-ethyl)]-N-{2-[2-{2,3-bis-(benzyloxycarbonyl)guanidino}ethyl]amino-6-oxo-6,9-dihydro-1H-purin-2-yl]acetyl}glycine (68)

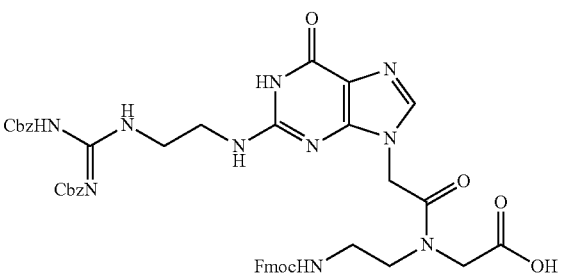

Compd 62 was converted to compd 68 as a white foam/solid by following the procedures described in Examples 63~65. $^1$H NMR (500 MHz; DMSO$_{d6}$) δ 11.58 (s, 1H), 10.88 (s, 1H), 8.51 (m, 1H), 7.93 (m, 1H), 7.87 (m, 2H), 7.64 (m, 2H), 7.47 (t, 1H), 7.41-7.26 (m, 14H), 6.66 (br, 1H), 5.16-4.89 (m, 8H), 4.34-4.18 (m, 3.8H), 4.00 (m, 1.2H), 3.50-3.35 (m, 7H), 3.13 (m, 1H); MS/ESI (m+1)=885.3 (observed), MW=884.9 ($C_{45}H_{44}N_{10}O_{10}$).

Example 69

Preparation of 2-[6-{2-(t-butoxycarbonylamino)ethoxy}methyl-2-oxo-2H-pyrrolo-[2,3-d]pyrimidin-3(7H)-yl]acetic acid (69)

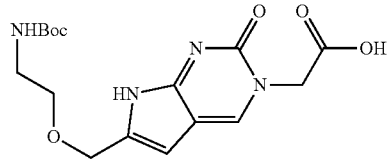 [SMILES: CC(C)(C)OC(=O)NCCOCc1cc2cn(CC(=O)O)c(=O)nc2[nH]1]

Compound 16 was hydrolyzed to compound 69 as a pale brown solid by similarly following the procedure described in Example 11. $^1$H NMR (500 MHz; DMSO$_{d6}$) δ 13.03 (br s, 1H), 11.31 (s, 1H), 8.37 (s, 1H), 6.85 (t, 1H), 6.19 (s, 1H), 4.63 (s, 2H), 4.40 (s, 2H), 3.42 (t, 2H), 3.11 (q, 2H), 1.37 (s, 9H).

Example 70

Preparation of methyl N-[2-{(9H-fluoren-9-yl)methoxycarbonylamino}ethyl)]-N-{2-[6-{2-(t-butoxycarbonylamino)ethoxy}methyl-2-oxo-2H-pyrrolo-[2,3-d]pyrimidin-3(7H)-yl]acetyl}glycinate (70)

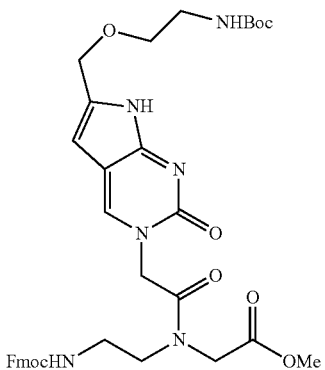

3.6 g of compd 69, 3.6 g of Fmoc-Aeg-OMe, 2.5 g of EDCI 1.73 g of HOBt, and 2.24 ml DIEA were dissolved in 70 ml DMF, and stirred at RT for 1.5 h. The reaction solvent was removed under reduced pressure, and the resulting residue was dissolved in 100 ml MC and washed in series with 1M aq HCl, distilled water, and brine. The organic layer was dried over anhydrous sodium sulfate, concentrated in vacuo, and purified by column chromatography (100:2 MC/MeOH) to afford 2.5 g of compd 70 as a yellow foam/solid. $^1$H NMR (500 MHz; DMSO$_{d6}$) δ 11.30 (s, 1H), 8.24 (s, 0.65H), 8.21 (s, 0.35H), 7.89-7.87 (m, 2H), 7.71-7.67 (m, 2H), 7.48-7.25 (m, 5H), 6.87 (t, 1H), 6.17 (s, 0.7H), 6.15 (s, 0.3H), 4.93 (s, 1.3H), 4.74 (s, 0.7H), 4.40-4.39 (m, 2.7H), 4.35-4.21 (m, 3H), 4.08 (s, 1.3H), 3.73 (s, 0.8H), 3.62 (s, 2.2H), 3.51 (t, 1.4H), 3.43-3.30 (m, 3.6H), 3.13-3.10 (m, 3H), 1.37 (s, 9H).

Example 71

Preparation of N-[2-{(9H-fluoren-9-yl)methoxycarbonylamino}-ethyl)]-N-{2-[6-{2-(t-butoxycarbonylamino)ethoxy}methyl-2-oxo-2H-pyrrolo-[2,3-d]pyrimidin-3(7H)-yl]acetyl}glycine (71)

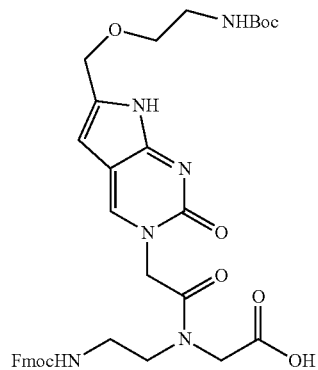

To 5.0 g of compd 70 dissolved in 75 ml 1:1:1 acetonitrile/acetone/water, was slowly added at 0° C. 28.5 ml 2.5N aq LiOH. The reaction solution was stirred for 10 min and neutralized with 20% aq citric acid. After the solution pH was adjusted to 8 with saturated aq sodium bicarbonate, 516 mg of Fmoc-OSu was added to the solution and the solution was stirred for 2 h at RT. Then the solution was acidified to pH 3 with 20% aq citric acid and stirred for 90 min at 0° C. The resulting precipitate was collected by filtration to give 4.0 g of compd 71 as a yellowish green solid. $^1$H NMR (500 MHz; DMSO$_{d6}$) δ 12.02 (br, 1H), 8.51-8.49 (m, 1H), 7.89-7.88 (d, 2H), 7.70-7.50 (m, 2H), 7.49 (t, 1H), 7.42-7.28 (m, 4H), 6.87 (t, 1H), 6.36 (s, 0.7H), 6.33 (s, 0.3H), 5.02 (s, 1.2H), 4.84 (0.8H), 4.43-4.42 (m, 2.4H), 4.34-4.19 (m, 3.2H), 4.01 (s, 1.4H), 3.48 (t, 1.2H), 3.44-3.41 (m, 2.1H), 3.37-3.29 (m, 2H), 3.12-3.10 (m, 2.7H), 1.37 (s, 9H); MS/ESI (m+1)=689.3 (observed), MW=688.7 ($C_{35}H_{40}N_6O_9$).

Example 72

Preparation of N-[2-{(9H-fluoren-9-yl)methoxycarbonylamino}-ethyl)]-N-{2-[5-{(t-butoxycarbonyl)amino}pentyl]amino-6-oxo-6,9-dihydro-1H-purin-2-yl]acetyl}glycine (72)

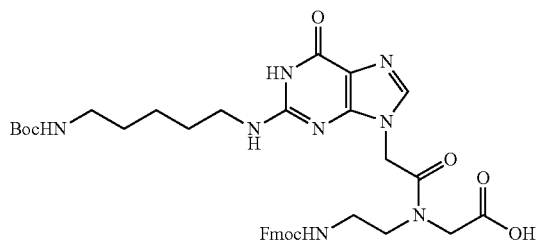

Compd 51 was converted to compd 72 as a white foam/solid by similarly following the procedures described in Examples 69~71. $^1$H NMR (500 MHz; DMSO$_{d6}$) δ 13.01 (br, 1H), 10.52-10.46 (m, 1H), 7.88 (d, 2H), 7.65 (d, 2H), 7.54 (s, 0.5H), 7.50 (s, 0.5H), 7.48 (m, 1H), 7.40 (t, 2H), 7.31 (m, 2H), 6.81 (t, 0.5H), 6.72 (t, 0.5H), 6.52-6.48 (m, 1H), 4.98 (s, 1H), 4.77 (s, 1H), 4.33 (d, 1H), 4.23-4.21 (m, 2H), 4.05 (m, 1H), 3.96 (s, 1H), 3.50 (m, 1H), 3.35 (m, 2H), 3.21 (m, 2H), 3.14 (q, 1H), 2.88 (m, 2H), 1.46 (q, 2H), 1.39-1.35 (m, 11H), 1.23 (m, 2H); MS/ESI (m+1)=717.4 (observed), MW=716.8 ($C_{36}H_{44}N_8O_8$).

Example 73

Preparation of N-[2-{(9H-fluoren-9-yl)methoxycarbonylamino}-ethyl)]-N-[2-[6-{bis(t-butoxycarbonyl)amino}-2-{5-(t-butoxycarbonylamino)-pentyl}amino-9H-purin-9-yl]acetyl]glycine (73)

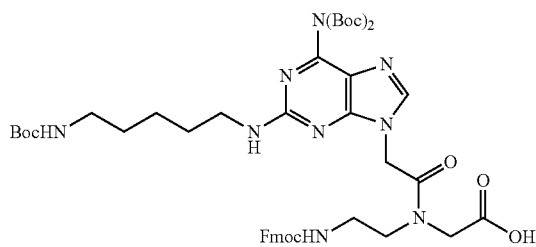

Compd 61 was converted to compd 73 as a white foam/solid by similarly following the procedures described in Examples 69~71. $^1$H NMR (500 MHz; DMSO$_{d6}$) δ 12.71 (br s, 1H), 7.90-7.87 (m, 3H), 7.67 (m, 2H), 7.44-7.39 (m, 3H), 7.31 (m, 2H), 7.07 (m, 1H), 6.69 (m, 1H), 5.11 (s, 1.2H), 4.93 (s, 0.8H), 4.37-4.21 (m, 3.8H), 4.01 (s, 1.2H), 3.52 (m, 1H), 3.36 (m, 2H), 3.23 (m, 2H), 3.13 (m, 1H), 2.88 (m, 2H), 1.49 (m, 2H), 1.38-1.35 (m, 27H), 1.27-1.25 (m, 4H); MS/ESI (m+1)=916.5 (observed), MW=916.0 ($C_{46}H_{61}N_9O_{11}$).

Preparation of PNA Oligomers:

PNA monomers o, which were synthesized according to Scheme 4, were sent to Panagene, Inc (www.panagene.com, Daejon, South Korea) to prepare PNA oligomers of Formula I by Panagene according to the method described in the literature or with minor modification(s) thereof. (*Org. Lett.* vol 9, 3291-3293, 2006) PNA oligomers were received from Panagene as characterized by MALDI-TOF and analyzed by $C_{18}$-reverse phase HPLC. PNA oligomers received from Panagene were used without further purification.

PNA monomers q of Scheme 5 were used to synthesize PNA oligomers of Formula I according to the method disclosed in the prior art or with minor modification(s) thereof. (U.S. Pat. No. 6,133,444) Those PNA oligomers were purified by $C_{18}$-reverse phase HPLC (aq acetonitrile with 0.1% TFA) and characterized by MALDI-TOF. FIG. 1 provides HPLC chromatograms before and after purification of Oligo 17 by reverse phase HPLC. FIG. 2 provides a MALDI-TOF mass spectrum for a purified batch of Oligo 17. FIGS. 1 and 2 are provided for illustrative purposes only and should not be interpreted as a restriction to this invention.

PNA oligomers synthesized for this invention are provided in Table 1 along with their molecular weight data by MALDI-TOF. Of the abbreviations used in Table 1, A, T, G, and C refer to unmodified nucleobase adenine, thymine, guanine, and cytosine, respectively. Modified nucleobases C(mXn), C(mXn$_g$), A(mXn), A(m), A(m$_g$), and G(m) are as defined below Table 1 along with Lys, Fam, L(1), and L(2). These PNA oligomers are presented for illustrative purposes only and should not be interpreted as a restriction to the present invention.

TABLE 1

PNA oligomers of this invention and mass spectral data thereof.[a]

| Entry | Sequence (N → C) | MW | (m + 1)[b] |
|---|---|---|---|
| Oligo 1 | Fam-L(1)L(1)-TGC(1O3)-TAC(1O3)-TAC(1O3)-TG-Lys-NH$_2$ | 4079.0 | 4078.3 |
| Oligo 2 | Fam-L(1)L(1)-TGC-TAC-TAC-TG-Lys-NH$_2$ | 3745.6 | 3745.5 |
| Oligo 3 | TGC(1O3)-TAC-TAC(1O3)-TG-Lys-NH$_2$ | 3319.4 | 3318.5 |
| Oligo 4 | TGC-TAC(1O3)-TAC-TG-Lys-NH$_2$ | 3208.3 | 3208.3 |
| Oligo 5 | TGC-TAC-TAC-TG-Lys-NH$_2$ | 3097.2 | 3097.8 |
| Oligo 6 | Fam-L(1)L(1)-TC(1O3)T-CC(1O3)C-AGC(1O3)-GTG-C(1O3)GC-C(1O3)AT-Lys-NH$_2$ | 6140.1 | 6141.8 |
| Oligo 7 | Fam-L(1)L(1)-TCT-CCC-AGC-GTG-CGC-CAT-Lys-NH$_2$ | 5584.4 | 5583.1 |
| Oligo 8 | TGC(2O2)-TAC-TAC(2O2)-TG-Lys-NH$_2$ | 3319.4 | 3318.9 |
| Oligo 9 | GC(2O2)A-C(2O2)AT-TTG-C(2O2)CT-NH$_2$ | 3553.7 | 3552.7 |
| Oligo 10 | GC(1O2)A-C(1O2)AT-TTG-C(1O2)CT-NH$_2$ | 3511.6 | 3511.1 |
| Oligo 11 | GCA-CAT-TTG-CCT-Lys-NH$_2$ | 3348.3 | 3345.8 |
| Oligo 12 | CA(3)T-A(3)GT-A(3)TA-A(3)GT-NH$_2$ | 3580.8 | 3580.9 |
| Oligo 13 | CA(4)T-A(4)GT-A(4)TA-A(4)GT-NH$_2$ | 3636.9 | 3634.9 |
| Oligo 14 | CA(5)T-A(5)GT-A(5)TA-A(5)GT-NH$_2$ | 3693.0 | 3691.5 |
| Oligo 15 | CA(7)T-A(7)GT-A(7)TA-A(7)GT-NH$_2$ | 3805.0 | 3803.4 |
| Oligo 16 | CAT-AGT-ATA-AGT-Lys-NH$_2$ | 3420.3 | 3418.3 |
| Oligo 17 | CA(5)T-A(5)GT-A(5)TA-A(5)GT-Lys-NH$_2$ | 3820.9 | 3819.8 |
| Oligo 18 | CA(2O2)T-A(2O2)GT-A(2O2)TA-A(2O2)GT-NH$_2$ | 3700.7 | 3701.4 |
| Oligo 19 | L(1)-TAG(2O3)-CTG(2O3)-CTG-ATT-Lys-NH$_2$ | 3746.9 | 3748.9 |
| Oligo 20 | TG(5)G-C(1O2)AA-C(1O2)TG-A(5)T-Lys-NH$_2$ | 3525.6 | 3523.8 |
| Oligo 21 | Fam-L(2)-TG(5)G-C(1O2)AA-C(1O2)TG-A(5)T-Lys-NH$_2$ | 3997.0 | 3996.1 |
| Oligo 22 | Fam-L(2)-TT-C(1O2)AT-A(5)GT-A(5)TA-AG(5)T-Lys-NH$_2$ | 4806.9 | 4806.7 |
| Oligo 23 | Fam-L(2)L(2)-TC(1O2)A-GA(5)A-C(1O2)TT-A(5)T-Lys-NH$_2$ | 4084.2 | 4083.8 |
| Oligo 24 | Fam-L(2)-CA(5)T-A($4_g$)GT-A($4_g$)TA(5)-AGT-Lys-NH$_2$ | 4348.5 | 4347.4 |
| Oligo 25 | TT-C(1O2$_g$)AT-A(5)GT-A(5)TA-AG(5)T-Lys-NH$_2$ | 4377.4 | 4375.6 |
| Oligo 26 | GC(1N3)A-C(1N3)AT-TTG-C(1N3)CT-NH$_2$ | 3550.8 | 3550.9 |
| Oligo 27 | CAT-AGT-ATA-AGT-NH$_2$ | 3292.3 | 3292.5 |
| Oligo 28 | Fam-L(2)-TGG-CAA-CTG-AT-Lys-NH$_2$ | 3617.5 | 3616.3 |

[a]The employed abbreviations for monomers are defined as below.
[b]Observed ion peak for MH$^+$ unless noted otherwise.

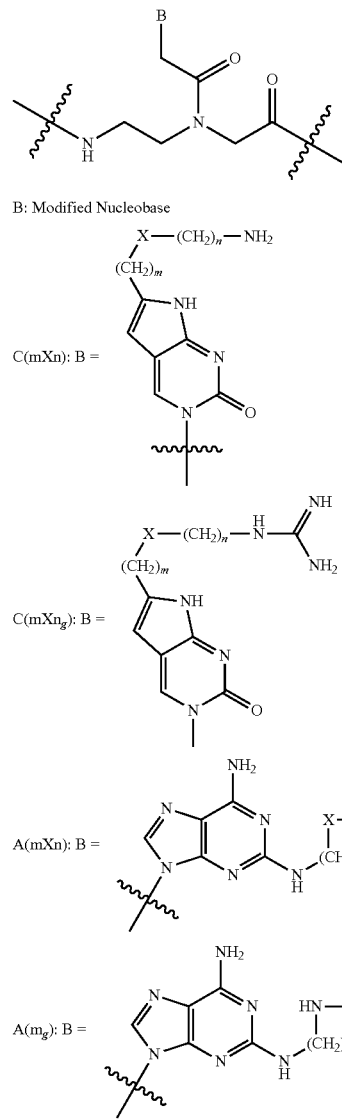

B: Modified Nucleobase

TABLE 1-continued

PNA oligomers of this invention and mass spectral data thereof.[a]

| Entry | Sequence (N → C) | MW (m + 1)[b] |
|---|---|---|

A(m): B = [structure: adenine with -NH-(CH₂)ₘ-NH₂ substituent]

G(m): B = [structure: guanine with -NH-(CH₂)ₘ-NH₂ substituent]

L(1): [structure: -NH-CH₂CH₂-O-CH₂CH₂-O-CH₂-C(=O)-]

L(2): [structure: -NH-(CH₂)₅-C(=O)-]

Fam: [structure: fluorescein with COOH and carbonyl linker]

Lys: [structure: lysine residue with side chain -NH₂]

Binding Affinity for DNA:

PNA oligomers of this invention were evaluated for their binding affinity for DNA by measuring $T_m$ values as follows. 4 μM PNA oligomer and 4 μM DNA were mixed in aq buffer (pH 7.16, 10 mM sodium phosphate, 100 mM NaCl), and incubated at 90° C. for a few minutes and slowly cooled down to RT. Then the solution was transferred into a 4 ml quartz cuvette and the cuvette was tightly sealed. The cuvette was mounted on an Agilent 8453 UV/Visible spectrophotometer and absorbance changes at 260 nm were recorded with increasing the temperature of the cuvette by either 0.5 or 1.0° C. per minute. From the absorbance vs temperature curve, the temperature showing the largest increase rate in absorbance was read out as the melting temperature $T_m$ between PNA and DNA. DNAs for $T_m$ measurement were purchased either from Bioneer, Inc. (www.bioneer.com, Daejon, South Korea) or from Ahram Biosystems (www.ahrambio.com, Seoul, South Korea), and used without further purification.

FIG. 3 provides graphs of absorbance changes with temperature for Oligo 17 against complementary or mismatch DNA. For sequences of the mismatch DNAs against Oligo 17, refer to Table 2. In FIG. 3, there is a transition temperature in each curve, which was read out as the $T_m$ value for the curve.

$T_m$ values are provided in Table 2 for PNA oligomers of this invention. These $T_m$ values are presented for illustrative purposes only and should not be interpreted as a restriction to this invention.

TABLE 2

$T_m$ values between PNA and complementary or mismatch DNA.

| Entry | DNA Sequence (5' → 3') | $T_m$, ° C. | Remark |
|---|---|---|---|
| Oligo 5 | CAG-TAG-TAG-CA | 55 | unmodified PNA oligomer |
| Oligo 3 | | 65 | C(103) × 2 |
| Oligo 4 | | 61 | C(103) × 1 |
| Oligo 8 | | 68 | C(202) × 2 |
| Oligo 10 | AGG-CAA-TTG-TGC | >85 | C(102) × 3 |
| Oligo 11 | | 59 | unmodified PNA oligomer |
| Oligo 12 | ACT-TAT-ACT-ATG | 60 | A(3) × 4 |
| Oligo 13 | | 64 | A(4) × 4 |
| Oligo 14 | | 69 | A(5) × 4 |
| Oligo 15 | | 71 | A(7) × 4 |
| Oligo 18 | | 66 | A(202) × 4 |
| Oligo 27 | | 55 | unmodified PNA oligomer |
| Oligo 16 | ACT-TAT-ACT-ATG | 56 | unmodified PNA oligomer |
| Oligo 17 | ACT-TAT-ACT-ATG | 72 | complementary |
| | ACT-TAC-ACT-ATG | 61 | mismatch (T → C) |
| | ACT-TAA-ACT-ATG | 59 | mismatch (T → A) |
| | ACT-TAG-ACT-ATG | 58 | mismatch (T → G) |
| Oligo 24 | ACT-TAT-ACT-ATG | 70 | A(5) × 2 plus A(4g) × 2 |
| Oligo 20 | ATC-AGT-TGC-CA | 84 | complementary |

TABLE 2-continued

T_m values between PNA and complementary or mismatch DNA.

| Entry | DNA Sequence (5' → 3') | $T_m$, °C. | Remark |
|---|---|---|---|
| | ATC-ATT-TGC-CA | 62 | mismatch (G → T) |
| | ATC-AAT-TGC-CA | 65 | mismatch (G → A) |

Replacement of cytosine with an unnatural nucleobase pyrrolocytosine derivative of this invention markedly increased PNA oligomer's affinity for complementary DNA. For example, Oligo 10 having three 'modified' cytosine 'C(1O2)' monomers showed a $T_m$ exceeding 85° C., while the corresponding 'unmodified' Oligo 11 showed a $T_m$ of 58° C. Other modified cytosine monomers such as 'C(1O3)' or 'C(2O2)' also significantly increased PNA oligomer's affinity for complementary DNA, as exemplified with Oligo 3 and Oligo 8.

'Modified' adenine nucleobases of this invention also significantly increased PNA oligomer's affinity for complementary DNA. For example, Oligo 15 having four 'modified' adenine A(7) monomers showed a $T_m$ of 71° C., which is significantly higher than the $T_m$ of 55° C. observed with 'unmodified' Oligo 27. Other 'modified' adenine monomers such as A(4), and A(5) also markedly increased affinity for complementary DNA.

'Modified' PNA monomers of this invention were found to be quite sensitive to base mismatch. For example, decreases of 11~14° C. in $T_m$ were observed with single base mismatches for an A(5) monomer in Oligo 17. Single base mismatches for a C(1O2) monomer in Oligo 20 resulted in decreases of 19~22° C. in $T_m$.

Cell Penetration:

In order to evaluate the cell penetration ability of PNA oligomers of this invention, cancer cells of human origin were treated with PNA oligomers covalently tagged with fluorescein. The applied method is provided in brief as follows.

To each cover glass (autoclaved) placed in each well of a 24-well plate, were seeded 20,000~100,000 cells depending on the growth rate of the cell line used, and the cells were cultured at 37° C. and 5% $CO_2$ for 16 to 24 h. Then the medium was replaced with 5000 fresh Opti-MEM medium (with or without 1% FBS), to which was added an aliquot of aq stock solution of a PNA oligomer covalently tagged with fluorescein. After cells were cultured for a designated interval, the cells were washed with PBS, and fixed by incubating in 3.7% or 4% paraformaldehyde. The cells were thoroughly washed several times with PBS or PBS containing 0.1% Tween-20. Then the cover glass was mounted onto a slide glass using a drop of mounting solution and sealed with nail polish for confocal fluorescence microscopy. Fluorescence images were taken either on a Zeiss LSM 510 confocal microscope (Germany) at 63× objective or on a Nikon C1Si confocal microscope at 40× objective.

The cell penetration images in FIGS. 4~8 are provided for illustrative purposes only and should not be interpreted as a restriction to the present invention.

In FIGS. 4(a) and 4(b), are provided confocal microscopy images (at 63× objective) 1, 2, 3 and 24 h after HeLa cells were treated with Oligo 1 and Oligo 2 at 5 µM, respectively (without FBS). While fluorescence intensity is clear and becomes intense over 24 h in FIG. 4(a), fluorescence intensity is faint in FIG. 4(b), indicating that Oligo 1 penetrates HeLa cells significantly faster than 'unmodified' Oligo 2.

In FIGS. 5(a) and 5(b), are provided confocal microscopy images (at 63× objective) 0.5 and 1 h after MCF-7 cells were treated with Oligo 6 and Oligo 7 at 2.5 µM, respectively (without FBS). While fluorescence intensity is clear and becomes intense over 1 h in FIG. 5(a), fluorescence intensity is faint in FIG. 5(b), indicating that Oligo 6 penetrates MCF-7 cells significantly faster than 'unmodified' Oligo 7.

In FIGS. 6(a) and 6(b), are provided confocal microscopy pictures (at 40× objective) 6 or 24 h after HeLa cells were treated with Oligo 1 and Oligo 6 at 1 µM, respectively (with 1% FBS). While fluorescence intensity is faint even at 24 h in FIG. 6(a), fluorescence intensity is clear and becomes intense over 24 h in FIG. 6(b), suggesting that Oligo 6 penetrate HeLa Cells significantly faster than Oligo 1.

In FIGS. 7(a) and 7(b), are provided confocal microscopy pictures (40× objective) 24 h after JAR cells were treated with Oligo 21 and Oligo 28 at 2 µM, respectively (without FBS). While fluorescence intensity is strong in FIG. 7(a), there is no significant fluorescence intensity in FIG. 7(b), suggesting that Oligo 21 penetrate JAR cells significantly faster than 'unmodified' Oligo 28.

In FIGS. 7(c) and 7(d), are provided confocal microscopy pictures (at 40× objective) 24 h after A549 cells were treated with Oligo 21 and Oligo 28 at 2 µM, respectively (without FBS). While fluorescence intensity is strong in FIG. 7(c), there is no significant fluorescence intensity in FIG. 7(d), suggesting that Oligo 21 penetrate A549 cells significantly faster than 'unmodified' Oligo 28.

In FIGS. 7(e) and 7(f), are provided confocal microscopy pictures (at 40× objective) 12 h after HeLa cells were treated with Oligo 21 and Oligo 28 at 2 µM, respectively (without FBS). While fluorescence intensity is apparent in FIG. 7(e), there is no significant fluorescence intensity in FIG. 7(f), suggesting that Oligo 21 penetrate HeLa cells significantly faster than 'unmodified' Oligo 28.

In FIG. 7(g), are provided confocal microscopy pictures (at 40× objective) 24 h after HeLa cells were treated with Oligo 21 at 2 µM (without FBS). Given that the celluar fluorescence in FIG. 7(g) is significantly stronger than that in FIG. 7(e), Oligo 21 appears to penetrate over 24 h rather than 12 h.

FIGS. 8(a), 8(b) and 8(c) provide confocal microscopy images (40× objective) 24 h after HeLa, A549, and JAR cells were treated with 2 µM Oligo 22, respectively (without FBS). All the images are associated with fluorescence within cell, indicating that Oligo 22 possesses good cell penetration in the tested cells.

Antisense Example:

Oligo 9 and Oligo 12 possess the same base sequences as T1-12 and T5-12, respectively, which were reported to inhibit the ribosomal synthesis of mdm2 in the literature. (*Nucleic Acids Res.* vol 32, 4893-4902, 2004) Oligo 9 and Oligo 12 were evaluated for their ability to inhibit the ribosomal synthesis of mdm2 in JAR cells as follows. The following antisense example is presented for illustrative purposes only and should not be interpreted as a restriction to the present invention.

JAR cells (ATCC catalog #HTB-144) were grown in RPMI-1640 medium supplemented with 10% FBS and 1% penicillin-streptomycin at 37° C. and 5% $CO_2$. Cells were then seeded into each well of a 12-well plate containing 1 ml of the same medium, and treated with an aliquot of an aqueous stock solution of Oligo 9 or Oligo 12 of a designated concentration. Then the cells were incubated at 37° C. and 5% $CO_2$ for 15 h.

The cells in each well were washed with cold PBS and treated with 80 μl RIPA buffer containing 1% protease inhibitors cocktail, and the plate was incubated at 4° C. and agitated slowly for 15 min. The content of each well was scraped out into a microtube. The microtube was incubated in ice for 10 min and centrifuged at 10,000 g. The resulting supernatant was collected and subjected to protein quantification by Bradford assay and western blot analysis. For electrophoresis, 20 μg of protein was loaded onto each lane of the gel in a minigel apparatus, separated and transferred onto a PVDF membrane (0.45μ, Millipore). The primary mdm2 antibody used for western blotting was SC-965 (Santa Cruz Biotechnology).

FIG. 9 provides western blotting results for JAR cells treated with 5 μM or 10 μM Oligo 9, 5 μM or 10 μM Oligo 10, cotreatment with the oligomers at 5 μM or 10 μM each, and blank (no oligomer treatment). In FIG. 9, treatment with Oligo 9 or Oligo 10, or cotreatment with Oligo 9 and Oligo 10 significantly inhibited ribosomal synthesis of mdm2 in JAR cells both at 5 μM and 10 μM.

The invention claimed is:

1. A compound of Formula VI:

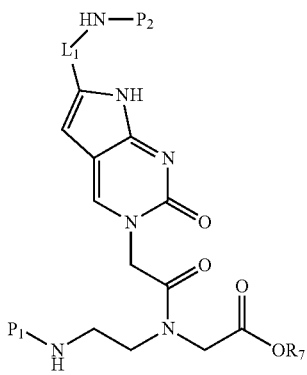

Formula VI wherein, $R_7$ is hydrido, N-succinyl, or substituted or non-substituted alkyl radical;

$P_1$ is selected from hydrido, t-butoxycarbonyl, (9H-fluoren-9-yl)methoxy-carbonyl, substituted or non-substituted benzyloxycarbonyl, and substituted or non-substituted arylsulfonyl radical;

$P_2$ is selected from hydrido, t-butoxycarbonyl, (9H-fluoren-9-yl)methoxy-carbonyl, substituted or non-substituted benzyloxycarbonyl, substituted alkyloxycarbonyl, substituted or non-substituted alkyl, amidinyl, 1,3-bis(t-butoxy-carbonyl)amidinyl, 1,3-bis-(benzyloxycarbonyl)amidinyl radical; and, $L_1$ is a linker represented by Formula V:

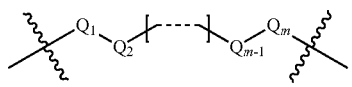

Formula V wherein, $Q_1$ and $Q_m$ are substituted or non-substituted methylene radical, and $Q_m$ is directly linked to the amino radical;

$Q_2, Q_3, \ldots,$ and $Q_{m-1}$ are independently selected from substituted or non-substituted methylene, oxygen, sulfur, and substituted or non-substituted amino radical; and, m is an integer from 2 to 15.

2. A compound of Formula IX:

Formula IX wherein, $R_{10}$ is hydroxy, substituted or non-substituted alkyloxy, or substituted or non-substituted amino radical;

$P_2$ is selected from hydrido, t-butoxycarbonyl, (9H-fluoren-9-yl)methoxy-carbonyl, substituted or non-substituted benzyloxycarbonyl, substituted alkyloxycarbonyl, substituted or non-substituted alkyl, amidinyl, 1,3-bis(t-butoxy-carbonyl)amidinyl, 1,3-bis-(benzyloxycarbonyl)amidinyl radical; and, $L_1$ is a linker represented by Formula V:

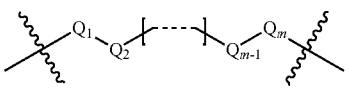

Formula V wherein, $Q_1$ and $Q_m$ are substituted or non-substituted methylene radical, and $Q_m$ is directly linked to the amino radical;

$Q_2, Q_3, \ldots,$ and $Q_{m-1}$ are independently selected from substituted or non-substituted methylene, oxygen, sulfur, and substituted or non-substituted amino radical; and, m is an integer from 2 to 15.

* * * * *

```
                        SEQUENCE LISTING

<160> NUMBER OF SEQ ID NOS: 35

<210> SEQ ID NO 1
<211> LENGTH: 11
<212> TYPE: DNA
<213> ORGANISM: Artificial Sequence
<220> FEATURE:
<223> OTHER INFORMATION: PNA modified nucleotide
<220> FEATURE:
<221> NAME/KEY: misc_feature
<222> LOCATION: (1)..(1)
<223> OTHER INFORMATION: Acylated N-terminal
<220> FEATURE:
<221> NAME/KEY: misc_feature
<222> LOCATION: (1)..(11)
<223> OTHER INFORMATION: PNA modified oligonucleotide

<400> SEQUENCE: 1
tgntantant g                                                          11

<210> SEQ ID NO 2
<211> LENGTH: 11
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(1)
<223> OTHER INFORMATION: Acylated N-terminal
<220> FEATURE:
<221> NAME/KEY: misc_feature
<222> LOCATION: (1)..(11)
<223> OTHER INFORMATION: PNA modified oligonucleotide

<400> SEQUENCE: 2
tgctactact g                                                          11

<210> SEQ ID NO 3
<211> LENGTH: 11
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(11)
<223> OTHER INFORMATION: PNA modified oligonucleotide

<400> SEQUENCE: 3
tgntactant g                                                          11

<210> SEQ ID NO 4
<211> LENGTH: 11
<212> TYPE: DNA
<213> ORGANISM: Artificial Sequence
```

-continued

```
<220> FEATURE:
<223> OTHER INFORMATION: modified PNA oligonucleotide
<220> FEATURE:
<221> NAME/KEY: misc_feature
<222> LOCATION: (1)..(11)
<223> OTHER INFORMATION: PNA modified oligonucleotide

<400> SEQUENCE: 4
tgctantact g                                                          11

<210> SEQ ID NO 5
<211> LENGTH: 11
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(11)
<223> OTHER INFORMATION: PNA modified oligonucleotide

<400> SEQUENCE: 5
tgctactact g                                                          11

<210> SEQ ID NO 6
<211> LENGTH: 18
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(1)
<223> OTHER INFORMATION: Acylated N-terminal
<220> FEATURE:
<221> NAME/KEY: misc_feature
<222> LOCATION: (1)..(18)
<223> OTHER INFORMATION: PNA modified oligonucleotide

<400> SEQUENCE: 6
tntcncagng tgngcnat                                                   18

<210> SEQ ID NO 7
<211> LENGTH: 18
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(1)
<223> OTHER INFORMATION: Acylated N-terminal
<220> FEATURE:
<221> NAME/KEY: misc_feature
<222> LOCATION: (1)..(18)
<223> OTHER INFORMATION: PNA modified oligonucleotide

<400> SEQUENCE: 7
tctcccagcg tgcgccat                                                   18

<210> SEQ ID NO 8
<211> LENGTH: 11
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(11)
<223> OTHER INFORMATION: PNA modified oligonucleotide
```

```
<400> SEQUENCE: 8
tgntactant g                                                            11

<210> SEQ ID NO 9
<211> LENGTH: 12
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(12)
<223> OTHER INFORMATION: PNA modified oligonucleotide

<400> SEQUENCE: 9
gnanatttgn ct                                                           12

<210> SEQ ID NO 10
<211> LENGTH: 12
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(12)
<223> OTHER INFORMATION: PNA modified oligonucleotide

<400> SEQUENCE: 10
gnanatttgn ct                                                           12

<210> SEQ ID NO 11
<211> LENGTH: 12
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(12)
<223> OTHER INFORMATION: PNA modified oligonucleotide

<400> SEQUENCE: 11
gcacatttgc ct                                                           12

<210> SEQ ID NO 12
<211> LENGTH: 12
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(12)
<223> OTHER INFORMATION: PNA modified oligonucleotide

<400> SEQUENCE: 12
cntngtntan gt                                                           12

<210> SEQ ID NO 13
<211> LENGTH: 12
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(12)
<223> OTHER INFORMATION: PNA modified oligonucleotide
```

```
<400> SEQUENCE: 13
cntngtntan gt                                                          12

<210> SEQ ID NO 14
<211> LENGTH: 12
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(12)
<223> OTHER INFORMATION: PNA modified oligonucleotide

<400> SEQUENCE: 14
cntngtntan gt                                                          12

<210> SEQ ID NO 15
<211> LENGTH: 12
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(12)
<223> OTHER INFORMATION: PNA modified oligonucleotide

<400> SEQUENCE: 15
cntngtntan gt                                                          12

<210> SEQ ID NO 16
<211> LENGTH: 12
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(12)
<223> OTHER INFORMATION: PNA modified oligonucleotide

<400> SEQUENCE: 16
catagtataa gt                                                          12

<210> SEQ ID NO 17
<211> LENGTH: 12
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(12)
<223> OTHER INFORMATION: PNA modified oligonucleotide

<400> SEQUENCE: 17
cntngtntan gt                                                          12

<210> SEQ ID NO 18
<211> LENGTH: 12
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(12)
```

```
<223> OTHER INFORMATION: PNA modified oligonucleotide

<400> SEQUENCE: 18
cntngtntan gt                                                          12

<210> SEQ ID NO 19
<211> LENGTH: 12
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(1)
<223> OTHER INFORMATION: Acylated N-terminal
<220> FEATURE:
<221> NAME/KEY: misc_feature
<222> LOCATION: (1)..(12)
<223> OTHER INFORMATION: PNA modified oligonucleotide

<400> SEQUENCE: 19
tanctnctga tt                                                          12

<210> SEQ ID NO 20
<211> LENGTH: 11
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(11)
<223> OTHER INFORMATION: PNA modified oligonucleotide

<400> SEQUENCE: 20
tngnaantgn t                                                           11

<210> SEQ ID NO 21
<211> LENGTH: 11
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(1)
<223> OTHER INFORMATION: Acylated N-terminal
<220> FEATURE:
<221> NAME/KEY: misc_feature
<222> LOCATION: (1)..(11)
<223> OTHER INFORMATION: PNA modified oligonucleotide

<400> SEQUENCE: 21
tngnaantgn t                                                           11

<210> SEQ ID NO 22
<211> LENGTH: 14
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(1)
<223> OTHER INFORMATION: Acylated N-terminal
<220> FEATURE:
<221> NAME/KEY: misc_feature
<222> LOCATION: (1)..(14)
<223> OTHER INFORMATION: PNA modified oligonucleotide

<400> SEQUENCE: 22
```

-continued

```
ttnatngtnt aant                                                 14

<210> SEQ ID NO 23
<211> LENGTH: 11
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(1)
<223> OTHER INFORMATION: Acylated N-terminal
<220> FEATURE:
<221> NAME/KEY: misc_feature
<222> LOCATION: (1)..(11)
<223> OTHER INFORMATION: PNA modified oligonucleotide

<400> SEQUENCE: 23
tnagnanttn t                                                    11

<210> SEQ ID NO 24
<211> LENGTH: 12
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(1)
<223> OTHER INFORMATION: Acylated N-terminal
<220> FEATURE:
<221> NAME/KEY: misc_feature
<222> LOCATION: (1)..(12)
<223> OTHER INFORMATION: PNA modified oligonucleotide

<400> SEQUENCE: 24
cntngtntna gt                                                   12

<210> SEQ ID NO 25
<211> LENGTH: 14
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(14)
<223> OTHER INFORMATION: PNA modified oligonucleotide

<400> SEQUENCE: 25
ttnatngtnt aant                                                 14

<210> SEQ ID NO 26
<211> LENGTH: 12
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(12)
<223> OTHER INFORMATION: PNA modified oligonucleotide

<400> SEQUENCE: 26
gnanatttgn ct                                                   12

<210> SEQ ID NO 27
<211> LENGTH: 12
<212> TYPE: DNA
```

```
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(12)
<223> OTHER INFORMATION: PNA modified oligonucleotide

<400> SEQUENCE: 27
catagtataa gt                                                              12

<210> SEQ ID NO 28
<211> LENGTH: 11
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(1)
<223> OTHER INFORMATION: Acylated N-terminal
<220> FEATURE:
<221> NAME/KEY: misc_feature
<222> LOCATION: (1)..(11)
<223> OTHER INFORMATION: PNA modified oligonucleotide

<400> SEQUENCE: 28
tggcaactga t                                                               11

<210> SEQ ID NO 29
<211> LENGTH: 11
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(11)
<223> OTHER INFORMATION: DNA oligonucleotide

<400> SEQUENCE: 29
nagtagtagn a                                                               11

<210> SEQ ID NO 30
<211> LENGTH: 12
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(12)
<223> OTHER INFORMATION: DNA oligonucleotide

<400> SEQUENCE: 30
aggnaattgt gn                                                              12

<210> SEQ ID NO 31
<211> LENGTH: 12
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(12)
<223> OTHER INFORMATION: DNA oligonucleotide

<400> SEQUENCE: 31
ncttntnctn tg                                                              12
```

```
<210> SEQ ID NO 32
<211> LENGTH: 12
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(12)
<223> OTHER INFORMATION: DNA oligonucleotide

<400> SEQUENCE: 32
acttatacta tg                                                           12

<210> SEQ ID NO 33
<211> LENGTH: 12
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(12)
<223> OTHER INFORMATION: DNA oligonucleotide

<400> SEQUENCE: 33
acttanacta tg                                                           12

<210> SEQ ID NO 34
<211> LENGTH: 12
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(12)
<223> OTHER INFORMATION: DNA oligonucleotide

<400> SEQUENCE: 34
ncttntnctn tg                                                           12

<210> SEQ ID NO 35
<211> LENGTH: 11
<212> TYPE: DNA
<213> ORGANISM: Artificial Sequence
<220> FEATURE:
<223> OTHER INFORMATION: PNA modified oligonucleotide
<220> FEATURE:
<221> NAME/KEY: misc_feature
<222> LOCATION: (1)..(11)
<223> OTHER INFORMATION: DNA oligonucleotide

<400> SEQUENCE: 35
atcanttgcc a                                                            11
```